US011252957B2

(12) United States Patent
Tomich et al.

(10) Patent No.: US 11,252,957 B2
(45) Date of Patent: Feb. 22, 2022

(54) NUCLEIC ACID-PEPTIDE CAPSULE COMPLEXES

(71) Applicant: Kansas State University Research Foundation, Manhattan, KS (US)

(72) Inventors: John M. Tomich, Manhattan, KS (US); Gerald Reeck, Manhattan, KS (US); Luz Adriana Avila Flores, Auburn, AL (US); Raman Chandrasekar, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 408 days.

(21) Appl. No.: 16/328,946

(22) PCT Filed: Aug. 31, 2017

(86) PCT No.: PCT/US2017/049668
§ 371 (c)(1),
(2) Date: Feb. 27, 2019

(87) PCT Pub. No.: WO2018/045199
PCT Pub. Date: Mar. 8, 2018

(65) Prior Publication Data

US 2019/0246632 A1 Aug. 15, 2019

Related U.S. Application Data

(60) Provisional application No. 62/381,881, filed on Aug. 31, 2016.

(51) Int. Cl.
*A61K 47/64* (2017.01)
*A01N 25/00* (2006.01)
(Continued)

(52) U.S. Cl.
CPC .......... *A01N 25/006* (2013.01); *A01N 25/08* (2013.01); *A01N 25/12* (2013.01); *A01N 57/08* (2013.01);
(Continued)

(58) Field of Classification Search
CPC .................................................. A61K 47/6455
See application file for complete search history.

(56) References Cited

U.S. PATENT DOCUMENTS 6,506,564 B1 1/2003 Mirkin et al.
2011/0196130 A1 8/2011 Lee et al.
(Continued)

FOREIGN PATENT DOCUMENTS

WO 2015080670 6/2015
WO 2016073548 5/2016

OTHER PUBLICATIONS

International Search Report and Written Opinion in corresponding PCT/US2017/049668, dated Nov. 27, 2017.
(Continued)

*Primary Examiner* — Benjamin J Packard
(74) *Attorney, Agent, or Firm* — Hovey Williams LLP

(57) ABSTRACT

Described herein are nucleic acid-peptide capsule complexes or nanoparticles comprising pre-formed peptide capsules and nucleic acids bound the exterior surface of the capsule, such that the wrap around the capsule membrane. The peptide capsules comprise bilayer membrane defining a liquid-receiving interior space and comprises a plurality of branched, amphipathic peptides. Method of making and using such complexes for delivering nucleic acids in vivo and in vitro are also described.

34 Claims, 24 Drawing Sheets

Specification includes a Sequence Listing.

bis(h9)K-K4
F.W. = 2652.7 bis(h5)K-K4
F.W. = 1912.3

(51) Int. Cl.
  *C07K 7/02* (2006.01)
  *C07K 14/00* (2006.01)
  *A61K 9/51* (2006.01)
  *A01N 25/08* (2006.01)
  *A01N 25/12* (2006.01)
  *A01N 57/08* (2006.01)

(52) U.S. Cl.
  CPC ........ *A61K 9/5146* (2013.01); *A61K 47/6455* (2017.08); *C07K 7/02* (2013.01); *C07K 14/001* (2013.01)

(56) References Cited

U.S. PATENT DOCUMENTS

| | | |
|---|---|---|
| 2012/0021020 A1 | 1/2012 | Tomich et al. |
| 2012/0316220 A1 | 12/2012 | Ward et al. |
| 2013/0164219 A1* | 6/2013 | Brinkmann ............ C07K 14/00 424/9.1 |
| 2014/0005379 A1 | 1/2014 | Gu |

OTHER PUBLICATIONS

Search Report in corresponding Canadian Application Serial No. 3,035,356, dated Feb. 6, 2020.

* cited by examiner

NUCLEIC ACID-PEPTIDE CAPSULE COMPLEXES

CROSS-REFERENCE TO RELATED APPLICATIONS

The present application is the U.S. National Stage of International Patent Application No. PCT/US2017/049668, filed Aug. 31, 2017, which claims the priority benefit of U.S. Provisional Patent Application Ser. No. 62/381,881, filed Aug. 31, 2016, entitled EFFECTIVE DELIVERY OF NUCLEIC ACIDS COMPLEXED WITH BRANCHED AMPHIPATHIC PEPTIDE CAPSULES, each of which is incorporated by reference in its entirety herein.

SEQUENCE LISTING

The following application contains a sequence listing in computer readable format (CRF), submitted as a text file in ASCII format entitled "SequenceListing," created on Aug. 31, 2017, as 5 KB. The content of the CRF is hereby incorporated by reference.

BACKGROUND OF THE INVENTION

Field of the Invention

The present invention relates to branched amphipathic peptide capsules complexed with externally-bound nucleic acids.

Description of Related Art

Nucleic acids have a number of therapeutic and prophylactic uses in both humans and non-human animals, as well as in the control and management of insect pests. However, stability of nucleic acids and effective modes of delivery continue to be a problem. Association of DNA with molecular carriers can increase the number of transfected cells and, consequently, the amount of in vivo expressed protein. Vaccinia virus and other poxviruses, retrovirus, adenovirus and herpes simplex virus are the most frequently used molecular carriers for DNA therapies and vaccines, particularly in gene therapy studies. Nonetheless, viruses present several drawbacks regarding large scale clinical applications including induction of dangerous inflammatory reactions, generation of immune responses to the viral vector and size limitation on the DNA that can be packaged. Likewise, entry of dsRNA into cells is the first step in one of the most useful tools in contemporary molecular biology: RNAi-based transcript knockdown. However, the dsRNA constructs has been administered primarily to insects by microinjection into hemolymph. While effective, this approach has its limitations, which include the tedium of repetitive injections and the difficulties in injecting smaller insect species (or earlier stages of development). Along with injections, methods such as soaking and ingestion have been explored but with limited success and reproducibility. Thus, the actual utility of RNAi for pest management is low and highly variable.

In previous studies, we have demonstrated that branched amphiphilic peptides (BAPs)-spontaneously co-assemble at room temperature to form bilayer delimited poly-cationic capsules (BAPCs) or vesicles having a liquid-receiving hollow core. These BAPCs are described in detail in U.S. Pat. No. 8,883,967, filed Mar. 26, 2010, incorporated by reference in its entirety herein. The BAPCs are readily taken up by cultured cells through the endocytic pathway, escape the late endosomes and ultimately accumulate in the perinuclear region, persisting there without apparent degradation. To date we have entrapped small proteins and solutes as well as stably encapsulated alpha particle emitting radionuclides within the BAPCs. However, attempts to encapsulate nucleic acid has not yielded effective results. Early attempts to encase DNA during the assembly of the monomeric branched peptides following the procedure designed for the encapsulation of small solutes failed. Larger molecules such as plasmid DNA prevented capsule formation, generating different, non-capsule structures depending on the peptide/DNA molar ratios. At high peptide/DNA ratios, excess peptide coated the plasmid surface, forming nano fibers (0.5-1 μm in length), while at low ratios, the peptides promoted DNA condensation into nano-sized spherical structures (100-400 nm). The elongated structures were not effective in transfecting cells.

Thus, there continues to be a need for effective approaches for delivering nucleic acids both in vitro and in vivo.

SUMMARY OF THE INVENTION

The present invention is broadly concerned with delivering nucleic acids using a stable peptide-based nano-carrier.

In one or more embodiments, nucleic acid-peptide capsule complexes are described herein, which comprise a peptide capsule comprising a bilayer membrane having an exterior surface and defining a liquid-receiving interior space, and a nucleic acid molecule bound to and extending lengthwise along the membrane exterior surface (in a face-to-face relationship, such that the nucleic acid may encircle or wrap around the capsule). The capsule membrane comprises a plurality of branched, amphipathic peptides, and each of the peptides comprises a C-terminal hydrophilic segment coupled to a branch point that is coupled to two respective N-terminal hydrophobic segments.

Also described herein are compositions comprising a plurality of nucleic acid-peptide capsule complexes, according to any of the described embodiments, dispersed in a pharmaceutically-acceptable carrier or excipient.

Methods of transfecting a cell are also described. The methods generally comprise incubating cells with a plurality of nucleic acid-peptide capsule complexes according to any of the described embodiments.

The present disclosure is also concerned with methods of preparing nucleic acid-peptide capsule complexes. The methods generally comprise mixing a plurality of peptide capsules with nucleic acid in a solvent system under ambient conditions and for a sufficient time period for the nucleic acid to bind to the peptide capsules through electrostatic interactions to yield the nucleic acid-peptide capsule complexes.

Also described herein are peptide capsule complexes for RNA interference of a target arthropod gene. The complex comprises a peptide capsules according to any of the described embodiments, and an arthropod RNA bound to and extending along the membrane exterior surface, wherein the RNA is complementary to at least a portion of mRNA of the target arthropod gene.

Methods of inhibiting a target gene in a target arthropod using RNA interference are also described. The methods comprise orally delivering a peptide capsule complex according to any of the described embodiments to the arthropod.

The present disclosure is also concerned with arthropod bait useful for oral administration of RNA for RNA interference in arthropods. The bait comprises a peptide capsule complex according to the described embodiments comprising arthropod RNA, and an edible arthropod attractant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 28 is a graph showing the stability of dsRNA in whole blood with and without BAPCs; and FIG. 29 is a graph showing the stability of FANA-RNAi in whole blood with and without BAPCs.

DETAILED DESCRIPTION

Figure 1:
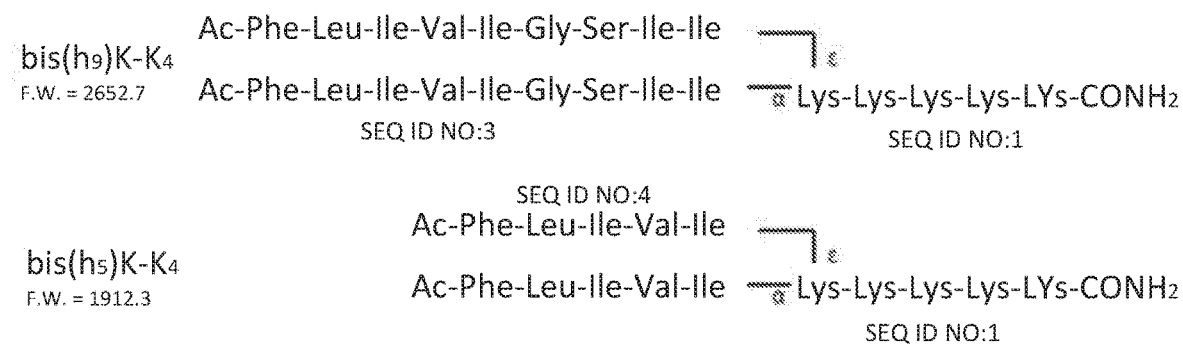
FIG. 1. is a schematic illustration of two different Branched Amphipathic Peptide Capsule (BAPC) Forming Sequences.

The present invention is concerned with branched amphiphilic peptide capsules (BAPCs) coated on their exterior surface with nucleic acids, each individually referred to herein as a nucleic acid-BAPC complex. Multiple complexes may aggregate together to form "clusters" comprising two or more nucleic acid-BAPC complexes.

Nano- and micro-structured capsules are contemplated herein, having a bilayer membrane formed from (comprising, consisting essentially or even consisting of) a plurality of branched (non-linear) amphiphilic peptides. Each of the peptides comprises a C-terminal hydrophilic segment ("head") coupled to a branch point, where the branch point is coupled to two respective N-terminal hydrophobic segments ("tails"). The peptides can either be of the all L-stereo configuration or D-stereo configuration. The peptides are amphipathic and comprise an oligo-lysine C-terminus with the alpha- and epsilon-amino groups of the N-terminal lysine acting as the branch points for two hydrophobic beta-sheet forming sequences. The resulting peptides, in their broadest terms, have a terminal hydrophilic (polar) segment, a branch point, and two terminal hydrophobic segments. Thus, the hydrophobic segments of the peptides are each preferably coupled to the same amino acid (lysine) residue which serves as the branch point attached to the hydrophilic segment, resulting in a terminal hydrophilic "head" and two terminal hydrophobic "tails," similar to the morphology of a class of lipids called diacylphospholipids.

The hydrophilic (polar) lysine head group sequences are preferably from about 1 to about 6 lysine residues in length, more preferably from about 2 to about 5 lysine residues, and even more preferably from about 3 to about 4 lysine residues. A particularly preferred lysine sequence is KKKK (SEQ ID NO: 1). The lysines will have a net positive charge at physiological pH values (7.2-7.4). A further uncharged N-terminal lysine residue is provided in the peptide as the branch point (—K—). Alternative branch points that could be used instead of lysine (—K—) include diaminopropionic acid, ornithine, diaminobutyric acid, and/or homolysine.

The branched hydrophobic sequences (or tails) are preferably each from about 3 amino acid residues to about 12 residues in length, and more preferably from about 4 to about 10 residues in length, and even more preferably from about 5 to about 9 residues in length. In one or more embodiments, the hydrophobic tails are derived from sequence information for an internal fragment of the human di-hydropyridine-sensitive L-type calcium channel segment CaIVS3 (DPWNVFDFLIVIGSIIDVILSE; SEQ ID NO: 2). In the CaIVS3 context, the peptide is part of a transmembrane helix that forms the central water-lined pore of a calcium channel. The hydrophobic segments of the peptide are synthetic versions of this sequence and are preferably selected from the group consisting of XLIVIGSII (SEQ ID NO: 3), XLIVI (SEQ ID NO: 4), and VFFIVIL (SEQ ID NO: 5), where X can be F, Y, W, or cyclohexylalanine. SEQ ID NO: 5 is a modified sequence loosely based on the CaIVS3 hydrophobic segment. All these branched sequences adopt a beta-sheet structure in water. In some embodiments, the N-terminal end of each hydrophobic tail can be capped with an acetyl group, $—NH_2$, naphthalene, fluorenylmethyloxycarbonyl, and/or anthracene.

It is particularly preferred that the peptides used to form the coating are selected from the group consisting of bis(h)-K—$K_n$, where h is a hydrophobic amino acid sequence selected from the group consisting of XLIVIGSII (SEQ ID NO: 3), XLIVI (SEQ ID NO: 4), and VFFIVIL (SEQ ID NO: 5), where X can be F, Y, W, or cyclohexylalanine; —K— is a branched lysine residue, K is a hydrophilic lysine residue, and n is from about 1 to about 6 (preferably from about 1 to about 5, and more preferably from about 1 to about 4). As noted above, the N-terminal end of each hydrophobic (h) sequence can be capped with an acetyl group (Ac), $—NH_2$, naphthalene, fluorenylmethyloxycarbonyl, and/or anthracene. Likewise, —K— can be replaced with diaminopropionic acid, ornithine, diaminobutyric acid, and/or homolysine.

The peptides preferably have a molecular weight ranging from about 781 Da to about 3345 Da, and more preferably from about 1116 Da to about 2999 Da, and even more preferably from about 1675 Da to about 2653 Da. The "molecular weight" for these peptides is an average weight calculated based upon the total MW of the actual amino acids present divided by the # of residues. The peptides preferably have an overall chain length ranging from about 7 amino acid residues to about 29 amino acid residues, more preferably from about 10 residues to about 26 residues, and even more preferably from about 15 residues to about 23 residues. Particularly preferred peptides are selected from the group consisting of bis($h_9$)-K—$K_4$, bis($h_5$)-K—$K_4$, and N-acetylated derivatives thereof, where $h_9$ is FLIVIGSII (SEQ ID NO:3) and $h_5$ is FLIVI (SEQ ID NO:4).

In one or more embodiments, functional groups and/or various moieties can be attached to the C-terminal lysyl epsilon amino head group or the C-terminal carboxyl group. The term "functional moiety" is used herein to encompass functional groups, targeting moieties, and active agents that may be attached to the outer surface of the peptide bilayer. Exemplary functional moieties that can be attached include fluorophores, dyes, targeting moieties and ligands, antibodies, cysteine, cysteamine, biotin, biocytin, nucleic acids, polyethylene glycol (PEG), organometallic compounds, (e.g., methyl mercury), radioactive labels, —COOH, $—CONH_2$, —SH, and the like. Multiple such moieties can also be attached in a chain of sequential order from the C-terminal head group (amino or carboxyl group) using aliphatic spacers to separate different moieties. Thus, the invention provides the opportunity to create multi-functionalized capsules with increased specificity and/or targeting capabilities. Since the individually modified peptides self-assemble to form the outer leaflet of the bilayer, any number of functional moieties can be adducted onto individual peptide sequences that comprise part of the assembled outer leaflet of the capsule membrane.

The peptides self-assemble into a capsule defined by the capsule membrane, which is preferably characterized by a bilayer morphology. The bilayer structure is characterized by an inner leaflet (or monolayer) and an outer leaflet (or monolayer). The inner leaflet presents an inner surface facing the intracapsular aqueous space (aka liquid-receiving interior space) of the capsule, the outer leaflet presents an outer surface facing the environment, where the bilayer membrane comprises a hydrophobic central region between the inner and outer surfaces. The inner and outer surfaces are characterized by hydrophilic head group regions of the peptides, while the hydrophobic central region is characterized by the interacting hydrophobic tail regions of the peptides. More preferably, the capsule membrane consists (or consists essentially) of a bilayer of peptides associating through hydrogen bonding, hydrophobic interactions, and Pi-Pi stacking of the aromatic residues. That is, the capsule membrane, although having a morphology similar to a lipid bilayer, is preferably substantially free of lipids, phospholipids, or detergents. As used herein the term "substantially free" with respect to the bilayer means that such segments are not embedded in the bilayer structure, which is preferably comprised entirely of peptides. It will be appreciated that although certain compounds or segments are preferably excluded from being embedded in the bilayer, they may be tethered to the surface of the bilayer, and in particular extend from the outer surface of the capsule membrane.

In one or more embodiments, the capsule membrane is heterogeneous, comprising at least two different peptides, preferably having different chain lengths. More specifically, the inner leaflet of the membrane bilayer comprises a plurality of a first amphipathic, branched peptide having a first number of amino acid residues, and the outer leaflet comprises a plurality of a second amphipathic, branched peptide having a second number of amino acid residues, where the first number of amino acid residues is different from the second number of amino acid residues. In one or more embodiments, the capsule membrane consists (or consists essentially) of alternating and interlocking sequences $bis(h_9)$-K—$K_4$ and $bis(h_5)$-K—$K_4$, or the N-acetylated derivatives thereof. More specifically, in some embodiments, the inner leaflet comprises (consists essentially or consists of) a plurality of $bis(h_5)$-K—$K_4$ peptides, while the outer leaflet comprises (consists essentially or consists of) a plurality of $bis(h_9)$-K—$K_4$ peptides.

In one or more embodiments, the capsule membrane is homogeneous, comprising a single peptide type (sequence) making up both the inner and outer leaflets, but nonetheless forming a bilayer. More specifically, the inner leaflet of the bilayer comprises a plurality of amphipathic, branched peptides having a first number of amino acid residues, and the outer leaflet comprises a plurality of amphipathic, branched peptides having a second number of amino acid residues, where the first number of amino acid residues is the same as the second number of amino acid residues. Thus, for example, in some embodiments, the inner leaflet comprises (consists essentially or consists of) a plurality of $bis(h_9)$-K—$K_4$ peptides, while the outer leaflet comprises (consists essentially or consists of) a plurality of $bis(h_9)$-K—$K_4$ peptides. Likewise, the inner leaflet may instead comprise (consists essentially or consists of) a plurality of $bis(h_5)$-K—$K_4$ peptides, while the outer leaflet comprises (consists essentially or consists of) a plurality of $bis(h_5)$-K—$K_4$ peptides. This homogenous bilayer is formed using the same procedures described for the heterogeneous capsule membrane, except that a single type of peptide is used for the peptide mixture, instead of adding a different type of peptide. Since the peptides are amphipathic, the same peptide type will nonetheless interact to create a similar bilayer morphology, as seen when using two different peptides according to the invention.

The method of forming the BAPCs comprises preparing a mixture of peptides in a solvent system. In one or more embodiments, the method comprises dissolving or dispersing a plurality of the first peptide and a plurality of the second peptide in an aqueous solution to form a heterogenous dispersion or solution of peptides, wherein the first peptide and second peptide are different (i.e., have different chain lengths). More preferably, the first peptide and second peptide are first dissolved or dispersed in a water miscible solvent to form respective organic solutions, which are then mixed together. Suitable water miscible solvents are selected from the group consisting of 2,2,2-trifluoroethanol (TFE), ethanol, methanol, tetrahydrofuran (THF), and acetonitrile, in water, with TFE being particularly preferred. In one aspect, the individual peptide solutions are prepared using a solvent comprising from about 40% v/v to about 100% v/v, and even more preferably about 100% v/v TFE. The peptides themselves can be synthesized using any suitable method, such as the 9-fluorenylmethoxycarbonyl (Fmoc) strategy using Fmoc-protected amino acids as described herein, followed by lyophilization until use.

The peptides in their individual solutions will preferably be observed to adopt a helical conformation, which can be confirmed by circular dichorism (CD) spectroscopy. The concentration of each peptide in their respective solutions will vary, but preferably ranges from about 0.001 mM to about 10 mM, more preferably from about 0.025 mM to about 7.5 mM, and even more preferably from about 1 mM to about 5 mM. The first peptide and second peptide (when present) are then preferably mixed at a molar ratio of from about 1:10 to about 10:1, more preferably from about 1:5 to about 5:1, and most preferably at about 1:1. As described in the working examples, the properties of the capsules can be varied by adjusting the relative amount of each peptide, or just using one type of peptide. The concentration of the first peptide in the combined solution preferably ranges from about 0.001 mM to about 10 mM, more preferably from about 0.01 mM to about 5 mM, and even more preferably from about 0.025 mM to about 2 mM. The concentration of the second peptide in the combined solution preferably ranges from about 0.001 mM to about 10 mM, more preferably from about 0.01 mM to about 5 mM, and even more preferably from about 0.025 mM to about 2 mM. The total concentration of the peptides in the solution will vary, but preferably ranges from about 0.001 mM to about 10 mM, more preferably from about 0.01 mM to about 5 mM, and even more preferably from about 0.025 mM to about 2 mM.

Regardless of the embodiment, once mixed, the solvent is then removed, preferably under vacuum, to produce a dried mixture comprising, and preferably consisting of, the first and second peptides (or just the first peptide for a homogenous capsule membrane). The dried peptide mixture preferably comprises less than about 10% by weight moisture, and more preferably less than about 5% by weight moisture, based upon the total weight of the dried mixture taken as 100% by weight. Put another way, the first and second peptides preferably comprise about 90% by weight of the dried mixture, and more preferably at least about 95% by weight of the dried mixture, based upon the total weight of the dried mixture taken as 100% by weight.

Once the solvent is removed, the dried peptide mixture is then rehydrated with water (preferably via dropwise addition) until the final desired concentration of each peptide dissolved in water is reached to form a capsule formation solution comprising the mixture of peptides. The concentration of the first peptide in the capsule formation solution preferably ranges from about 0.001 mM to about 10 mM, more preferably from about 0.01 mM to about 5 mM, and even more preferably from about 0.025 mM to about 2 mM. The concentration of the second peptide in the capsule formation solution preferably ranges from about 0.001 mM to about 10 mM, more preferably from about 0.01 mM to about 5 mM, and even more preferably from about 0.025 mM to about 2 mM. The total concentration of the peptides in the capsule formation solution will vary, but preferably ranges from about 0.001 mM to about 10 mM, more preferably from about 0.01 mM to about 5 mM, and even more preferably from about 0.025 mM to about 2 mM. Preferably, the peptides are rehydrated using distilled deionized (DDI) water. The pH of the solution can be adjusted using a dilute solution of NaOH (0.005% w/v), so that it ranges from about 4 to about 9, more preferably from about 5.5 to about 8.5, and even more preferably from about 6 to about 8. Any compounds to be encapsulated in the capsules (e.g., dyes, active agents, small enzymes, antimicrobial agents, radionuclides, anti-cancer and apoptogenic agents, etc.) are also added to the capsule formation solution at the desired levels. The capsule formation solution is then allowed to stand under ambient conditions at room temperature (~25° C.) for at least about 30 minutes, and more preferably from about 30 minutes to about 3 hours. In one or more embodiments, the capsule formation solution is then incubated for at least about 1 hour at a reduced temperature (about 4° C.) to stabilize the capsules, followed by returning the capsule formation solution to room temperature for at least about 30 minutes. Stable capsules can also be prepared by incubating the mixtures at either 4° C. or 37° C. for at least about 60 minutes. The prepared capsules are then dried under vacuum for storage and subsequent use.

Unlike existing peptide vesicles, which adopt a helical secondary structure, the inventive peptides will preferably be observed to adopt a beta-sheet secondary structure in capsule membrane formation. In the bilayer morphology, the peptides interact to form a beta sheet structure in the hydrophobic central region. The term "beta-sheet" conformation or structure, as used herein, refers to secondary protein structure where the protein forms overlapping layers, thus forming a beta-pleated sheet. Such beta-pleated sheets in the invention reside in a "parallel orientation" (i.e., the N-termini of successive strands are oriented in the same direction).

In one or more embodiments, the resulting individual capsules have a particle size of less than about 200 nm, preferably less than about 150 nm, more preferably less than about 100 nm, and even more preferably less than about 70 nm, with a preferred size range of from about 5 nm to about 65 nm (even more preferably from about 10 nm to about 50 nm). As used herein, the "particle size" refers to the maximum surface-to-surface dimension of the body, such as the diameter in the case of substantially spherical bodies. Notably, although water moves freely across the capsule membrane, drying the capsules does not lead to their collapse and the encapsulated solution (and any solutes) remain encapsulated in the intracapsular space of the capsules, even after drying. Another important aspect of the capsules is the cationic nature of the solvent-exposed surface of the capsule membrane bilayer. This property makes them readily taken up by cells, helps them escape the endosome transport pathway as well as provides an ideal surface for negatively charged nucleic acids to bind to through electrostatic forces.

The resulting capsules can be prepared for targeting to specific cell surface receptors through adduction of the C-terminal lysine with different molecules or functional groups (functional moieties), such as cholesterol, mannose, TAT peptide, insulin, biotin, nucleotides, or any other suitable known surface targeting molecules, active/therapeutic agents, and combinations thereof. The targeting moieties can be conjugated to the hydrophilic segment of the outer layer of the bilayer membrane, thus presenting the targeting moiety on the exterior surface of the capsule after formation. The moiety will be recognized by the targeted region or tissue in the patient, and the capsule will automatically localize in that region or tissue.

In one or more embodiments, the capsules can be used to deliver nucleic acids (e.g., DNA or RNA) in vivo or in vitro. Instead of attempting to encapsulate the nucleic acids within the capsule for delivery, the nucleic acids instead associate with and encircle or wrap around the outside of the capsules (it being understood that a nucleic acid molecule is still considered to "encircle" the capsule even if its length does not permit it to completely wrap around the capsule body). That is, in this invention, the nucleic acids are not merely tethered to the capsule (or individual peptide) at one end (with the other end extending away from the capsule). Rather, the nucleic acids are bound to the membrane exterior surface through electrostatic interactions along the length of the nucleic acid chain (and specifically through negatively charged moieties, e.g., phosphate groups, along the nucleic acid backbone). Thus, the nucleic acids extend adjacent and along the membrane in a face-to-face relationship with the membrane exterior surface. A variety of types of nucleic acid molecules (oligomers) can be used in the invention, including, without limitation, plasmid DNA, mRNA, dsRNA, ssRNA, microRNA, RNAi, FANA-RNAi molecules, and combinations thereof. Ideal nucleic acid molecules will have a length of less than about 100,000 nucleotides (total length, i.e., 50,000 base pairs), and preferably from about 20 to about 50,000 nucleotides.

To prepare the nucleic acid-BAPC complexes, the prepared capsules are reconstituted in an aqueous solution containing dissolved nucleic acid oligomers. The nucleic acid solution is then added, preferably dropwise, to the BAPCs solution and sufficiently mixed to ensure dispersion of the nucleic acids throughout the BAPCs solution. The concentration of nucleic acid in the resulting solution preferably ranges from about 10 pM to about 1 mM, more preferably from about 100 pM to about 100 µM, and even more preferably from about 10 nM to about 1 µM. The concentration of BAPCs in the resulting solution preferably ranges from about 1 µM to about 10 mM, more preferably from about 10 µM to about 5 mM, and even more preferably from about 100 µM to about 1 mM. In one or more embodiments, the ratio of phosphate groups in the nucleic acids to lysine nitrogens in the BAPCs in solution preferably ranges from about 1:1 to about 1:100, and more preferably from about 1:5 to about 1:20. The solution is allowed to stand under ambient conditions for about 10 minutes, preferably from about 30 to about 60 minutes, to allow the nucleic acid to complex with the BAPCs in solution. In one or more embodiments, calcium chloride is then added to the solution at a level of about 1 mM, to further condense or compact the nucleic acid in the complexes (further decreasing their size) and tie up any free nucleic acid that may yet have associated with a BAPC.

Depending upon the amount of nucleic acid used in comparison to the amount of BAPCs, different kinds of complexes can be formed. For example, in one or more embodiments, each complex can comprise a single BAPC encircled with nucleic acid molecules. The complexes will preferably have a particle size of from about 10 nm to about 250 nm, more preferably from about 10 nm to about 200 nm, even more preferably from about 10 nm to about 100 nm, and most preferably from about 20 nm to about 70 nm.

In one or more embodiments, the nucleic acid can interact with and/or wrap around more than one BAPC to create clusters. Clusters can also be created from multiple individual nucleic acid-coated BAPCs aggregating together after complex formation. Clusters may range in size from about 30 nm to about 250 nm, and preferably from about 50 nm to about 200 nm. Regardless, the resulting nucleic acid-BAPC complexes or clusters can then be dried, lyophilized for storage and subsequent use, or used directly in solution. Thus, it will be appreciated that the present invention provides a distinct advance in the state of the art regarding DNA vaccines, wherein the DNA can be stored in a dried/lyophilized state at room temperature, until it is reconstituted in aqueous solution for use in vaccination protocols. Thus, the complexes can be provided in dried form as part of a kit, along with appropriate aqueous solution for creation of vaccines on-site.

Thus, the nucleic acid-BAPCs complexes can be used in pharmaceutically-acceptable compositions for delivering nucleic acids and can be administered orally, intravenously, subcutaneously, intramuscularly, nasally, intraocularly, transdermally, intraperitoneally, or aerosolized to a subject. As used herein, the term "pharmaceutically-acceptable" means not biologically or otherwise undesirable, in that it can be administered to a subject, cells, or tissue, without excessive toxicity, irritation, or allergic response, and does not cause any undesirable biological effects or interact in a deleterious manner with any of the other segments of the composition in which it is contained. In one or more embodiments, the composition is orally active. Advantageously, the capsule membrane is resistant to high temperatures, chaotropes, and nucleases. Moreover, the invention does not require any additional treatments or protocols to further stabilize and/or protect the nucleic acid bound to the BAPCs.

In one or more embodiments, the composition comprises a therapeutically-effective amount of nucleic acid-BAPCs complex dispersed in a pharmaceutically-acceptable carrier or excipient. A pharmaceutically-acceptable carrier or excipient would naturally be selected to minimize any degradation of the nucleic acid-BAPCs complexes, functional groups, or attached active gents, and to minimize any adverse side effects in the subject, cells, or tissue, as would be well known to one of skill in the art. Pharmaceutically-acceptable ingredients include those acceptable for veterinary use as well as human pharmaceutical use. Exemplary carriers and excipients include aqueous solutions such as normal (n.) saline (~0.9% NaCl), phosphate buffered saline (PBS), and/or sterile water (DAW), oil-in-water or water-in-oil emulsions, and the like. As used herein, a "therapeutically effective" amount refers to the amount of the supramolecular assemblies that will elicit the biological or medical response of a tissue, system, animal, or human that is being sought by a researcher or clinician, and in particular elicit some desired therapeutic effect. For example, in one or more embodiments, a therapeutically effective amount of the nucleic acid-BAPCs complex is an amount that delivers sufficient nucleic acid to the subject or site of interest. Notably, the nucleic acid-BAPCs complexes have a significantly increased efficiency in delivery of the nucleic acids. Thus, the dosage amounts of nucleic acid loaded onto the BAPCs and delivered to the subject can be dramatically decreased compared to standard dosage amounts, because more of the nucleic acid is actually delivered to the cells. Moreover, the increased stability of the nucleic acid-BAPCs complexes means that the effective amounts may remain circulating in vivo for sustained periods of time in some embodiments. One of skill in the art recognizes that an amount may be considered therapeutically effective even if the condition is not totally eradicated but improved partially.

In one or more embodiments, the nucleic acid-BAPCs complexes in solution can be mixed with food or a food additive for oral delivery of the nucleic acids. In one or more embodiments, the solution is mixed with the food or food additive, followed by drying the mixture. In one or more embodiments, the dried nucleic acid-BAPCs complexes are mixed with the food or food additive. In one or more embodiments, the nucleic acid-BAPCs complexes are added to a liquid-based feed. It will be appreciated that this approach is particularly advantageous for delivering nucleic acids (such as for RNAi) for oral ingestion by a variety of chewing and/or sucking arthropods in larval and/or adult stages. Examples include, without limitation, mosquitoes, beetles, caterpillars, cockroaches, locusts, termites, aphids, psyllids, ants, ticks, fleas, flies, spiders, and combinations thereof. For example, the complexes can be incorporated into an insect bait with an edible insect attractant in a form selected from the group powder, liquid, gel, self-sustaining gel-matrix, tablet, granular, and combinations thereof.

In one or more embodiments, the nucleic acid-BAPCs complexes can be used to transfect cells with the nucleic acid. The complexes are incubated with the cells under appropriate cell culture conditions, whereupon the complexes are taken up by the cells and the nucleic acid is incorporated.

As noted, the nucleic acid-BAPCs complexes are particularly advantageous for DNA vaccines.

The nucleic acid-BAPCs complexes can also be used to indirectly deliver the nucleic acid to an organism, such as a blood sucking pest. For example, the nucleic acid-BAPCs complexes may comprise nucleic acids targeted for an arthropod pest (e.g., for RNAi or other nucleic acid based inhibition of pest function). The nucleic acid-BAPCs complexes can be administered to a mammal, wherein the complexes remain circulating in the blood stream of the mammal. It is contemplated that a pest (e.g., tick, flea, flies, etc.) feeding on the mammal will ingest the nucleic acid-BAPCs complexes. Depending upon the mode of action, the nucleic acids will cause phenotypic changes in the pest, resulting in e.g., mortality, increased susceptibility to insecticide, decreased mobility, decreased fertility, or decreased ability to proliferate, etc. Thus, such methods can be used to inhibit or control a pest infestation and decrease pest damage.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these

Example 1

Introduction

The present study used Branched Amphiphilic Peptide Capsules (BAPCs) composed of two branched peptides: bis(Ac-h$_9$)-K—K$_4$ and bis(Ac-h$_5$)-K—K$_4$ derived from a human transmembrane channel sequence. These peptides are described in detail in U.S. Pat. No. 8,883,967, incorporated by reference herein in its entirety. These self-assembling peptides form hollow vesicles or capsules in water displaying a uniform size of ~20-30 nm that can trap solutes during the capsule formation process. The term "capsule" is preferentially used herein in an effort to avoid confusion between solid, peptidic nano-spheres and traditional lipid vesicles. The core of the capsules is hollow and the interior space is filled with fluid (and other solutes) used either for capsule formation or reconstitution of the capsules. In addition to small solutes, BAPCs can also encapsulate proteins, such as cytochrome c and RNase A. The peptides are mixed as helical monomers in the absence of water, dried and then hydrated to start the annealing process. BAPCs formation is observed after 30 min with nascent capsules assembling into sizes ranging from 20-30 nm in diameter. "Conformationally constrained" 20-30 nm BAPCs are prepared using temperature shifts during the annealing process and referred to as "locked" nano-capsules. If the peptides are assembled at 25° C. the nascent capsules undergo fusion and within a few hours form heterogeneous spherical structures that ranged in size (50-200 nm). BAPCs formed at 25° C. and then moved to 4° C. for as little as one hour blocked fusion even when they were returned to elevated temperatures (up to 80° C.). BAPCs prepared at either 4° C. or 37° C. do not undergo fusion and retain the size of the nascent capsules. This work utilized a 1:1 ratio of the two peptides bis(Ac-h$_5$)-K—K$_4$—CO—NH$_2$ and bis(Ac-h$_9$)-K—K$_4$—CO—NH$_2$ (FIG. 1). This ratio was chosen initially to allow enough of the smaller peptide to line the inner leaflet with the larger sequence making up the outer leaflet of the assembled bilayer to compensate for any strain due to curvature. In this study, the resulting BAPCs act as nucleation centers for the DNA molecules that coat the surface of the peptide capsules.

In this work, plasmid DNA associates with the surface of the BAPCs. Under these conditions, the negatively charged DNA interacts with the cationic surface of the BAPCs through numerous electrostatic interactions generating peptide-DNA complexes (aka nanoparticles or nanocapsules) with sizes ranging from 50 to 250 nm. The BAPCs-DNA nanoparticles are capable of delivering different sized plasmid DNA into cells in culture, yielding high transfection rates and minimal cytotoxicity. Furthermore, BAPCs were tested for in vivo delivery of a DNA vaccine previously designed to activate immune responses and capable of controlling tumors induced by type 16 human papilloma virus (HPV-16). The BAPCs-DNA nanoparticles enhanced the vaccine-induced antitumor protection and promoted efficient activation of murine dendritic cells. Mice vaccinated with DNA-coated BAPCs delayed tumor growth without detectable acute toxicity but at a peptide:DNA ratio different than that observed for optimal in vitro cell transfection. The complexes were able to activate mouse dendritic cells and showed clear immunomodulatory effects. In summary, the results presented here indicate that BAPCs-DNA nanoparticles provide a less cytotoxic and efficient non-viral DNA/gene delivery approach for in vitro and in vivo applications.

Materials and Methods

Peptide Synthesis.

Figure 2:
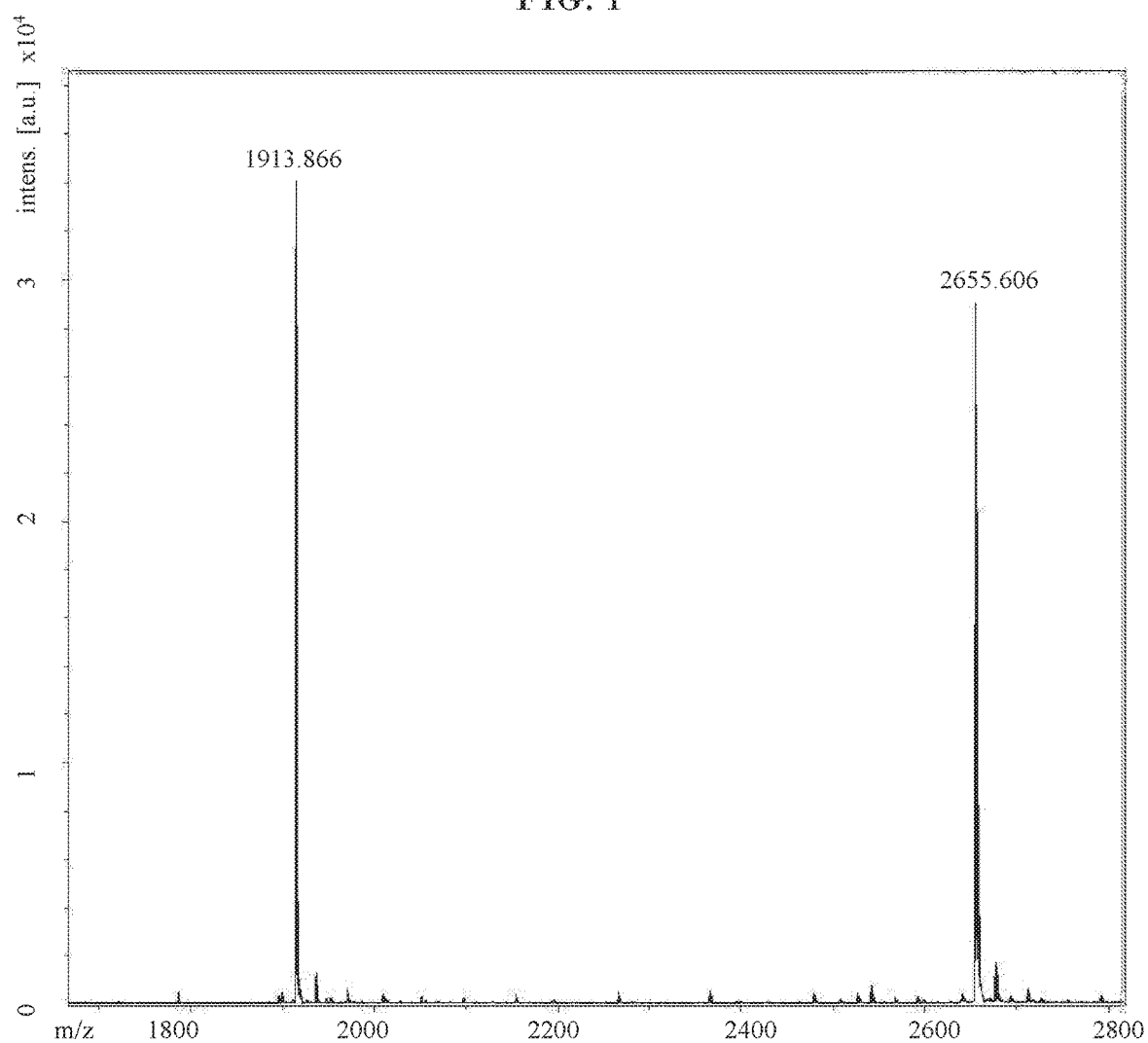
FIG. 2 is a MALDI-MS spectrum of BAPCs Prepared from Purified Peptides.

The peptides bis(Ac-h$_9$)-K—K$_4$ and bis(Ac-h$_5$)-K—K$_4$, were synthesized and cleaved as described in U.S. Pat. No. 8,883,967, incorporated by reference, and then lyophilized before storing at room temperature (RT). The cleaved peptides were purified by reversed phase HPLC and characterized using matrix-assisted laser desorption ionization-time of flight (MALDI-TOF) mass spectrometry (Ultraflex II, MALDI TOF/TOF, Bruker Daltronics, Billerica Mass.). The masses were determined for the pure peptides after BAPC assembly as shown in FIG. 2.

"Conformationally Constrained" BAPC Nanoparticle Preparation.

The peptides, were dissolved individually in pure 2,2,2,-Triuoroethanol (TFE) and their concentrations determined based on the absorbance of the phenylalanines at 258 nm. Final concentrations of 500 µM were then prepared before removing the solvent under vacuum. Under these condition the peptides remain as monomers during the drying process. Water was added drop-wise to the dried peptide mixture and allowed to stand for 30 min at 25° C. to form the water-filled nanocapsules. Subsequently, the solution was cooled to 4° C., and incubated for 1 h prior to returning them to room temperature for an additional 30 min. This protocol yields the conformationally constrained BAPCs (20-30 nm), which are resistant to disassembly in the presence of organic solvents. The peptide capsules were prepared in water (salt/buffer-free) to optimize the electrostatic interactions between the poly-anionic DNA and the cationic surface of the capsules. BAPCs prepared using other assembly temperature regimes do not work well in delivering nucleotides.

Preparation of DNA-BAPCs Nanoparticles.

For all peptide-DNA complex preparations, different (N:P) charge ratios were tested. For instance, 1 mL of a 20 µM peptide concentration contains $1.20 \times 10^{16}$ peptide molecules. There are 4 lysines positively charged, therefore $1.20 \times 10^{16}$ (4)=$4.80 \times 10^{16}$ NH$_3^+$(N). In the case of DNA, 2.5 µg of 4.7 kb ds plasmid in 1 mL contains $4.94 \times 10^{11}$ ds plasmid molecules (Average M.W. of a DNA basepair=650 daltons), considering the phosphate molecules, $4.94 \times 10^{11}$ ($2 \times 4,700$)=$4.67 \times 10^{15}$ PO$_4^-$(P). Therefore, $4.80 \times 10^{16}/4.67 \times 10^{15}$ yields a N:P of 10.4. For the in vitro transfection experiments size-stabilized BAPCs were added to a pEGFP-N3 or pCMV-SD95-21-GFP plasmid solutions at the suitable (N:P) for each cell line. The plasmid pEGFP-N3 (4.7 Kb) was obtained from Dr. Dolores Takemoto (Clontech, Mountain View, Calif.) and pCMV-SD95-90 21-GFP (19.4 Kb). Solutions were mixed carefully with a pipette and allowed to stand for 10 min at RT before adding CaCl$_2$, 1.0 mM final concentration. After an additional 30 min incubation period, the solution was added to the cell culture. CaCl$_2$, alone at this concentration was analyzed and did not to enhance DNA uptake or expression.

STEM sample preparation. For transmission electron microscopy (TEM) DNA-BAPC nanoparticles were prepared as previously described prior to placing the sample on the TEM grid. The samples were negatively stained using a multi isotope 2% Uranyl acetate (Uranium bis(acetato)-O-dioxodihydrate) (Sigma-Aldrich, St. Louis, Mo.) aqueous solution. Sample solutions (6 µL) were spotted on to grids and allowed to air dry before loading it into the FEI Tecnai F20XT Field Emission Transmission Electron Microscope (FEI North America, Hillsboro, Oreg.).

Atomic Force Microscopy (AFM).

Peptide-DNA samples, were deposited onto freshly cleaved mica substrates. After 15 min of incubation, the sample was dried under nitrogen. AFM topography images of immobilized BAPCs-DNA complexes were acquired in air using the contact mode on an Innova Atomic Force Microscope (AFM) from Bruker, USA. The AFM scanner was calibrated using a TGZ1 silicon grating from NT-MDT, USA. MLCT-E cantilevers with their respective nominal spring constants of 0.05 N/m and 0.1 N/m were used, with set point contact forces of 1 nN or less. The AFM topography data were attained by subtracting background then using a second order line by line fitting methods incorporated within the Gwyddion software.

Determination of Zeta Potential.

The different N:P BAPCs-DNA complex ratios were prepared as previously described. Particle size and zeta-potentials and for all samples were determined using a Zetasizer Nano ZS (Malvern Instruments Ltd, Westborough, Mass.). Samples were analyzed in $CaCl_2$ 1 mM and all measurements were performed in triplicates.

In Vitro Plasmid Transfection.

HeLa and HEK-293 cells were purchased from ATCC (CCL-2). For transfection experiments, $1 \times 10^5$ cells were seeded on 22 mm culture dishes; 24 h later at 60% confluence, all medium was removed from the wells and 800 μL of Opti-MEM® I Reduced Serum Media was added. Next, for HeLa cells 200 μL BAPCs-DNA nanoparticles at N:P ratios of 1.3, 2.6, 5.2, 10.4, 20.8 and 26 were added to cells. These N:P ratios correspond to peptide concentrations of 2.5, 5, 10, 20, 40 and 50 μM respectively mixed with 2.5 μg of pEGFP-N3. For HEK-293 cells, BAPCs-DNA nanoparticles corresponding to N:P ratios of 6.5, 13, 26 and 52 (12.5, 25, 50 and 100 μM respectively), were mixed with 2.5 μg of pCMV-SD95-21-GFP) and added to cells. They were then incubated under normoxic conditions for 2-6 h. After the incubation period, media and transfection reagent were removed and replaced with 1 mL of fresh DMEM containing 10% FBS in each well. The cells were returned to the incubator for 48 h. For the positive control, cells were transfected with Lipofectin® (Invitrogen, Carlsbad, Calif.), with adjusted conditions for optimal results in each cell line. Lipoplexes for HeLa cells were formed in 200 μL of OptiMEM® I serum medium mixing 2.5 μg of pDNA with 8 μL of the transfection reagent. For HEK-293, 2.5 μg of DNA was mixed with 12 μL of the cationic lipid. The lipoplexes were added to the cells and allowed to incubate for 6 h at 37° C. After this incubation period, media and transfection reagent were replaced with 1 mL of fresh DMEM containing 10% FBS in each well. The cells were returned to the incubator for 48 h. Transfection efficiency was monitored by confocal microscopy and quantified by fluorescence activated cell sorting (FACS), FACSCalibur (Becton Dickinson, Grayson, Ga.). Propidium iodide (PI) was used to identify and then exclude dead cells from the analysis. Non transfected cells containing only BAPCs were used as a control. Data were analyzed using the FlowJo software V.10.1 (TreeStar, Oreg., USA).

Confocal Laser Scanning Microscopy.

Images were obtained using a confocal LSM 700 laser-scanning microscope (Carl Zeiss, Gottingen, Germany).

Cell Viability Assay In Vitro.

Cell viability was monitored by flow cytometry using the cell death exclusion PI. For HeLa cells cell viability was also analyzed using exclusion of the fluorescent dye trypan blue. $1 \times 10^5$ HeLa cells were seeded on 22 mm culture dishes; 24 h later at 60% confluence, all medium was removed from the wells and 800 μL of Opti-MEM® I Reduced Serum Media was added. Next, 200 μL BAPCs-DNA nanoparticles with N:P ratios=1.3, 2.6, 5.2, 10.4, 20.8 and 26, mixed with 2.5 g of were added to cells and allowed to incubate under normoxic conditions for 2-6 h. After this incubation period, media and nanoparticles were removed and replaced with 1 mL of fresh DMEM containing 10% FBS in each well. The cells were returned to the incubator for 48 h before performing the analysis. The Lipofectin® (Invitrogen, Carlsbad, Calif.) control was used according to the protocol previously mentioned Mice.

Female C57BL/6 mice at 8-10 weeks of age were supplied by the Faculty of Veterinary Medicine and Animal Science and housed at the Microbiology Department of the University of Sao Paulo. All procedures involving animal handling and treatment followed the recommendations for the proper use and care of laboratory animals from the University of Sao Paulo Ethics Committee.

DNA vaccine and immunization regimens. The plasmid DNA vaccine (5.6 kb, pgDE7 plasmid) used in these experiments encode type 16 human papilloma virus (HPV-16) E7 oncoprotein genetically fused to HSV-1 gD protein (pgDE7). Pre-assembled conformationally-constrained BAPCs were added to an aqueous DNA solution containing 40 μg of the plasmid DNA vaccine, using 400, 800 and 3200 μM of BAPCs to achieve N:P ratios of 1.3, 2.6, and 10.4 respectively. Each animal was inoculated with a final volume of 100 μL intramuscularly divided in 50 μL aliquots and applied into the tibialis anterior muscle of each mouse hind limb. The immunization was carried out 3 days after subcutaneous transplantation of $7.5 \times 10^4$ TC-1 cells, which express the HPV-16 E7 oncoprotein. The TC-1 tumor cells were suspended in 100 μL of serum-free medium and injected into the left rear flank of the animals. Tumor development was checked by visual inspection and measured using a digital caliper twice a week for a period of 70 days. The animals were scored as tumor-bearing when the tumors reached a size of approximately 2 mm in diameter. Survival rates were based on the percentage of animals with tumor volumes reaching up to 1000 $mm^3$ according to the formula: ½ (length×width) or 15 mm of length.

Intracellular Cytokine Staining (ICS).

Intracellular IFN-γ staining was performed using blood samples collected 14 days after the vaccine administration. The blood samples were treated for lysis of red blood cells and cultured at a concentration of $10^6$ cells/well for 6 hr at 37° C. in 96-well round bottom microtiter plates with 10 μg/mL of Brefeldin A (GolgiPlug; BD Biosciences, CA, USA) in the presence or not of 3 μg/mL of the E7-specific RAHYNIVTF (SEQ ID NO:6) peptide antigen sequence (amino acids 49-57). After incubation, the cells were stained with BB515-conjugated anti-CD8a antibody and after fixation and permeabilization, with PE-labeled anti-IFN-γ. The buffers and antibodies were purchased from BD Biosciences (CA, USA). The cells were examined by flow cytometry using a FACS Fortessa (BD Biosciences) and the data were analyzed using FlowJo software (TreeStar, Oreg., USA).

Activation of Mouse Dendritic Cells (DC) In Vitro.

Spleens and lymph nodes from naïve C57BL/6 mice were collected, carefully macerated and washed with ice-cold MACS buffers (PBS, 0.5% bovine serum albumin, 2 mM EDTA). Large particulate matter was removed by passing the cell suspension through a cell strainer 70 μm nylon membrane. After suspended in MACS buffer cells were incubated with MicroBeads (Miltenyi Biotec) conjugated to hamster anti-mouse CD11c monoclonal antibodies according to the manufacture's protocols. Positively selected DCs containing >90% CD11c+ cells were stimulated for 48 h with PBS, DNA (10 µg of pgDE7) and LPS at 100 ng/mL as a final medium concentration. Also, CD11c+ cells were stimulate at the same conditions with the BAPCs-DNA nanoparticles at N:P charge ratio of 1.3 using 10 µg of pgDE7 and BAPCs at 100 µM and an additional group containing only uncoated BAPCs at 100 µM as a final concentration (BAPCs). Then, the tested substances and stained with anti-CD11c+ cells were stained with, anti-I-A [b] (anti-MHCII), anti-CD40, anti-CD80 and anti-CD86 conjugated to different fluorochromes (BD Biosciences). The cells were examined by flow cytometry using FACS LSR Fortessa (BD Biosciences) and data were analyzed using the FlowJo software V.10.1 (TreeStar, Oreg., USA).

Cytometric Bead Array (CBA).

The cytokines levels in supernatants of dendritic cell cultures were measured after 48 h of stimulation using the CBA kit 200 Th1/Th2/Th17 (BD Biosciences) for the quantification of IL-2, IL-4, IL-6, INF-, TNF-$\alpha$, IL-17A and IL-10 according to the manufacturer's instructions. In summary, the sample and the cytokine kit standards were mixed with microspheres coated with capture antibodies specific for the respective cytokines. Then, samples were incubated with the detection antibody labeled with phycoerythrin (PE) for 2 h at room temperature in the dark. The flow cytometry analysis was based on the fluorescence intensity using FACS Fortessa (BD Biosciences). Data were analyzed with the aid of the FCAP Array 3.0 to determine the concentration (pg/mL) and means of fluorescence intensities (MFI) of the samples and standards.

In Vivo Toxicity Assay.

Blood samples were collected individually from the submandibular plexus of mice 1 or 7 days after the immunization. Sera were obtained after centrifugation at 5,000 g at 4° C. for 30 min and measured for aspartate (AST) and alanine (ALT) transaminases (Laborclin, SP, and Brazil), lactate dehydrogenase (LDH), urea and creatinine (Wiener lab, Argentina) levels using commercial assay kits according to the manufacturer's protocols.

Results

Preparation and Characterization of BAPCs-DNA Nanoparticles.

BAPCs preparation begins by mixing two peptides, bis($h_9$)-K—$K_4$ and bis($h_5$)-K—$K_4$, at equimolar concentration in 2,2,2-Trifluoroethanol (TFE). In this solvent the peptides are monomeric, adopting a helical conformation, and do not aggregate. Once combined, the solvent is removed under vacuum and samples are then hydrated to form capsules of desired concentration by the dropwise addition of water. The capsules are kept for 30 min at 25° C. to reach a stable size of 20-30 nm, subsequently they are incubated at 4° C. for 1 h and then rewarmed to 25° C. thereby fixing their size (20-30 nm). The solution is allowed to stand at 25° C. for an additional 30 min before adding the dsDNA. Nanocapsules prepared in this fashion have a stable structure that remains unaffected by solvents, salts, chaotropes or temperature. The cationic lysine residues exposed on the outer surface of BAPCs bind electrostatically to the repeating negatively charged phosphate groups present in DNA. Transmission electron microscopy (TEM) images revealed a complete, uniform coating of a single BAPCs surface with what appears to be a double strand DNA (FIG. 3A) or in clusters (FIG. 3B), confirming that a multi-molecular process should exist where more than one BAPC and most likely one DNA plasmid molecule are involved in the supra-molecular structure of the nanoparticles.

Figure 3:
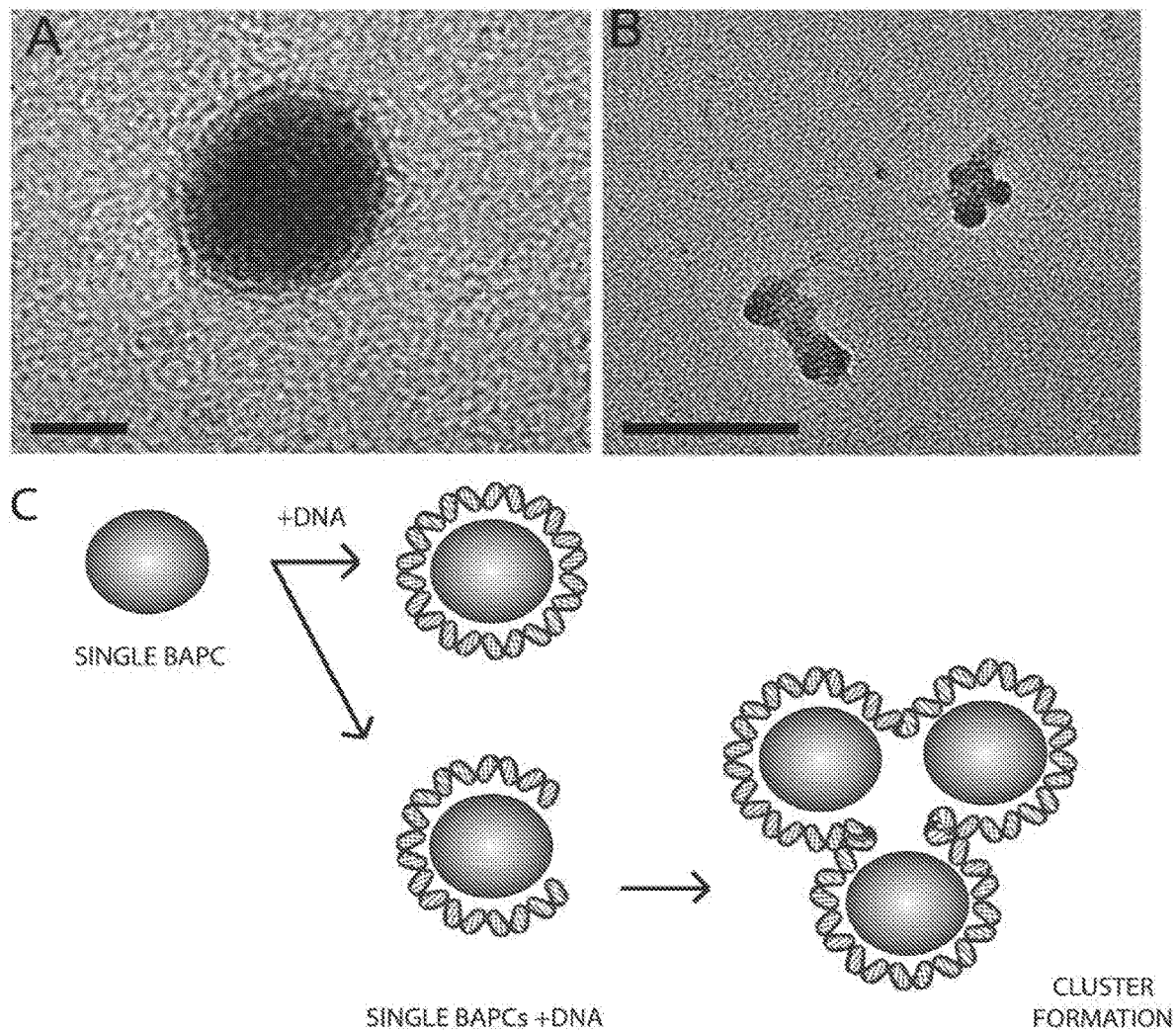
FIG. 3 shows (A) a TEM image of a BACP:DNA nanoparticle at N:P=20.8 showing a single BAPC interacting with pDNA. Scale bar=10 nm; (B) a TEM image of a cluster of BAPCs interacting with DNA. Scale bar=100 nm; and (C) Schematic illustration of BAPC-DNA interactions.
Figure 4:
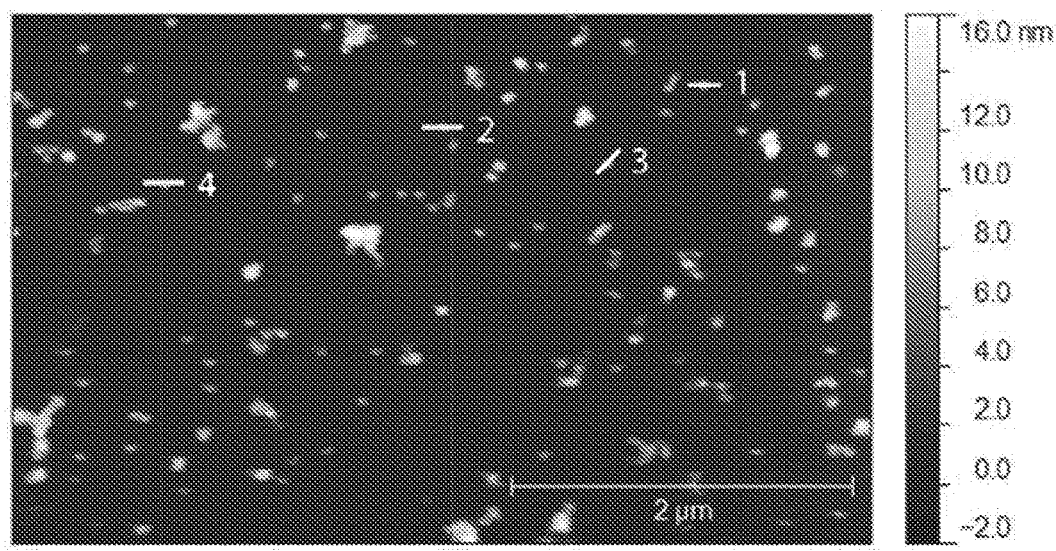
FIG. 4 shows AFM image analysis of the BACP-DNA nanoparticles at N:P=20.8. (A) 5×3 µm image of the nano-structures formed; and (B) Cross sectional analyses of the numbered nano-structures shown in (A)
Figure 4:
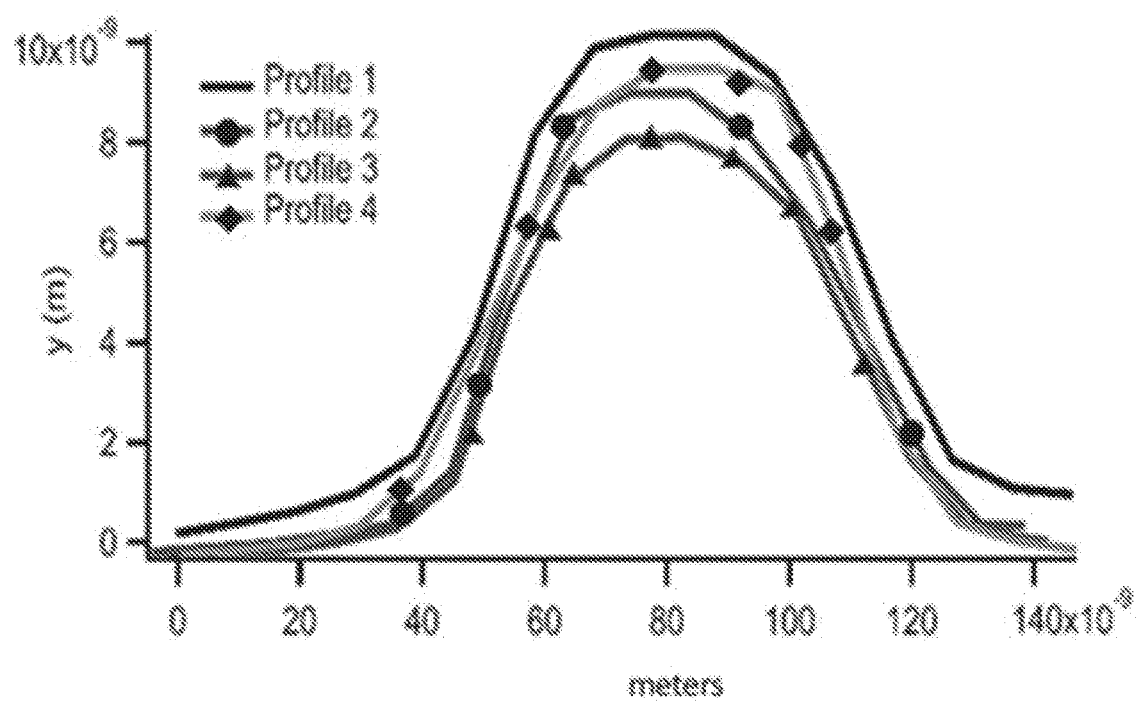

A dried supercoiled 4.7 kb plasmid DNA visualized with atomic force microscope (AFM) showed an estimated size of ~400 nm. However, free soluble DNA molecules generally adopt much larger sizes. For a single 20-30 nm BAPC, the curvature may be too high for a DNA chain to wrap tightly however, since the bending energy is inversely proportional to the square of the bending circle radius, bending of DNA around larger nanoparticle clusters requires much lower energies. This might explain the presence predominantly of clusters with average size between 100 and 250 nm. The presence of both single and clustered BAPCs-DNA nanoparticles indicates that the DNA can assume several modes of associating with the BAPCs or that the assembly process may not have gone to completion. The single BAPC-DNA nanoparticles may be intermediates rather than endpoints (FIG. 3C). AFM was also used to confirm the topologies of the BAPCs-DNA nanoparticles. We observed clusters with average size between 100-250 nm and single BAPCs-DNA complexes with particle size distribution between 50-80 nm—values in agreement with those obtained using TEM (FIG. 4A-B).

Based on the two different imaging techniques, BAPCs mixed with DNA form compact clusters with sizes ranging on average from 50 to 250 nm. Among several parameters such as particle shape, rigidity, surface properties and degradability, particle size is known to play an important role for intracellular uptake and subsequent transfection efficiency. Nanoparticles with a size of 50 nm have been previously reported to be taken up 34 times faster than 100 nm particles and 810 times faster than 500 nm particles. Thus, BAPC-DNA nanoparticles appear to fit into a suitable size range compatible with the in vitro cellular uptake.

Figure 5:
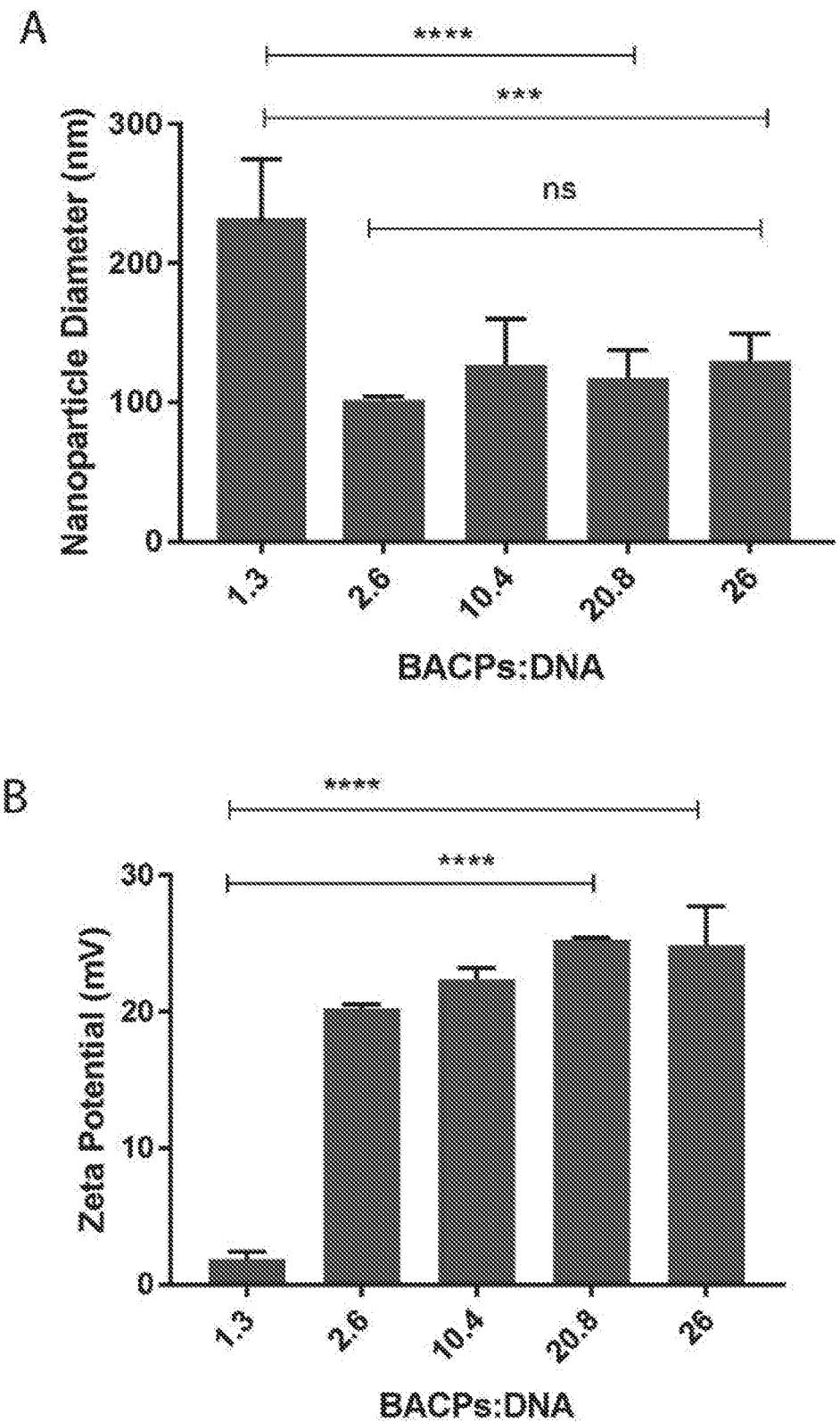
FIG. 5 shows the (A) Dynamic light scattering (DLS) size (z-average); and (B) zeta potential data for different BAPCs-DNA formulations.

To further evaluate the biophysical properties of the BAPCs-DNA nanoparticles, we measured the particle size and zeta potential of several formulations by dynamic light scattering (DLS). We analyzed the BACPs-DNA complexes at different (N:P) charge ratios. The N:P charge ratio for a given complex is defined as the number of protonated amino groups ($NH_3^+$) contained in the tetra-lysine portion of the branched peptides (even though not all are present on the outer surface of the BAPCs) and the number of charged phosphates ($PO_4^-$) present in the plasmids used. Formulations with N:P ratios of 2.6, 10.4, 20.8 and 26 displayed an average size of ~150 nm. A slight increase in size was observed for the N:P=1.3 (~250 nm). (FIG. 5A). These results are in accordance to the particle size observed in TEM and AFM. The zeta potential (ZP) of the nanoparticles increased at higher peptide concentrations demonstrating the efficient neutralization of the DNA in all the tested formulations (FIG. 5B). Positive ZP's improve cellular uptake. HeLa cells in suspension have been reported to have very low resting potentials (from −15 to −44 mV) and supports the notion that the negative charge of the DNA needs to be sufficiently neutralized for efficient uptake. Data are based on three independent experiments (n=9). Differences between values were compared by ANOVA using Bonferroni as post-test. Statistical significance: (*) p<0.001; (**) p<0.0001. Non-statistical significance (ns) was considered when P>0.05.

In Vitro Transfection Efficiency of BAPCs Coupled with dsDNA.

Figure 6:
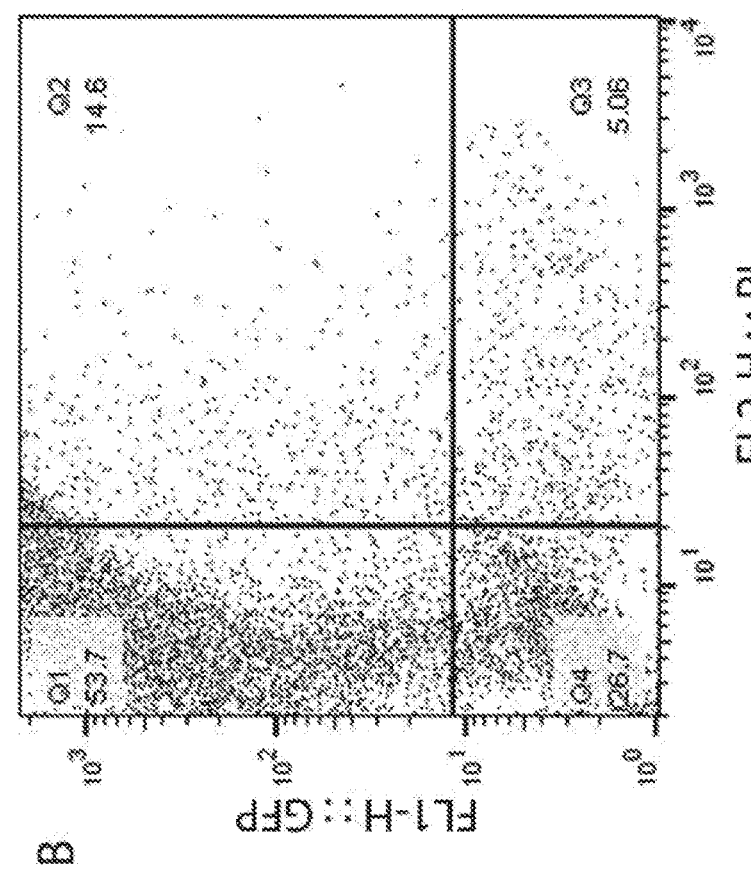
FIG. 6 shows (A) a graph of in vitro transfection efficiency in HeLa cells of BAPCs-DNA nanoparticles prepared at different peptide:DNA charge ratios (N:P) an incubation time of 4 h in reduced serum media and 1 mM $CaCl_2$); (B) Flow cytometry analysis of GFP-expressing HeLa cells after 48 h post transfection with BAPCs nanoparticles at N:P ratio 20.8; (C) a graph of in vitro transfection efficiency in HEK-293 cells of nanoparticles prepared at different peptide:DNA charge ratios (N:P) an incubation time of 4 h in reduced serum media and 1 mM CaCl2; and (D) Flow cytometry analysis of GFP-expressing HEK-293 cells after 48 h post transfection with BAPCs nanoparticles at N:P ratio of 26.
Figure 6:
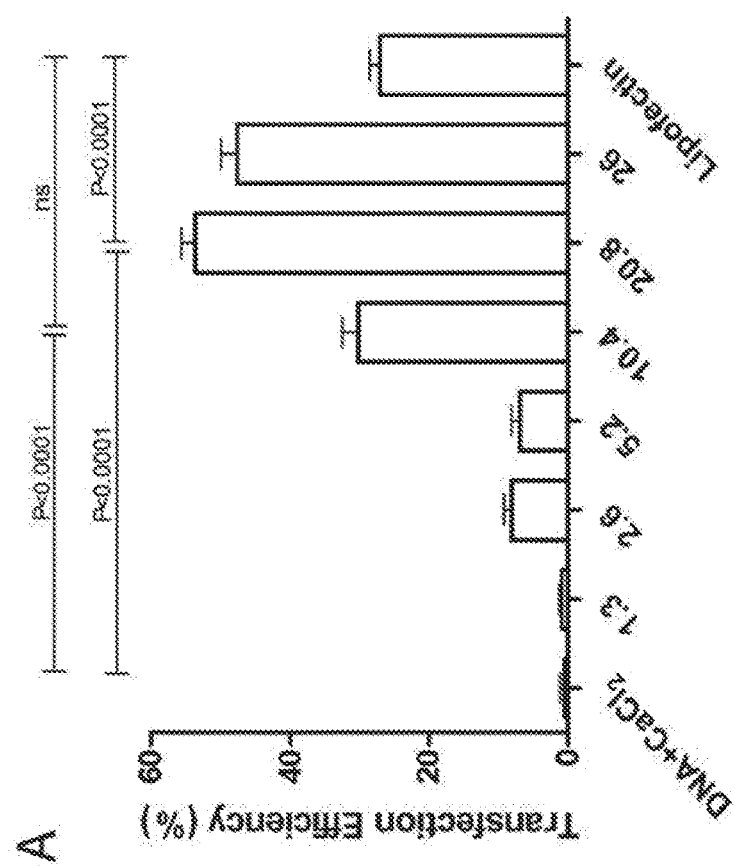
Figure 6:
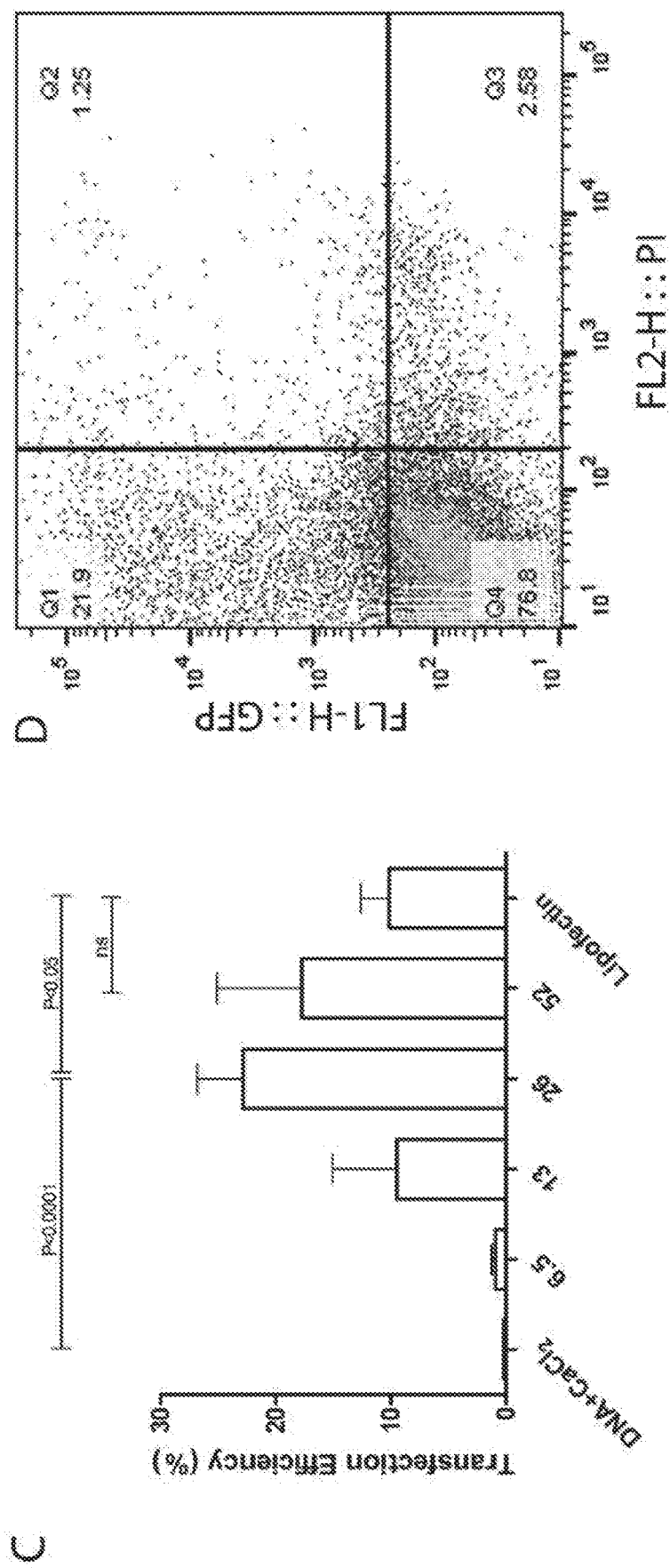
Figure 7:
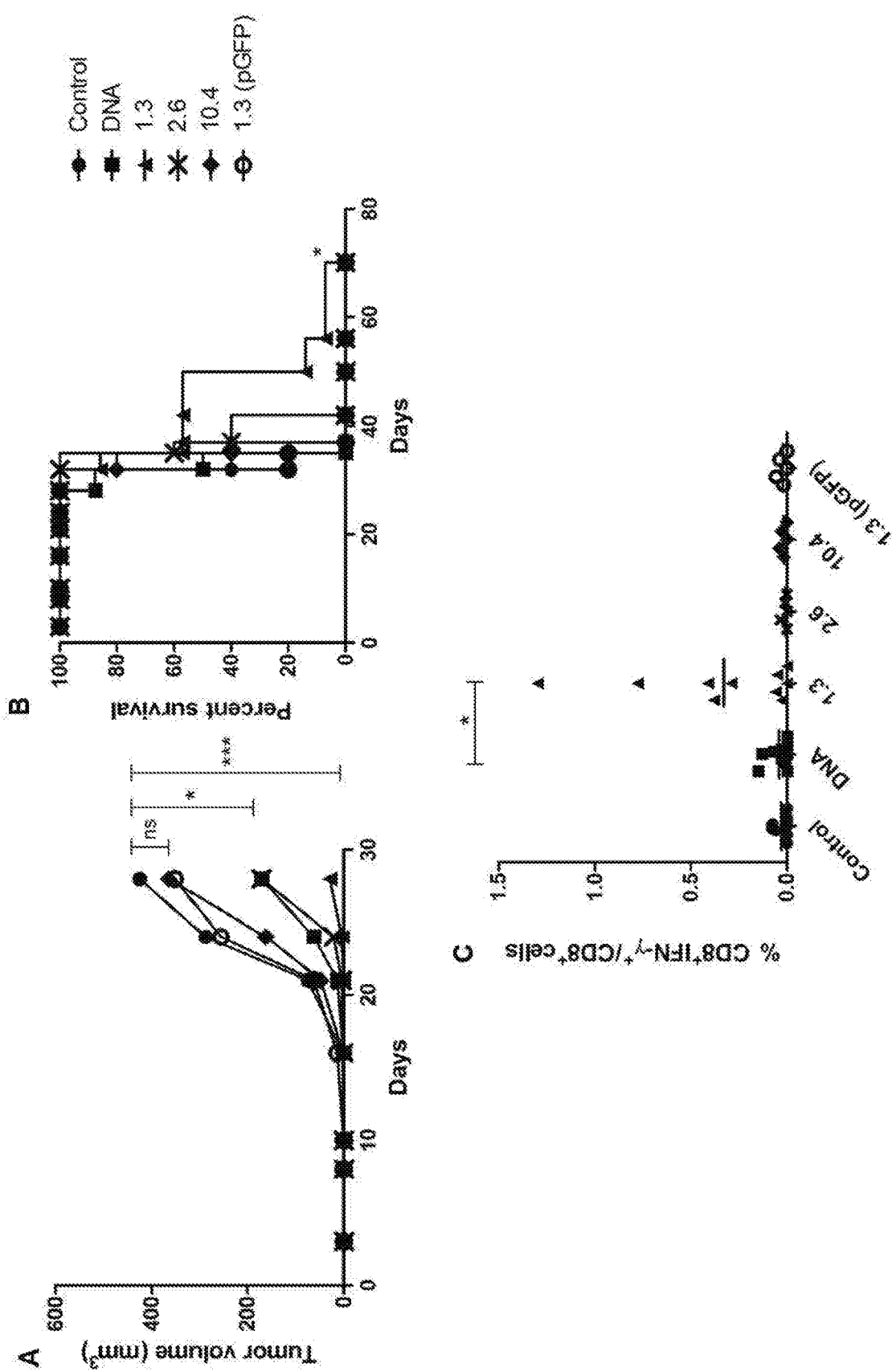
FIG. 7 shows the results of the Antitumor effect and survival curves of mice immunized with BAPCs-DNA nanoparticles at different N:P ratios, (A) a graph of Mean values of tumor size ($mm^3$) progression±SD values until day 30; (B) a graph of Survival rates within 70 days after the TC-1 injection; and (C) a graph of intracellular IFN-γ staining of CD8+ T lymphocytes after in vitro stimulation with E7-derived MHC-I-specific peptide of peripheral blood mononuclear cells (PBMCs) monitored by flow cytometry and expressed as percentage of CD8+IFN-γ+ cells of total CD8+ T cells.

The ability of nano-sized BAPCs to deliver plasmid DNA in vitro was assessed by incubating cells with peptide-DNA nanoparticles at different N:P ratios. HeLa cells were incubated with the BAPCs-DNA complexes for 4 h in Opti-MEM® I Reduced Serum Media at N:P ratios ranging from 1.3 to 41.6. The ratios that showed the highest transfection efficiencies were 10.4, 20.8 and 41.6 yielding values of (30.29%+/−1.59, 50.12%+/−2.5, and 47.55%+/−1.65) respectively. To determine the influence of the incubation time on N:P ratios 10.4 and 20.8, HeLa cells were also incubated with the BAPCs-DNA complexes for periods ranging from 2 h to 12 h. Optimal rates were obtained with incubation times of 4 and 6 h. Different buffers were also evaluated in the absence and presence of $CaCl_2$ (1 mM). Addition of $CaCl_2$ (1 mM) promoted a small, but not statistically significant, increase in the number of transfected cells over those incubated with the nanoparticles in the absence of the salt. Maximal transfection rates (~55%) for HeLa cells were achieved using DNA-complexed to BAPC nanoparticles at a N:P ratio of 20.8 and an incubation time of 4 h with cells kept in Opti-MEM® I Reduced Serum Media containing 1 mM of $CaCl_2$ (FIG. 6A-B). We subsequently tested the ability of BAPCs to deliver larger plasmids; pCMV-SD95-21-GFP (19.4 kB) into a different cell line (HEK-293). For this cell line, the highest transfection rates (~25%) were achieve using a N:P ratio of 26 with an incubation time of 4 h with cells kept in Opti-MEM® I (FIG. 6C-D). Data represent mean values±SD (standard error of the mean) of three experiments combined. Differences between values were compared by ANOVA using Bonferroni as post-test. Non-statistical significance (ns) was considered when P>0.05.

Figure 8:
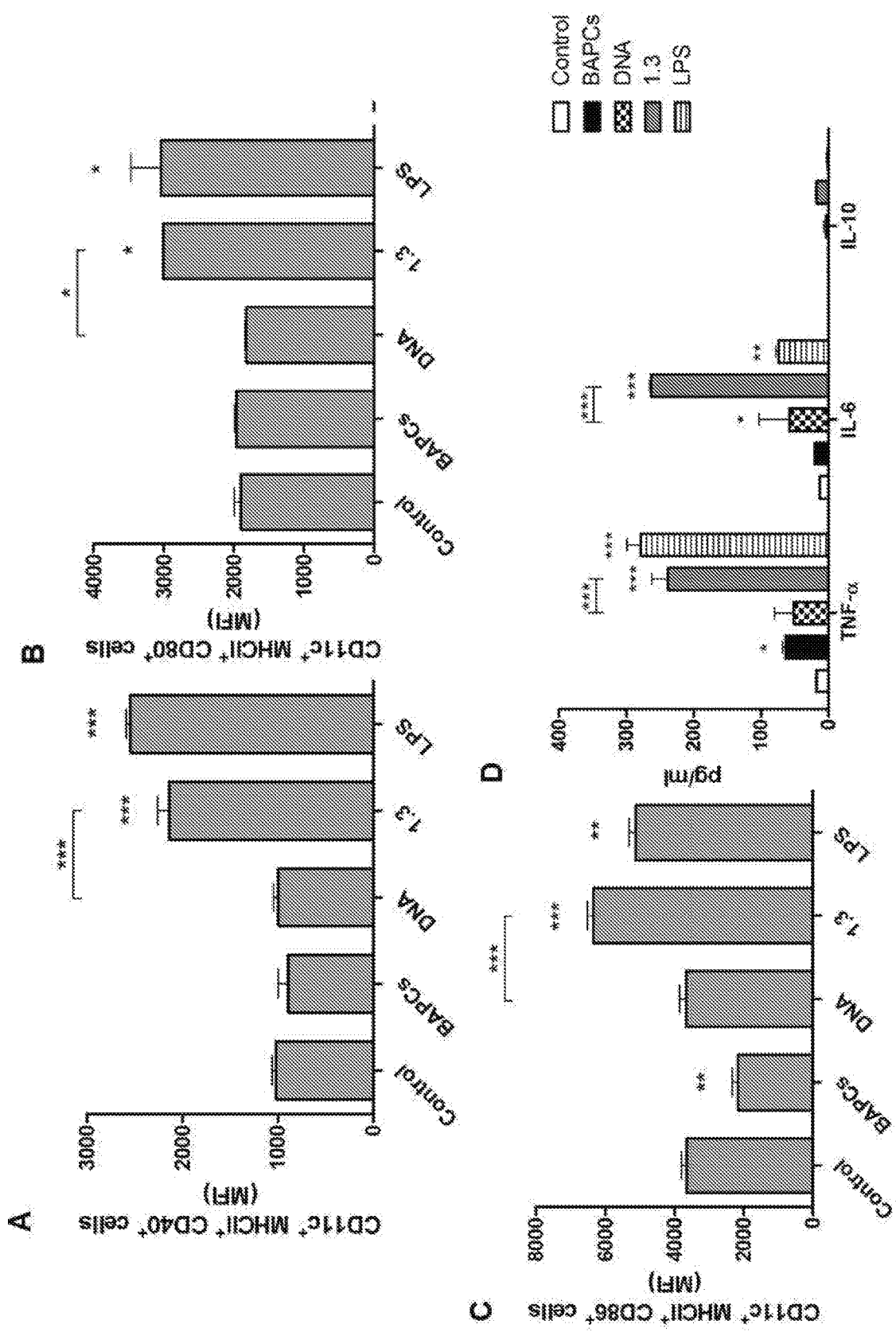
FIG. 8 shows surface expression levels of activation markers measured by flow cytometry after gating in CD11c+ (PE) MHCII+ (FITC) cells shown as Median Fluorescence Intensity (MFI) bar graphs of (A) CD40; (B) CD80; and (C) CD86 (APC) markers; and (D) TNF-α, IL-6 and IL-10 cytokine induction (pg/ml) in cell culture supernatants.
Figure 9:
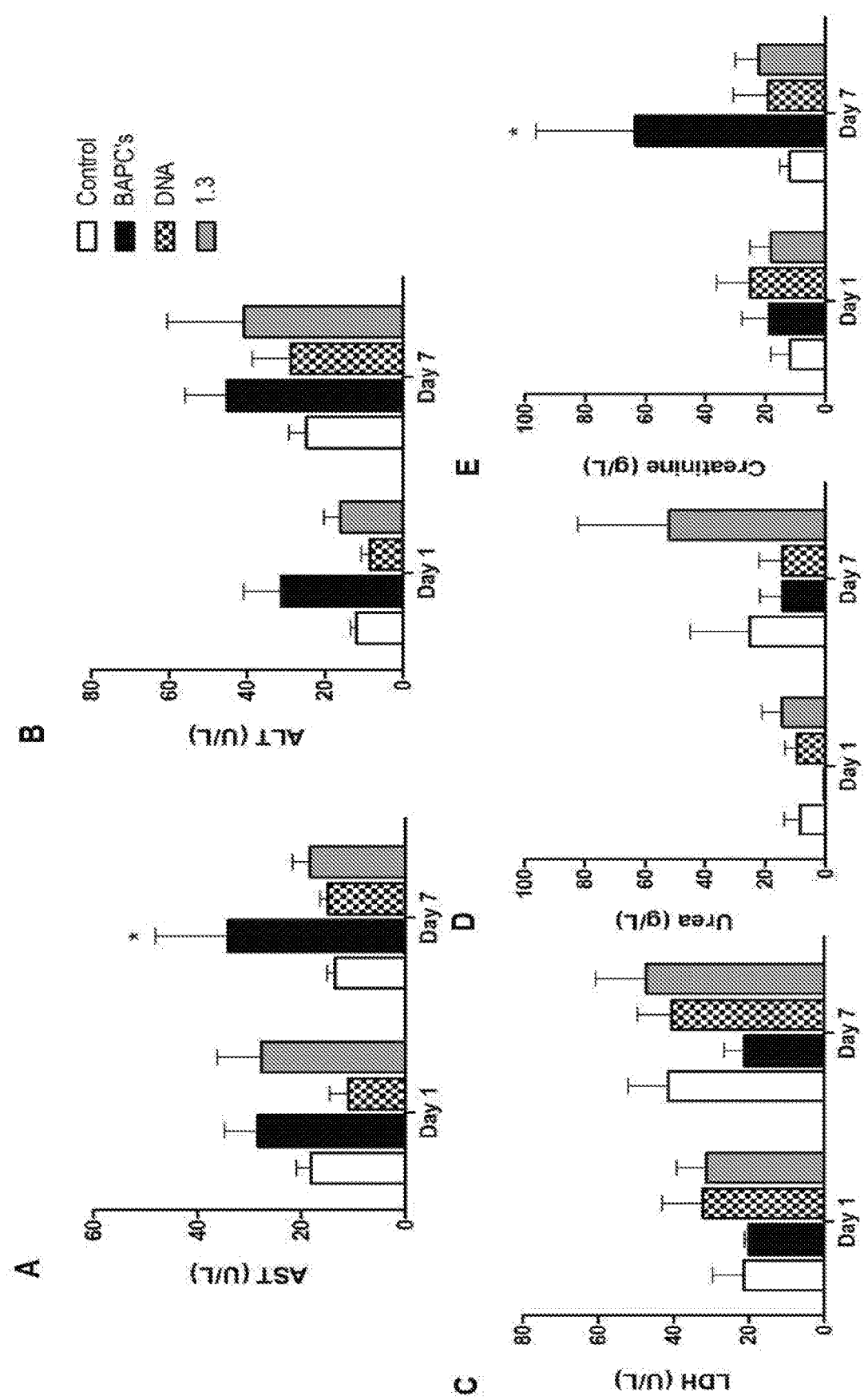
FIG. 9 shows the results of toxicity analysis of sera collected from mice 1 and 7 days post inoculation for the presence of: (A) AST transaminase; (B) ALT transaminase; (C) LDH; (D) urea; and (E) creatinine.

The plasmid pCMV-SD95-21-GFP encodes the entire genome for the North American type I porcine and reproductive syndrome virus (PRRSV). Successful delivery and expression of this plasmid resulted in the shedding of competent RNA virus. This result indicates that BAPCs could find application in delivering vaccines derived from cDNA of attenuated virus thus eliminating the need for large production of protein inoculants. As a positive control, cells were transfected with the commercial reagent Lipofectin® using conditions optimized for each cell line. Quantification of the transfection efficiencies were monitored using fluorescence activated cell sorting (FACS). Propidium iodide (PI) was used to identify and then exclude dead cells from the analysis. Additionally, the in vitro cytotoxicity of the BAPCs-DNA nanoparticles was also evaluated in HeLa cells based on cell death entry of trypan blue. The results showed that cell viability is minimally affected at the N:P ratio that produced the highest transfection efficiency while for the lipid-based transfection reagent, up to 40% of the cells did not survive the treatment. Confocal microscopy showed normal morphologies for those cells that were treated with BAPCs-DNA nanoparticles whereas those treated with Lipofectin® displayed abnormal cell structures.

In Vivo Delivery of a DNA Vaccine Encoding an HPV-16 Oncoprotein.

After evaluating the transfection efficiency and toxicity of the DNA-coated BAPCs in vitro, we tested the nano-sized complexes ability to deliver DNA in vivo. For that purpose, we tested a DNA vaccine that encodes the HPV-16 E7 oncoprotein (pgDE7). This vaccine has shown control in the proliferation of tumor cells expressing HPV-16 oncoproteins (TC-1 cells) grafted in C57BL/6 mice. The pgDE7 plasmid was incubated with conformationally constrained BAPCs at N:P ratios of 10.4, 2.6 and 1.3. The complexed BAPCs-DNA were inoculated intramuscularly in mice, 3 days after inoculation of the TC-1 tumor cells. The negative control group was represented by non-vaccinated mice. Other control groups received only naked pgDE7 plasmid and BAPCs complexed with a plasmid that does not encode pgDE7, to ensure that the anti-tumor protection is induced by the pgDE7 (FIG. 7A). Mice immunized with BAPCs coated with pgDE7 at N:P ratios higher than 2.6 did not efficiently control tumor growth. The 2.6 ratio showed similar protection level compared with the group treated with naked pgDE7. BAPCs-DNA nanoparticles at N:P ratio of 10.4, which demonstrated enhanced transfection efficiency compared to DNA alone, displayed tumors that reached the size of ~1.0 cm, almost 30 days after transplantation of TC-1 cells, showing no statistical difference between the non-vaccinated (control) mice and the 1.3 pGFP group (40 μg, negative control). In contrast, mice immunized with DNA-coated BAPCs at N:P of 1.3 with pgDE7 constrained the tumor growth up to one month after transplantation of the TC-1 cells. In addition, the survival time was enhanced by two-fold in comparison to that observed in the non-complexed DNA group (FIG. 7B). Immunization with BAPCs coated with pgDE7 at 1.3 N:P ratio also enhanced the number of E7-specific cytotoxic lymphocytes with regard to mice immunized with the same amount of DNA vaccine but not complexed with BAPCs (FIG. 7C). Data are based on three independent experiments (n=10) Statistical significance: (*) p<0.05; (***) p<0.001 versus DNA group or as indicated by bars. (A, C) t-test; (B) Log-rank (Mentel-Cox) test.

Is noteworthy that only the 1.3 N:P ratio showed the least positive zeta potential value (2 mV) compared to the other preparations (FIG. 5B). These results might be associated with very low cytotoxicity and little or no tendency for aggregation promoting higher gene expression of the pDNA in vivo, as observed with other nanoparticles presenting neutral zeta potential. The particle size range obtained by DLS (~250 nm) for this formulation is comparable to previous reports on particles for DNA vaccine delivery.

Mouse DC Activation by BAPCs-DNA Nanoparticles.

We have also analyzed the capacity of BAPCs-pgDE7 complexes to activate antigen presenting cells (APCs), a key cell type involved in the activation of T cell responses which are directly responsible of controlling tumor growth in different mouse models, such as the transplantation of TC-1 cells. Dendritic cells ($3\times10^5$ cells) from naïve mice lymphoid organs were incubated for two days with PBS (control), only BAPCs at 100 μM, DNA (10 μg of pgDE7), BAPCs-DNA nanoparticles at N:P charge ratio of 1.3, and LPS (100 ng/ml). The surface expression levels of activation markers were measured by flow cytometry after gating in CD11c+ (PE) MHCII+ (FITC) cells shown as Median Fluorescence Intensity (MFI) bar graphs of CD40, CD80 and CD86 (APC) markers. Data represent mean values±SD of two experiments combined. Statistical significance: (*) p<0.05, () p<0.01, (*) p<0.001 versus Control group or as indicated in the bars (ANOVA, Bonferroni post-test)

Particulate carriers are known to enhance the immunogenicity of DNA vaccines by facilitating uptake by APCs, such as dendritic cells (DCs). Indeed, particles up to 500 nm are efficiently engulfed by DCs and result in activation of cytotoxic lymphocytes capable of recognizing and lysing tumor cells. DCs isolated from spleen of naïve C57BL/6 mice were incubated with the pgDE7-BAPCs and the expression of surface co-stimulatory receptor molecules (CD40, CD80 and CD86) was measured. Under our experimental conditions, DCs incubated with BAPCs-pgDE7 complexes showed augmented expression of co-stimulatory molecules, reaching similar levels as those observed after incubation with bacterial lipopolysaccharide (LPS), a potent activator of DCs (FIG. 8A-C). In contrast, no activation of co-stimulatory molecules was detected on DCs exposed to naked plasmid DNA or BAPCs not associated with DNA (FIG. 8A-C), which ruled out the possible effects associated with LPS contamination in DNA and BAPCs preparations. Moreover, DCs stimulated with the pgDE7-BAPCs secreted enhanced amounts of the pro-inflammatory cytokines TNF-α and IL-6 that promote APC maturation and activation of cells involved in the adaptive immune response. In contrast, the production of IL-10, a suppressive cytokine associated with the activation of tolerogenic APCs, while moderately enhanced in the supernatants of DCs stimulated with BAPCs-DNA nanoparticles, showed levels approximately 10-fold lower than those observed for TNF-α and IL-6, displaying a cytokine balance shifted towards a pro-inflammatory environment (FIG. 8D). DCs stimulated with the same amount of pgDE7 or BAPCs alone were not affected as evaluated by the secretion of any of these cytokines. Our results indicate that coupling a plasmid DNA vaccine with BAPCs promote activation of DCs and, therefore, better prepared for the subsequent activation of cytotoxic T lymphocytes (CTL). CTL, particularly $CD8^+$ T cells, are key components of the immune system in controlling tumors. Importantly, the secretion of TNF-α and IL-6, in combination with reduced secretion of immune suppressive cytokines (IL-10) by APCs may affect activation of $CD8^+$ T lymphocytes as well as macrophages and natural killer cells, that also play relevant roles on the control of tumor cells growth.

In Vivo Toxicity Assay of BAPCs-DNA Nanoparticles.

To test the in vivo toxicity of BAPCs coated with DNA, C57BL/6 mice were inoculated intramuscularly with naked DNA (40 µg of pgDE7), BAPCs-pgDE7 nanoparticles at N:P ratio of 1.3 and only BACPs (without the pgDE7 plasmid) at 400 µM. The sham-treated group (control) received PBS. Individual sera were collected at day 1 or 7 after the immunization and analyzed for the presence of aspartate (AST) and alanine (ALT) transaminases, urea, creatinine and lactate dehydrogenase (LDH), which are recognized as markers of liver, kidney or general tissue damages. The results are shown in FIGS. 9A-E. Data represent mean values±SD of three experiments combined (n=10). Statistical significance: (*) $p<0.05$ versus Control group (ANOVA, Bonferroni post-test). Only mice treated with free BAPCs showed increased AST and creatinine serum levels with regard to the control group. In contrast, none of the other tested biochemical markers were increased in mice immunized with the BAPCs-DNA nanoparticles up to 7 days after administration. DNA delivery systems based on nanoparticles, including gold-based nanomaterials and DNA-liposome complexes, often induce in vivo toxic effects, which vary accordingly to the dimensions and surface chemistry of the particles. Nonetheless, our results demonstrate that the DNA-coated BAPCs at N:P=1.3 do not show detectable systemic toxicity and, thus, may be compatible with in vivo applications.

Discussion

Here we report the ability of DNA-BAPC nanoparticles to safely deliver plasmid DNA both in vitro and in vivo. In vitro, DNA-BAPCs nanoparticles transfected cells in culture with higher efficiency than that observed with a popular lipid-based commercial product and with less cytotoxicity. In vivo, they induce immune modulatory effects leading to enhancement of the anti-tumor effects of a DNA vaccine in a murine model. The pre-complexed peptide nanoparticles, (~20-30 nm in diameter), were pre-formed in water at room temperature and subsequently incubated at 4° C. and then returned to RT. This protocol yields the conformationally constrained nanoparticles that are completely resistant to disassembly in organic solvents. BAPCs prepared using other temperature regimes did not perform as well in delivering dsDNA in vivo. Comparable to how histones compact DNA to form nucleosomes, the conformationally constrained BAPCs interact with plasmid DNA acting as a cationic nucleation centers with the negatively charged DNA coating the outer surface, generating peptide-DNA nanoparticles with sizes ranging between 50-250 nm. HeLa cells transfected in vitro with the BAPCs-DNA complexes showed transfection frequencies approaching 55% (higher than cells treated with Lipofectin®). Notably, the size of the DNA constructs that can be delivered successfully can be larger since dsDNA can form complexes with the exterior surface of one or more BAPC particles. For this study, we delivered a 19.4 kb plasmid achieving significantly higher transfection efficiencies than those reached with cationic lipids. We tested the in vivo transfection performance of BAPCs with a plasmid DNA encoding an oncoprotein of HPV-16, previously used as a therapeutic anti-tumor vaccine. Administration of DNA-BAPC nanoparticles to mice showed that high N:P ratios, compatible with optimal HeLa and HEK-293 cell transfection effects, did not improve the protective immunity of the DNA vaccine. However, a lower N:P ratio resulted in substantial in vivo anti-tumor effects.

This results demonstrated that the N:P ratio should be adjusted for each cell type and application purpose. Neutral zeta potentials (~1.5 mv) reduce the adsorption to serum proteins, resulting in longer circulation half-lives, while large or highly positively charged nanoparticles are trapped in the lung and do not enter systemic circulation. Additionally, low zeta potentials are associated with low cytotoxicity and little or no tendency for aggregation. This may explain why the N:P=1.3 ratio with low zeta potential (~2.00 my) was the formulation that efficiently controlled tumor growth in vivo. The size, shape, and degradability of nanoparticles, could all affect in vivo gene delivery. Other parameters such as coronal effects and the resting potential of cells can also impact the nanoparticle performance. By testing additional constructs with multiple cell types in the near future we hope to determine the underlying physical determinants.

We demonstrated that BAPC-DNA complexes activate DCs, which are responsible for activation and antigen presentation to effector cytotoxic T cells. Furthermore, the DNA-loaded BAPCs, at the most effective in vivo concentration, showed no detectable toxicity effects, as evaluated by some critical tissue injury biomarkers. Moreover, the administration of BAPCs complexed with a DNA vaccine (pgDE7), conferred protection to tumors cells expressing HPV-16 oncoproteins. BAPC complexation with pgDE7 resulted in the increase in the numbers of antigen-specific $CD8^+$ T cells and delayed tumor growth in mice previously grafted with TC-1 tumor cells. Together, these results indicate that the complexation of plasmid DNA to nano-sized BAPCs represents a promising non-viral gene delivery approach for in vitro transfection of mammalian cells and for the in vivo activation of immune responses.

Example 2

Introduction

BAPCs share several biophysical properties with lipid vesicles. They are, however considerably more stable—resisting disruption in the presence of chaotropes such as urea and guanidinium chloride, anionic detergents, proteases, and elevated temperature (~95° C.). Prior work utilized BAPCs formed from equimolar concentrations of the two branched peptides. In this study, different molar ratios of the two peptides were studied to test whether alternate ratios produced BAPCs with different delivery and biophysical properties. Additionally, preparation (annealing) temperature was assessed as a second variable. BAPCs were prepared with the following bis(Ac-h$_5$)-K—K$_4$—CO—NH$_2$ to bis(Ac-h$_9$)-K—K$_4$—CO—NH$_2$ ratios: 1:0, 0.8:0.2, 0.5: 0.5, 0.2:0.8, and 0:1. Also, capsules were annealed at 4° C., 25° C. and 37° C. BAPCs prepared at 4° C. showed the highest efficiency in encapsulating the fluorescent dye Eosin Y and those prepared using just bis(Ac-h$_9$)-K—K$_4$—CO—NH$_2$ showed the maximal transfection rates. These results suggest that equimolar concentrations of BAPCs are not essential for encapsulating solutes and delivering complexed DNA into living cells.

Materials and Methods

Peptide Synthesis.

Peptides were synthesized by solid phase peptide chemistry on 4-(2,4-Dimethoxyphenyl-Fmoc-aminomethyl)phenoxyacetyl-norleucyl-crosslinked Ethoxylate Acrylate Resin (Peptides International Inc.; Louisville, Ky.) on a 0.1 mmol scale using Fmoc (N-(9-fluorenyl) methoxycarbonyl)/tert-butyl chemistry on an ABI Model 431 peptide synthesizer (Applied Biosystems; Foster City, Calif.) with modified cycles and resin with reduced substitutions. The Fmoc L-amino acids were obtained from Anaspec, Inc. (Fremont, Calif.). The branch point was introduced by incorporating $N^{\alpha,\varepsilon}$ di-Fmoc-L-lysine in the fifth position from the C-terminus. De-protection of this moiety leads to the generation of two reactive amino sites thereby generating the bifurcated peptide branch point. This enables the addition two predominantly hydrophobic N-terminal tail segments FLIVIGSII (SEQ ID NO: 3) or FLIVI (SEQ ID NO:4) to the common hydrophilic oligo-lysine segment by the stepwise addition of Fmoc amino acids. The N-termini of the peptides were acetylated on the resin using Acetic Anhydride/N, N-Diisopropylethylamine/1-Hydroxybenzotriazole just prior to cleavage. The peptides were cleaved from the resin using TFA/water (98:2, v/v) for 90 min at RT to generate C-terminal carboxamide. The peptide products were washed 3× with diethyl ether. At this point the two peptides were treated differently. The shorter peptide was redissolved in water prior to lyophilization. The water used throughout this study is first deionized then reverse osmosis treated and finally glass distilled. The larger peptide was dried directly from the ether. The larger peptide has a propensity to form beta-structure in water leading to the formation of aggregates that persist after lyophilization. Drying directly from ether prevents this. The larger peptide was hydrated just before performing any analysis. The RP-HPLC purified peptides were dried in vacuo and characterized on a Bruker Ultraflex III matrix-assisted laser desorption ionization time of flight mass spectrometer (MALDI TOF/TOF) (Bruker Daltonics, Billerica, Mass.) using 2,5-dihydroxybenzoic acid matrix (Sigma-Aldrich Corp., St. Louis, Mo.). The dried peptides were stored at room temperature.

Capsule Formation and Encapsulation.

The bis(Ac-h$_5$)-K—K$_4$—CO—NH$_2$ and bis(Ac-h$_9$)-K—K$_4$—CO—NH$_2$ peptides were dissolved individually in neat 2,2,2-Trifluoroethanol. In this solvent, the peptides are helical and monomeric thereby ensuring complete mixing when combined. Concentrations were determined for the stock TFE dissolved samples using the molar extinction coefficient ($\varepsilon$) of phenylalanine residues (two per sequence) at 257.5 nm (195 cm$^{-1}$ M$^{-1}$). The bis(Ac-h$_5$)-K—K$_4$—CO—NH$_2$ and bis(Ac-h$_9$)-K—K$_4$—CO—NH$_2$ peptide solutions of known concentration were mixed to yield ratios of 1:0, 0.8:0.2, 0.5:0.5, 0.2:0.8 and 0:1, then dried in vacuo. BAPCs (50 µM) samples were prepared by hydrating the dried monomeric mixture of the constituent peptides dried from 100% TFE with aqueous Eosin Y (2.13 mM) or Rhodamine 6G (2 mM and 0.1 mM) and then allowed to assemble for 60 min at 4° C., 25° C. or 37° C. Fluorescence of Eosin Y strongly quenched at this concentration. Rhodamine 6G, which is also self-quenching, was used at two concentration, one that was quenching (2.0 mM) and the other at a concentration that yielded maximum fluorescence (0.1 mM). The dye loaded BAPCs were then wash by centrifugation was carried out at 14,000×g in Amicon ultra—0.5 mL 30 kDa molecular weight cut-off centrifugal cellulose filters (Millipore, Billerica, Mass.) using a Thermo Electron Legend 14 personal micro-centrifuge (Thermo Fisher Scientific Inc., Waltham, Mass.) to remove non-encapsulated dye. Samples were then subjected to multiple centrifugation cycles starting with a 5 min pre-incubation with 200 mM Na-TFA salt. The TFA$^-$ counter-ion successfully displaces negatively charged Eosin Y associated with the outer capsule surface. For the second-sixth wash cycles, the dye encapsulated capsules were incubated with just water prior to centrifugation. At the conclusion of the sixth spin, the removable-filter unit was inverted and placed in a fresh tube and spun at 2000×g for 5 min to recover the remaining volume containing the washed capsules. This sample was then diluted to the desired concentration with water.

For studies examining encapsulation efficiency and temperature effects Eosin Y (Sigma-Aldrich Corp. St. Louis Mo.) or Rhodamine 6G (Sigma-Aldrich Corp. St. Louis Mo.) were present in the hydration solutions at desired concentrations. After BAPC formation in the presence of either dye (60 min) the samples were passed through a 0.2 µm PTFE syringe filter (Millipore Millex FG, Billerica, Mass.). Fluorescence measurements of the encapsulated contents were carried out by the excitation of Eosin Y at 490 nm and scanning for observed emissions from 495-800 nm with a CARY Eclipse Fluorescence spectrophotometer (Varian Inc., Palo Alto, Calif.) (Scan rate: 600 nm/min; PMT detector voltage: 600 V; Excitation slit: 10 nm; Emission slit: 10 nm) using a 0.3 cm path length quartz cuvette. Standard curves examining the concentration and temperature effects on of Eosin Y fluorescence were performed and used to correct data obtained for these effects.

For the temperature studies with the different peptide ratios, changes in the fluorescence intensity of the dye Eosin Y were followed as a function of temperature. The dye was used at a concentration that quenches the fluorescence. Any lysis of the BAPCs would result in an increase in fluorescence intensity. For these studies, the BAPCs were prepared at 4° C. for at least an hour before washing. The fluorescence was initially measured at 4° C. followed by jumps to 25° C. then 37° C. followed in some experiments by 10° C. increases up to 95° C.

Circular Dichroism Experiments.

Circular Dichroism (CD) experiments were conducted to analyze conformational changes in secondary structures formed by the water-filled 1 mM BAPCs prepared with the different peptide ratios. Data were collected on a Jasco J-815 CD spectrophotometer (Jasco Analytical Instruments, Easton, Md.) using a 0.2 mm path-length jacketed cylindrical quartz cuvette (Starna Cells Inc., Atascadero, Calif.). Spectra were scanned from 260 nm to 190 nm at a scan rate of 50 nm min$^{-1}$ with 1 nm step intervals. All experimental temperatures were maintained using a Heating/Cooling Fluid Circulator (IBM Corp.) connected to the jacketed cuvette. CD spectra were measured in 'mdeg' using an average of five scans. The raw data was subtracted from blank at the appropriate temperature and smoothed using a Savitsky-Golay filter using Spectra Analysis® software provided by the manufacturer (Jasco Inc., Easton, Md.). Peptide concentrations were determined using the absorbance of phenylalanine.

Dynamic Light Scattering and Zeta Potential.

Branched amphipathic peptides with varying ratios of bis(Ac-$h_5$)-K—$K_4$—CO—$NH_2$ and bis(Ac-$h_9$)-K—$K_4$—CO—$NH_2$ were hydrated at 4° C. to yield BAPCs incorporating a total peptide concentration of 2 mM. These were maintained at 4° C. for 3 h before bringing them to RT prior to analysis. Dynamic light scattering (DLS) and Zeta Potential (ZP) analysis was performed using a Zetasizer Nano ZS (Malvern Instruments Ltd., Westborough, Mass.). The accuracy of the instrument was validated using 30 nm and 90 nm Nanosphere—NIST traceable mean diameter standards (Thermo Fisher Scientific, Waltham, Mass.).

Preparation of DNA-BAPCs Nanoparticles.

BAPCs (45 µM) were prepared at different ratios of bis(Ac-$h_5$)-K—$K_4$—CO—$NH_2$ and bis(Ac-$h_9$)-K—$K_4$—CO—$NH_2$ and hydrated at different temperatures (4° C., 25° C. and 37° C.). Subsequently, they were mixed with 2.5 µg of pEGFP-N3 (Clontech, Mountain View, Calif.). The charge ratio (N:P) ratio was 26. The N:P charge ratio for a given complex has been previously defined. Solutions were mixed carefully with a pipette and allowed to stand for 10 min at RT before adding $CaCl_2$, 1.0 mM final concentration. After an additional 30 min incubation period, the solution was added to the cell culture. $CaCl_2$, alone at this concentration was analyzed and did not to enhance DNA uptake or expression In Vitro Plasmid Transfection.

For transfection experiments, cells were seeded and 24 h later at 60% confluence, all medium was removed from the wells and 800 µL of Opti-MEM® I Reduced Serum Media was added. Next, 200 µL of BAPCs-DNA nanoparticles were added to cells. The BACPs-DNA complexes were incubated with cells for 4-6 h at 37° C./5% $CO_2$. After the incubation period, media and transfection reagent were removed and replaced with 1 mL of fresh DMEM containing 10% FBS in each well. The cells were returned to the incubator for 48 h. After this incubation period, transfection efficiency was monitored by fluorescence microscopy and quantified by flow cytometry (Accuri C6 Flow Cytometer®, Beckon Dickson, San Jose, Calif.). Ghost Dye™ Red 780 (Tonbo Biosciences, San Diego, Calif.) was used to identify and then exclude dead cells from the analysis. Non-transfected cells containing only DNA and $CaCl_2$ (1 mM) were used as a control. For the positive control, cells were transfected with jetPRIME® (PolyPlus, Strasbourg, France) following the manufacturer protocol. Data were analyzed using the FlowJo software V.10.1 (TreeStar, Oreg., USA).

Fluorescence Microscope Images.

Images were obtained using an Eclipse Ti2 inverted microcopy system (Nikon, Melville, N.Y.).

Results and Discussion

Physicochemical and Structural Properties of BAPCs Assembled at Different Temperatures and with Different Peptide Ratios.

Original work relied on equimolar ratios of bis(Ac-$h_5$)-K—$K_4$—CO—$NH_2$ and bis(Ac-$h_9$)-K—$K_4$—CO—$NH_2$ to prepare the BAPCs. It was reasoned that including the shorter sequence with the longer sequence could ease any strain due to curvature and thereby facilitate assembly. When we examined the actual distribution of the two peptides in the assembled bilayers we observed that the outer leaflet contained both sequences with the larger peptide predominating. Exact ratios were difficult to assess due to the variability involved in the self-assembly process. The ability of this ratio to meet the original design goals left studying the individual peptides as well as all other ratios untested. In more recent work, equimolar ratios yielded BAPCs with unusual thermal transitions. Capsules prepared at 25° C. spontaneously fused to form a heterogeneous population of larger spherical structures while those prepared at 4° C. and 37° C. were uniform spheres with a fixed diameter of 20-30 nm. The secondary structure of the peptides in the assemblies were predominantly random coil or beta-structures for 4° C. and 37° C., respectively. The 25° C. peptides were a mixture of the two but transitioned to beta as the capsules grew in size.

Figure 10:
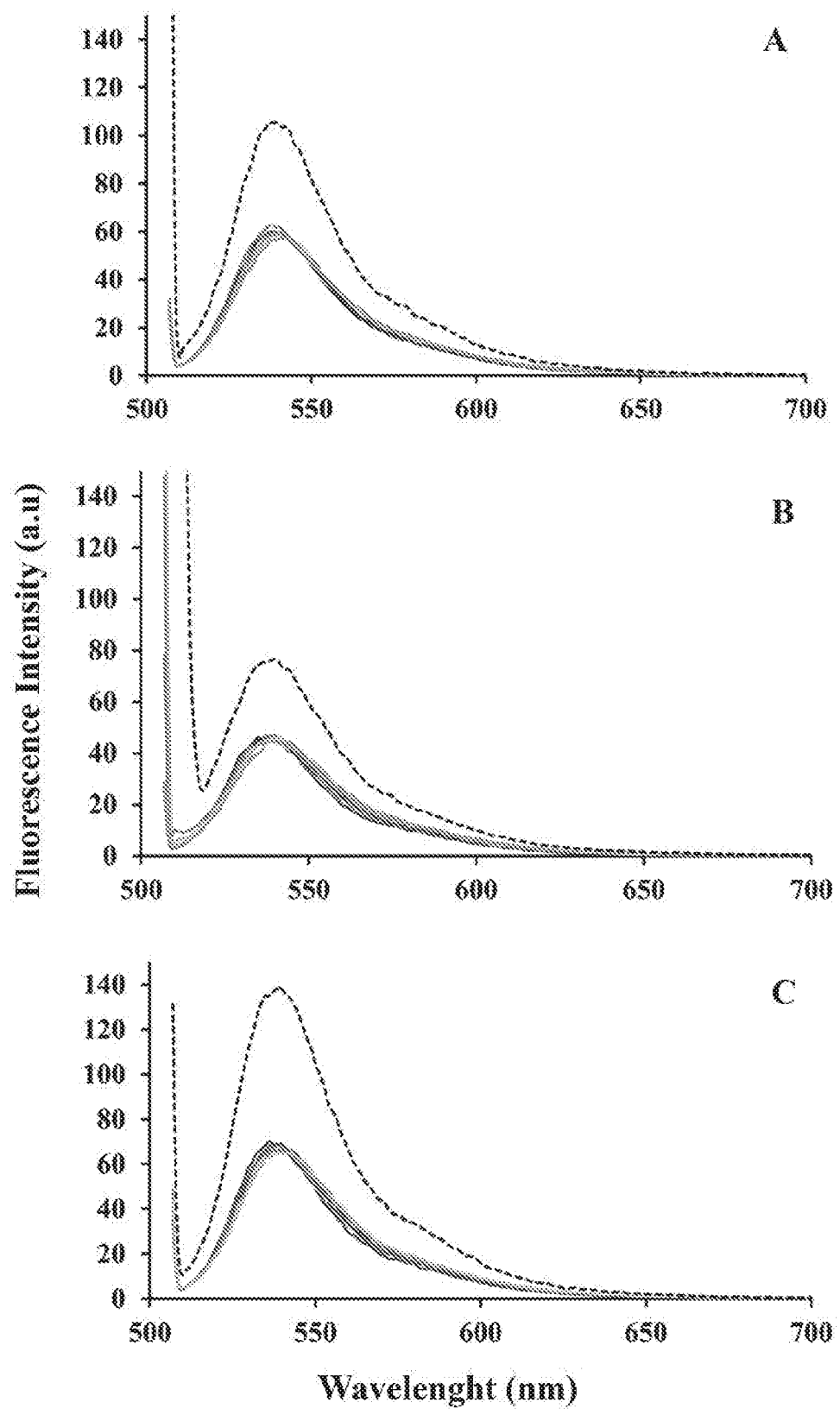
FIG. 10 shows the results of thermal stability of BAPCs prepared at different peptide ratios: (A) 1:0; (B) 0.5:0.5; and (C) 0:1, where the dashed line represents the BAPCs disassembled in the presence of 50% TFE at the end of the experiment.

In an effort to design BAPCs with new properties, BAPCs (50 µM) were prepared using three different $h_5$:$h_9$ peptide ratios (1:0, 0.5:0.5, and 0:1). They were annealed at 4° C. and then tested for thermal stability. The dye Eosin Y was encapsulated at a concentration that shows significant quenching (2.1 mM in water). The washed dye encapsulated BAPCs were ramped rapidly to 25° C. and then heated to 95° C. with 10° increments over a period of 2 h. As depicted in FIG. 10 the three different BAPC preparations (1:0 (panel A); 0.5:0.5 (panel B); and 0:1 (panel C) clearly trap the dye during capsule formation and remained intact throughout the experiment as judged by the absence of dye release. At the end of each experiment an equal volume of TFE was added to the sample to yield a 50% TFE solution that causes the capsules to disassemble thereby releasing the dye (dotted line), leading to the expected increase in fluorescence intensity. A 0.5× dilution constant was factored in, while graphing the increase in fluorescence intensity due to dye release, to account for the 50% dilution of the sample due to the addition of TFE. This was done for clarity since the released dye curve falls on top of the other spectra. The 50% TFE curve was also corrected for any fluorescence enhancement due to solvent. These results indicate that a mixture of longer and shorter branched peptides is not required for BAPC formation and that encapsulated solutes can be released upon disassembly in 50% TFE solutions.

Figure 11:
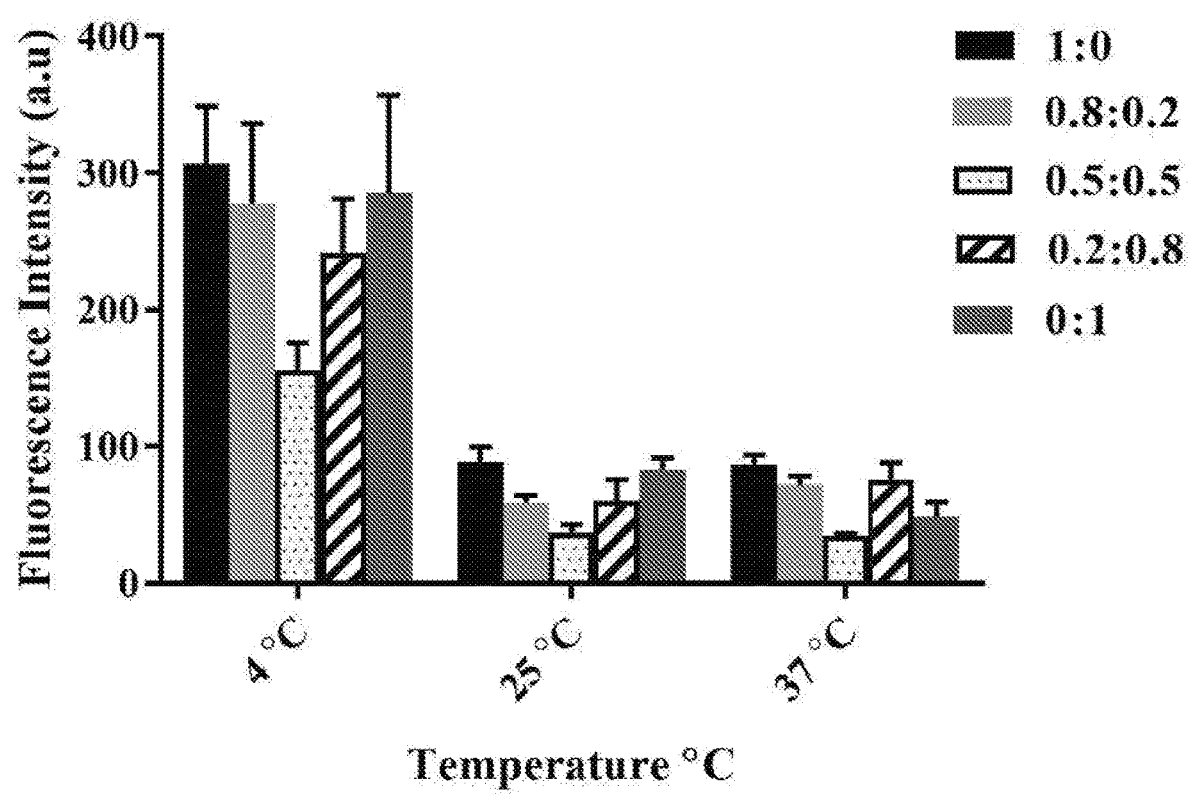
FIG. 11 is a graph showing the temperature dependence on dye encapsulation for BAPCs prepared at different peptide ratios for 1 h. Data represent mean values+SEM of three experiments combined.

The peptide and dye concentrations for each ratio were identical however the amount of encapsulation was less in the BAPCs prepared with the equimolar peptide ratio. To verify this observation BAPCs were prepared with the following ratios (1:0, 0.8:0.2, 0.5:0.5, 0.2:0.8, and 0:1). For this experiment the annealing temperatures were included as a second variable. All of the ratios formed BAPCs at the three different temperatures (FIG. 11). The 4° C. assemblies showed the highest encapsulation values. Over the conditions tested here is roughly a four-fold difference in the amount encapsulated comparing the highest loading with the 4° C. assembly of just bis(Ac-$h_5$)-K—$K_4$—CO—$NH_2$ compared with the 37° C. assembly made using a 0.5:0.5 ratio. Looking within each temperature grouping the highest values are recorded for the more homogeneous ratios, with the equimolar ratio showing the least amount of trapped solutes during assembly. While the net encapsulation values decreased with increasing temperatures the pattern of increased encapsulation at the more homogeneous ratios was preserved. The trend showing increased encapsulation at the more homogeneous ratios was unexpected. The 0.5:0.5 ratio, which showed the lowest level of dye encapsulation, could be the result of a slower annealing rate or a higher level of precipitation. Examining the Eosin Y encapsulation process carefully we observed tiny colored aggregates in many of the samples. A possible explanation for this is discussed in the section that shows the zeta potential for BAPCs formed with the different peptide ratios. These samples are always filtered using a 0.2 micron PTFE syringe filter. The weights of the dried residue left on the filters showed that the equimolar ratio of peptide showed had the highest level of aggregation, double that of a homomeric ratio. This result supports the idea that lower encapsulation is the result of reduced concentrations of the equimolar ratio peptide assembly in the presence of the Eosin Y.

Figure 12:
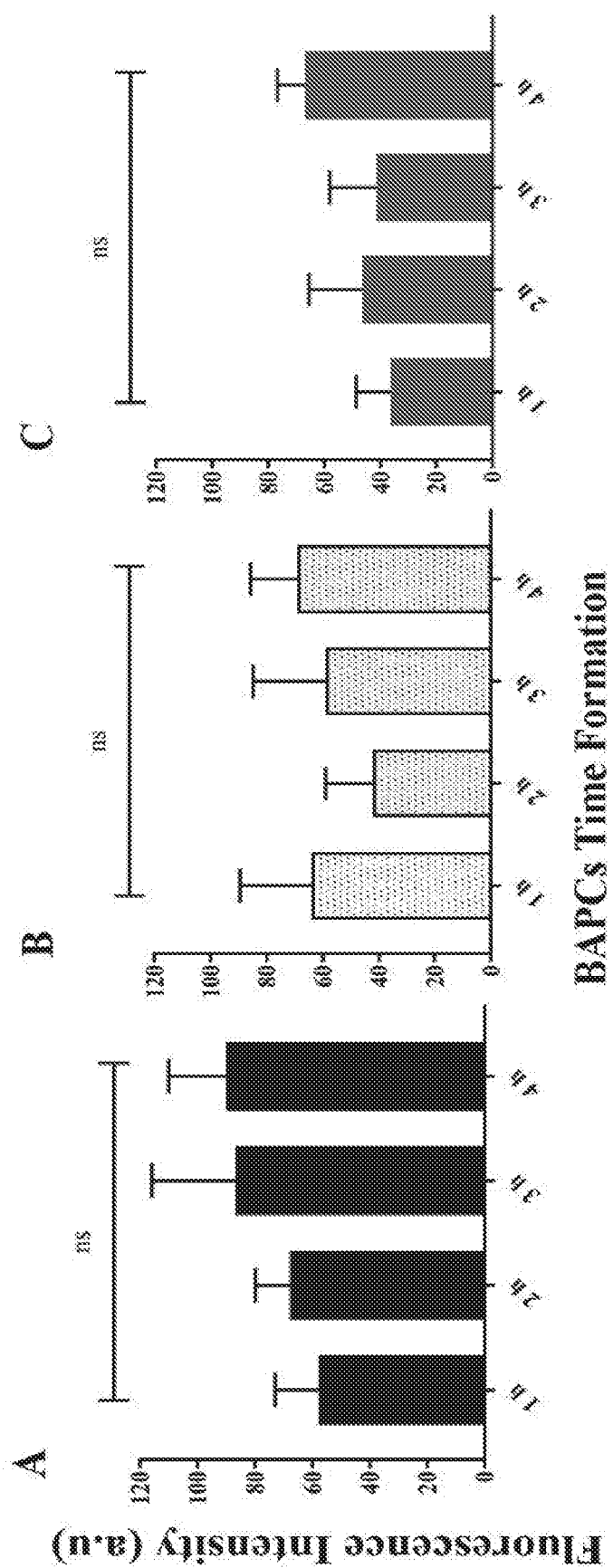
FIG. 12 contains graphs showing the Time dependence at 4° C. for loading of Rhodamine 6G (100 µM) for BAPCs prepared at different peptide ratios: (A) 1:0; (B) 0.5:0.5; and (C) 0:1.

To further test these results, an encapsulation time-course experiment was performed over 24 h at 4° C. using Rhodamine 6G (FIG. 12). This dye is positively charged and does not interact as strongly with the cationic surface of the capsules. No precipitation was observed when this dye (at quenching concentrations (2.0 mM) was mixed with any of the peptide ratios. The dye was also used at a concentration (0.1 mM) that provides maximum fluorescence. Together, these conditions provide for fluorescence intensities that give the best opportunity to identify any changes in encapsulation over time. The bis(Ac-$h_5$)-K—$K_4$—CO—$NH_2$ only (FIG. 12A) and bis(Ac-$h_9$)-K—$K_4$—CO—$NH_2$ only (FIG. 12B) BAPCs along with the 0.5:0.5 ratio (FIG. 12C) were tested. With each BAPC ratio, self-assembly at 4° C. was essentially complete by 60 min. No significant statistical difference was seen for the times tested. These results supports the idea that the decreased encapsulation efficiency observed for Eosin Y with the equimolar ratio is a consequence of the loss of peptide due to precipitation.

While annealing temperature had no effect on the rates of assembly, earlier studies on BAPCs prepared using an equimolar mixture of bis(Ac-$h_5$)-K—$K_4$—CO—$NH_2$ and bis(Ac-$h_9$)-K—$K_4$—CO—$NH_2$, the annealing temperature had a profound effect on the secondary structure of the assembled peptides. As stated previously, the equimolar BAPCs displayed predominantly random coil at 4° C., mixed random and beta at 25° C. and beta at 37° C. To better understand the effects of peptide ratio on structure in the assembled peptides, the secondary structures were analyzed by circular dichroism (CD).

Figure 13:
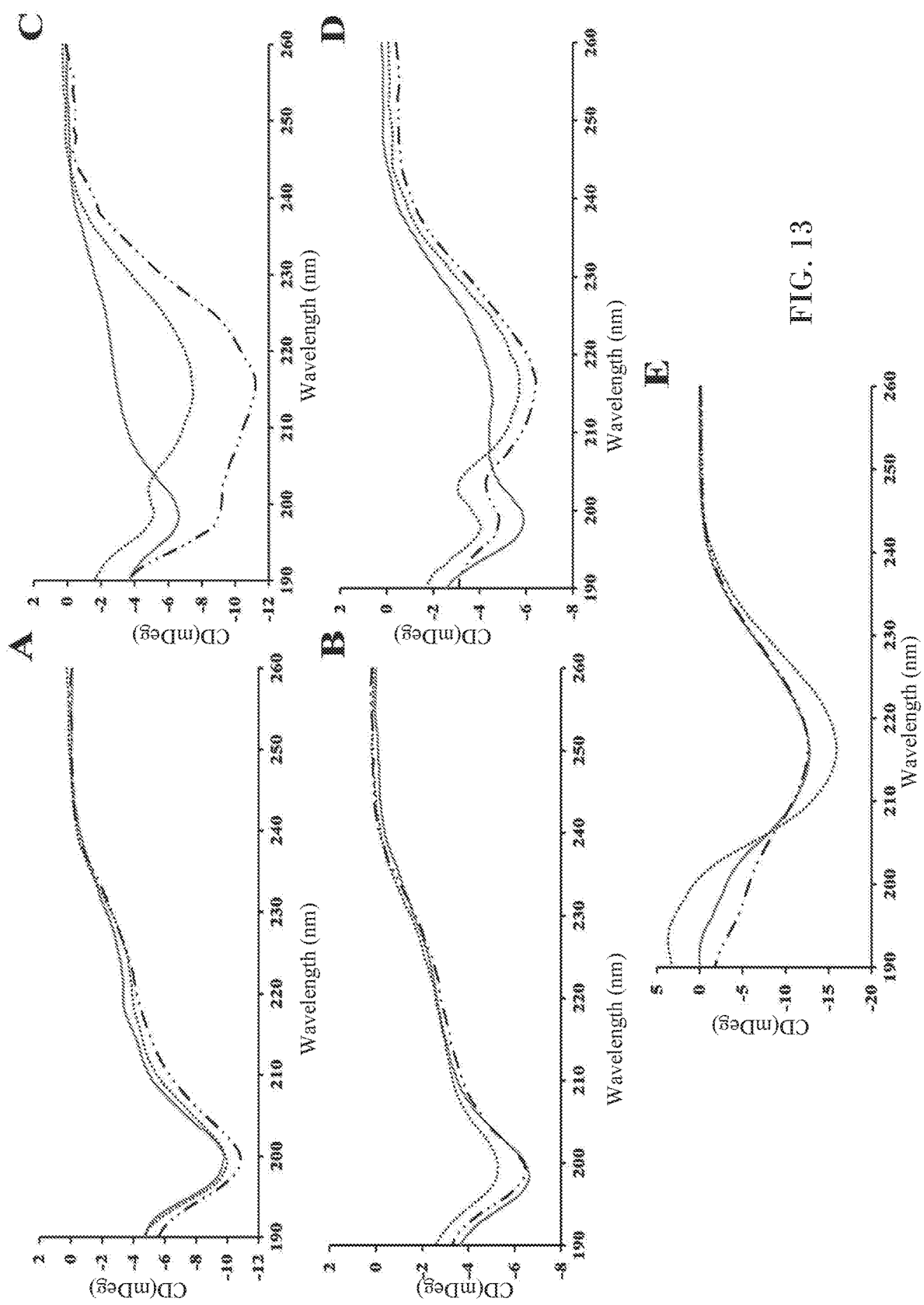
FIG. 13 contains graphs for the Circular Dichroism (CD) spectra for five different ratios of $h_5$:$h_9$ prepared at 4° C. (gray), 25° C. (dotted) or 37° C. (dot-dash) for 75 min: (A) 0:1; (B) 0.8:0.2; (C) 0.5:0.5; (D) 0.2:0.8; and (E) 0:1. All scans were performed at 25° C.

This analysis was repeated for the five different ratios to examine the contributions of the two peptide-sequences to the assembled structures. For these CD studies, 1 mM BAPCs were prepared using the five ratios used in FIG. 11 assembled at 4° C., 25° C., and 37° C. for 75 min before recording the CD spectra at 25° C. (FIG. 13). The BAPCs comprised of 100% (FIG. 13A) and 80% (FIG. 13B) bis (Ac-$h_5$)-K—$K_4$—CO—$NH_2$ display mostly random coil secondary structure with a strong minimum at 198 nm at all three temperatures. The 100% bis(Ac-$h_5$)-K—$K_4$—CO—$NH_2$ BAPCs (FIG. 13A) shows a minor minimum at 222 nm suggesting a minor helical component. This structure is absent in the 80% bis(Ac-$h_5$)-K—$K_4$—CO—$NH_2$ BAPCs (FIG. 13B). The equimolar ratio (FIG. 13C) adopts the random coil conformation only at 4° C. With increasing temperatures (25° C. and 37° C.) a mixture of random- (198 nm) and beta-structures (218 nm) are present. The 20% (FIG. 13D) bis(Ac-$h_5$)-K—$K_4$—CO—$NH_2$ BAPCs show increasing amounts of beta with a decrease in random coil at elevated temperatures. The 0% (FIG. 13E) bis(Ac-$h_5$)-K—$K_4$—CO—$NH_2$ BAPCs show essentially only beta-structure at all temperatures. Examining all of these data reveal that bis(Ac-$h_5$)-K—$K_4$—CO—$NH_2$ is unstructured while bis (Ac-$h_9$)-K—$K_4$—CO—$NH_2$ adopts beta-structure and that mixtures of the two peptides produce BAPCs with both structures present. From previous studies, only BAPCs showing mix conformations underwent fusion. Those prepared under conditions where random or beta structure predominated, were uniform and size stable 20-30 nm capsules that formed and remained as such when transitioned to higher temperatures.

Figure 14:
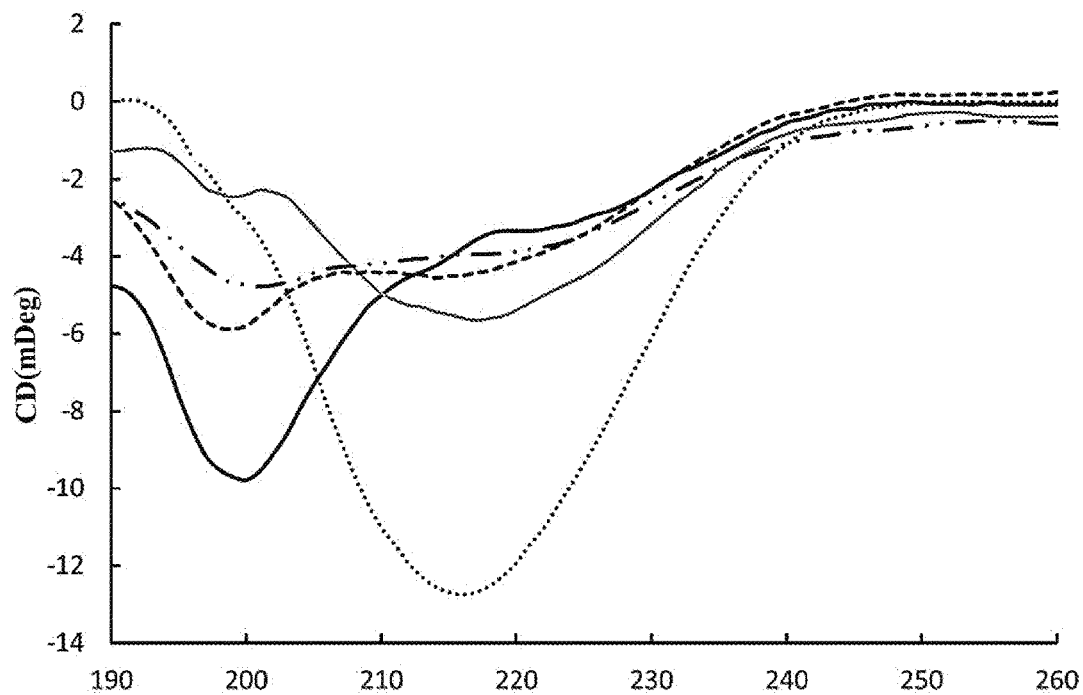
FIG. 14 is a CD spectra of BAPCs comprised of different ratios of $h_5$:$h_9$ assembled at 4° C. The spectra shown are 1:0 (dark solid line); 0.8:0.2 (dashed line); 0.5:0.5 (dot/dash line); 0.2:0.8 (light gray line) 0:1 (dotted line)

A composite figure comparing the final spectra for the 4° C. annealing temperature is shown in FIG. 14 and a table showing This figure shows the relative contributions of the two sequences to the final structure of the peptides in the assembled BAPCs. The BAPC bilayers comprised of just unstructured peptides should show a decrease in thermal stability over those where beta-structure inter-peptide hydrogen bonding predominates. Over the temperature range tested (up to 95° C.) there was no difference in stability (based on retention of the quenched Eosin Y). Hydrophobic interactions must be providing the cohesive forces that maintain their assembled structures to 95° C. Perhaps at temperatures above the range we tested, differences in thermal stability will become apparent. Pi-Pi stacking interactions of the phenylalanines that populate the bilayer interface do not appear to be involved based on atomistic simulations previously reported.

The observation that all of these mixed and more homogeneous structures support assembly and temperature stability imply that these structural arrangements have to be stabilized in different ways. The extended random coil structures would have to form bilayers with a longer cross-sectional distance or as random coils they could have a shorter cross-sectional distance if they inter-digitated. Analogously, the predominantly beta-sheet containing BAPCs should have the shortest cross-sectional distance. Differences in the thickness of the bilayer should affect the size of the BAPCs.

Figure 15:
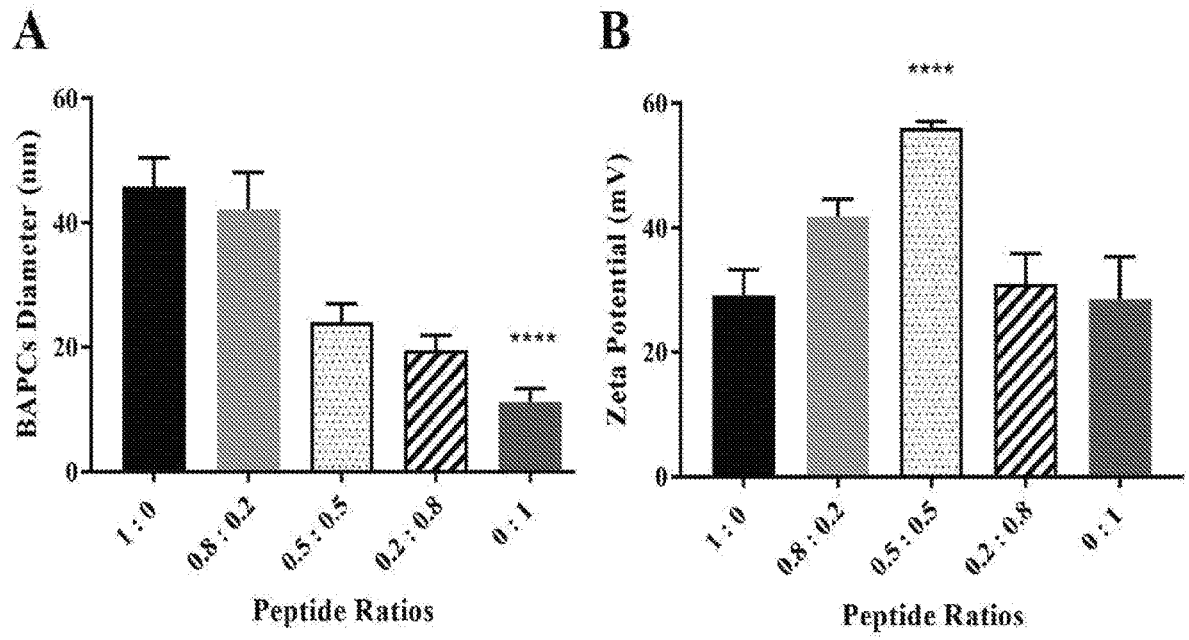
FIG. 15 contains graphs showing the (A) Average diameter; and (B) Zeta potential of BAPCs formed at five different $h_5$:$h_9$ ratios.

To test this hypothesis BAPC's prepared at 4° C. (3 h) were analyzed at 25° C. by dynamic light scattering. Under these conditions the BAPCs form uniform stable structures, even when moved to the higher temperature. Three separate preparations were analyzed (FIG. 15). This experiment clearly demonstrates that BAPCs prepared with different peptide ratios adopt different sizes to accommodate for aggregate differences in secondary structure. Dynamic light scattering (DLS) experiments were conducted using 1 mM solutions of the peptides with the five bis(Ac-$h_5$)-K—$K_4$—CO—$NH_2$ to bis(Ac-$h_9$)-K—$K_4$—CO—$NH_2$ ratios (1:0, 0.8:0.2, 0.5:0.5, 0.2:0.8, and 0:1). The average diameters (in nm) observed were 45.9±4.7, 42.2±5.8, 24.0±2.8, 19.5±2.4 and 11.2±2.1, respectively. The DLS value observed for the 0.5:0.5 ratio is in excellent agreement with those observed in our earlier TEM experiments. Prior to performing the experiments described herein, we hypothesized that the longer peptide sequence would yield larger BAPCs. Given the present findings the larger peptide's propensity to form compacted beta-structure prevails, thereby yielding the smallest structures.

Another interesting observation is that despite their size differences, equimolar batches of the different ratios encapsulate the same amount of dye. We observe less than nano molar concentrations of free peptide by mass spectrometry after filtering BAPCs with a 30 kDa cut-off Amicon Cellulose Centrifugal Filter (Merck). This results points to an extremely low critical association constant. It seems nearly all of the peptides participate in BAPC assembly or aggregation, with the pure bis(Ac-$h_9$)-K—$K_4$—CO—$NH_2$ yielding a greater number of smaller BAPCs while the shorter bis(Ac-$h_5$)-K—$K_4$—CO—$NH_2$ forms fewer larger BAPCs when the peptides are in an extended conformation. To further investigate the biophysical properties of BAPCs we analyzed the ZP for the five ratios previously analyzed by DLS (1:0, 0.8:0.2, 0.5:0.5, 0.2:0.8, and 0:1). The 1:0, 0.8: 0.2, 0.2:0.8, and 0:1 ratios showed similar ZP's. The basis for the 0.5:0.5 ratio showing the higher ZP (~57 mV) is unclear. We hypothesized that this higher surface charge at this ratio affects assembly in the presence of Eosin Y leading to precipitation.

In Vitro Transfection Efficiency of BAPCS Assembled at Different Temperatures and with Different Peptide Ratios.

Figure 16:
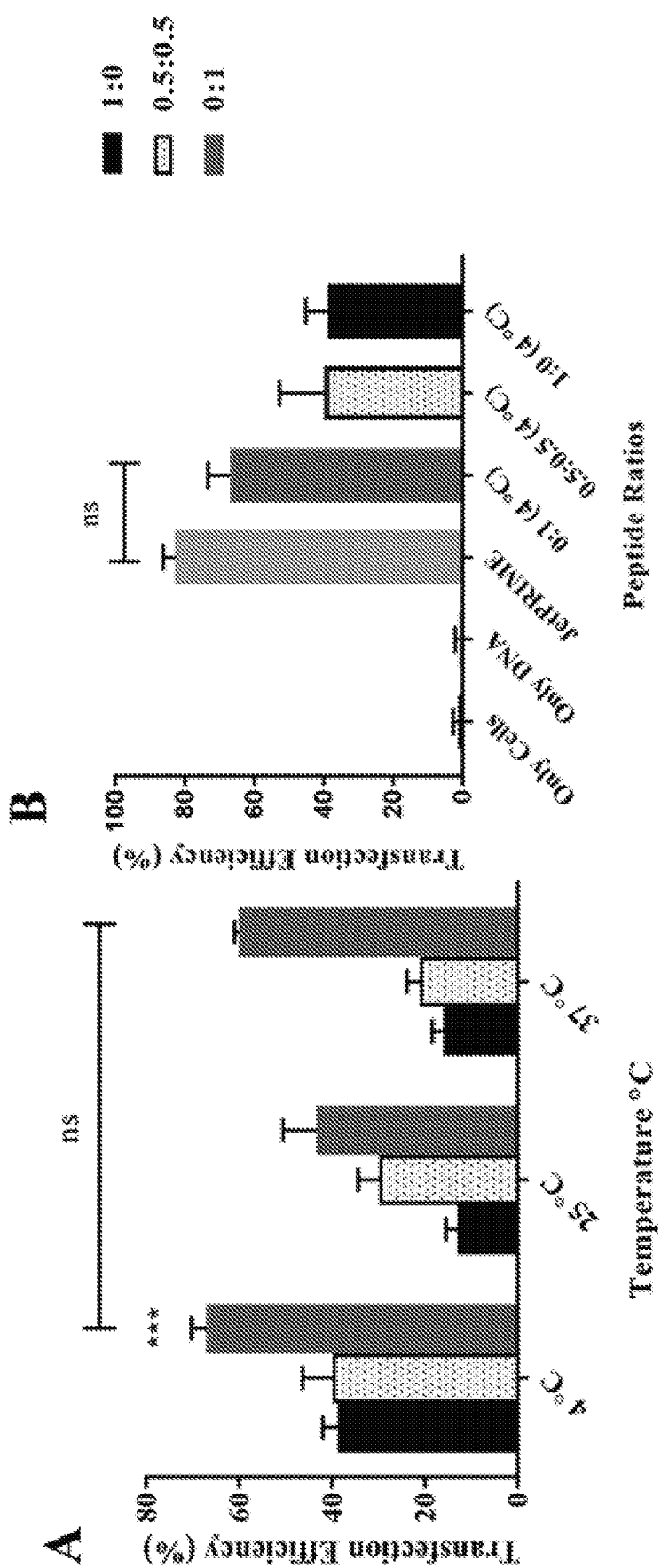
FIG. 16 shows (A) the transfection efficiency in HEK-293 cells of BAPCs-DNA nanoparticles from BAPCs solutions (45 µM) hydrated at 4° C., 25° C. and 37° C.; and (B) transfection efficiency of BAPCs solutions at different ratios and (45 µM) hydrated at 4° C. and positive (JetPRIME®) and negative (Only DNA) controls.
Figure 17:
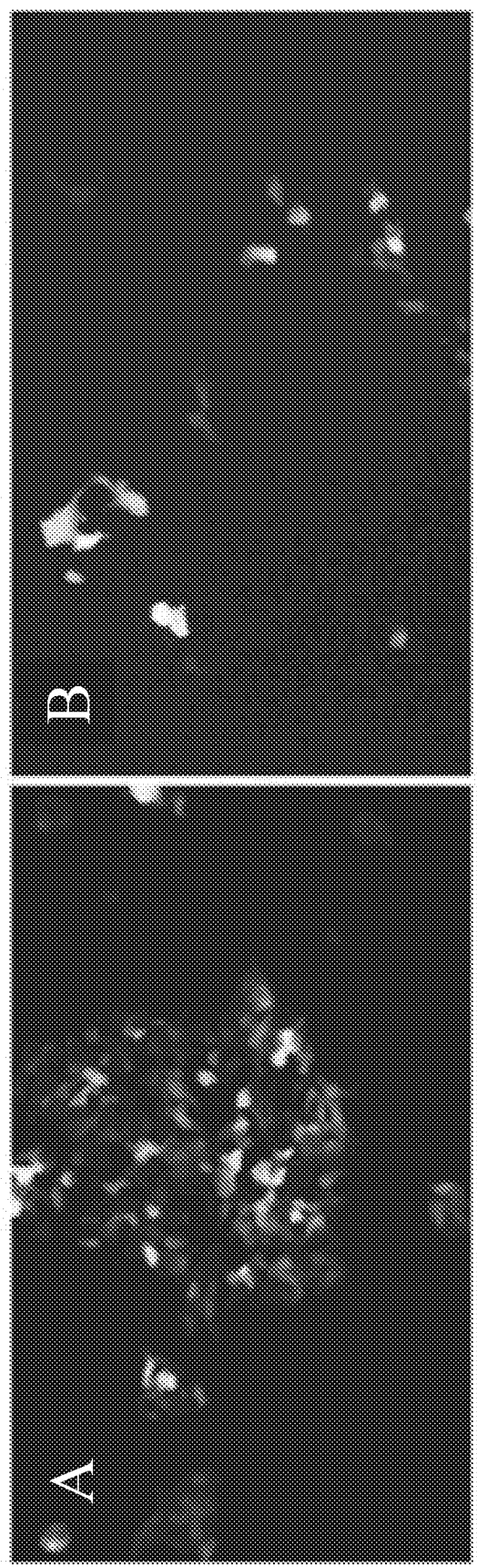
FIG. 17 shows fluorescence microscope images of HEK-293 cells transfected (A) only with (A) bis(Ac-$h_9$)-K—$K_4$—CO—$NH_2$ (0:1) and (B) only with bis(Ac-$h_5$)-K—$K_4$—CO—$NH_2$ (1:0)
Figure 18:
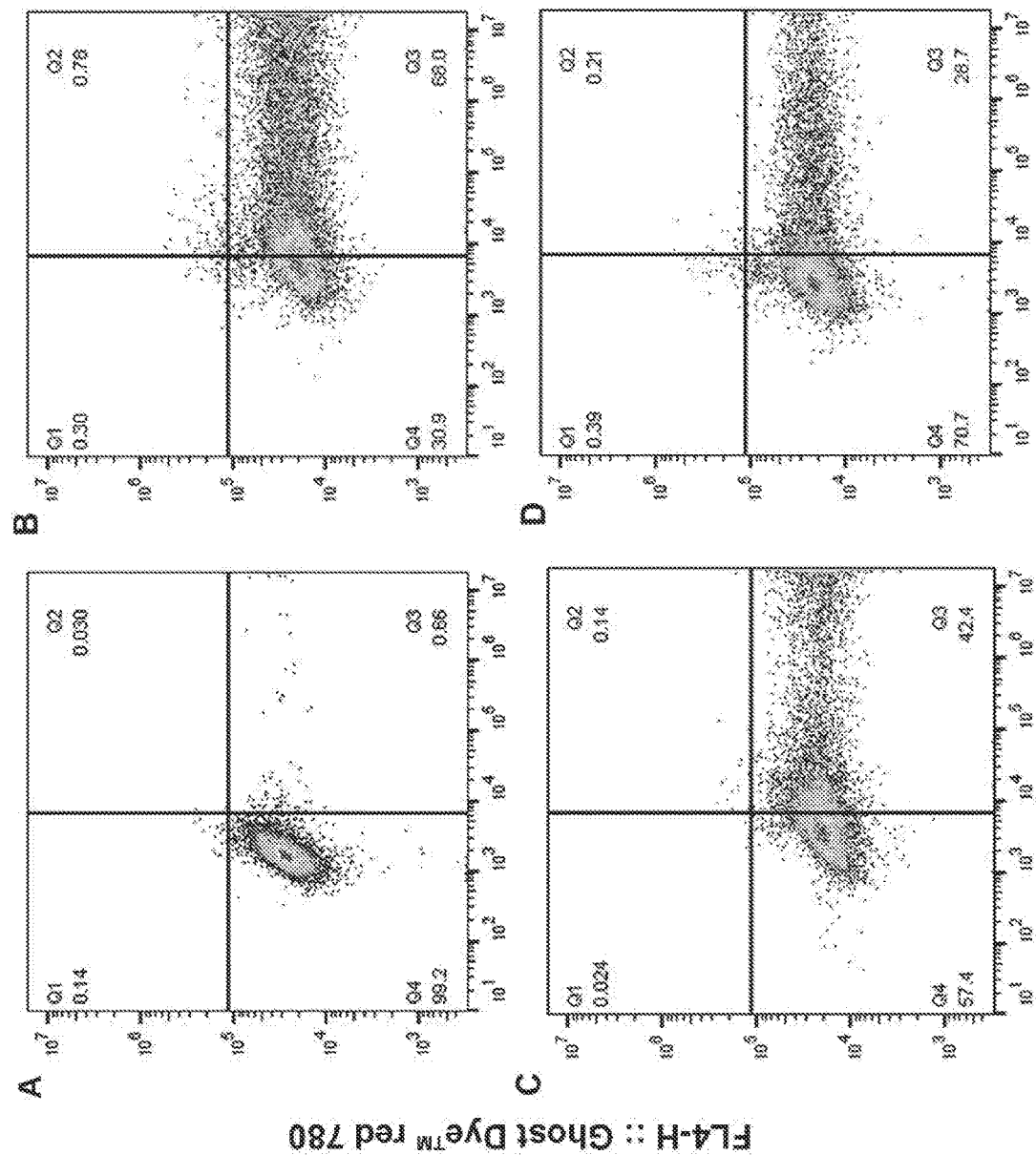
FIG. 18 contains the results of flow cytometry analysis of GFP-expressing HEK-293 cells after 48 h post transfection with BAPCs formed at different $h_5$:$h_9$ ratios: (A) Only cells; (B) 1:0; (C) 1:1; and (D) 0:1.

As illustrated in Example 1, the BAPCs are able to delivery various-sized DNA to cells with transfection rates of ~55% and minimal cytotoxicity. In this study, we analyzed how transfection efficiency was affected by preparing BAPCs at different temperatures and different peptide ratios. HEK-293 cells were incubated with BAPCs associated with a 4.7 kb GFP-encoding plasmid and transfection efficiency was monitored qualitatively by fluorescence microscopy and quantified using fluorescence-activated cell sorting (FACS). Ghost Dye™ Red 780 was used to identify and then exclude dead cells from the analysis. Dead cells with compromised membranes allow Ghost Dye to permeate and bind amine groups of intracellular proteins resulting in fluorescence much brighter than live cells which are impermeant to Ghost Dye. We selected this dye because the emission peak is 780 nm and do not overlap with the emission peak of GFP (509 nm), thus ensuring the exclusion of false positives. Maximal transfection rates were observed for BAPCs annealed at 4° C. and 37° C. using just bis(Ac-h$_9$)-K—K$_4$—CO—NH$_2$ (0:1 ratio) (FIG. 16A). As shown in FIG. 16B there was no significant difference between this ratio and the popular commercial transfection reagent (JetPRIME®). For BAPCs prepared at 4° C. the size decreases from 46 to 25 to 10 nm (FIG. 15A) and the transfection rate increases from ~39% to 41% to 70% (FIG. 16B). BAPCs annealed at 37° C. displayed also high transfection rates for the 0:1 ratio suggesting than not only the size but also the secondary structure (beta-structure) are influencing transfection rates. By exploring alternative methods to assemble BAPCs we were able to enhance transfection efficiency ~15% (compared with our previous method) while maintaining low cytotoxicity as demonstrated with flow cytometry analysis. Fluorescence microscope images of HEK-293 cells transfected only with bis(Ac-h$_9$)-K—K$_4$—CO—NH$_2$ (0:1) and (C) only with bis (Ac-h$_5$)-K—K$_4$—CO—NH$_2$ (1:0) are shown in FIG. 17A and FIG. 17B. As shown in FIG. 18 A-D the percent of dead cells is minimum for all the formulations tested (>1%) proving that BAPCs are extremely biocompatible.

Conclusions

The results presented above show that BAPCs can be prepared from either of the two peptides by themselves or mixtures thereof. The shorter peptide bis(Ac-h$_5$)-K—K$_4$—CO—NH$_2$ imparts random secondary structure to the BAPCs at each annealing temperature. The larger peptide bis(Ac-h$_9$)-K—K$_4$—CO—NH$_2$ folds, yielding beta-structure at all temperatures above 4° C. Combining the peptides generates mixed secondary structures. All ratios resulted in thermally stable constructs. The results of this experiment show that we can now prepare stable, homogeneous BAPCs that can be made to incrementally vary in diameter from approx. 10 nm to 45 nm.

Many of our most current applications involve the delivery of dsDNA and dsRNA, which bind to the surface of preformed BAPCs. In this report, we demonstrated that the ratio of the two peptides and the annealing temperatures affected the delivery efficiencies of DNA in HEK-293 cells. Higher transfection rates were observed in this experiments. BAPCs annealed at 4° C. and 37° C. using just bis(Ac-h$_9$)-K—K$_4$—CO—NH$_2$ (h$_5$:h$_9$, 0:1 ratio) displayed efficiencies approaching 70%. It is noteworthy that those annealing temperatures (4° C. and 37° C.) generated beta secondary structure. The ratio (0:1) generated BAPCs with sizes ~10 nm and ZP (~25 mV). Overall, these results suggested that those parameters are variables influencing the BAPCs' ability to deliver nucleic acids into cells. Further studies will consists in studying the morphologies of the BAPCs-DNA complexes that generated the highest delivery rates.

Example 3

Introduction

In this study, we inhibited expression of two insect genes, BiP and Armet, through transcript knockdown by oral delivery of dsRNA complexed with BAPCs. The dsRNA-BAPC complexes were added to the diets of insect species from two Orders: *Acyrthosiphon pisum* (pea aphid, sucking insect fed artificial liquid diet) and *Tribolium castaneum* (red flour beetle, chewing insect fed amended solid flour diet). As a major target in both species, we chose the transcript of BiP (GRP78). Its activity is important in the unfolded protein response (UPR). For *Tribolium*, we also included the transcript of another UPR member, Armet (also known as MANF). For *Acyrthosiphon pisum*, ingestion of <10 ng of BiP-dsRNA associated with BAPCs led to the premature death of the aphids ($t_{1/2}$=4-5 days) compared to ingestion of the same amounts of free BiP-dsRNA ($t_{1/2}$=11-12 days). *Tribolium castaneum* larvae were killed by ingestion using a combination of BiP-dsRNA and Armet-dsRNA complexed with BAPCs (75% of the subjects, n=30). The insects also died during eclosion (the emergence of adults from pupae). Feeding the two dsRNA alone resulted in fewer deaths (30% with n=30). In a separate experiment in *Tribolium*, we knocked down the *Vermillion* transcript, as an example of a transcript that is in a wholly internal organ (in contrast to the gut, a probable site of action in the knockdown of the BiP and Armet transcripts). *Vermillion* encodes the enzyme tryptophan oxygenase, required for brown eye pigment synthesis in *Tribolium*. Feeding of BAPC-*Vermillion*-dsRNA complexes resulted in the absence of eye color in treated insects. These results show that complexation of dsRNA with BAPCs greatly enhances the oral delivery of dsRNA over dsRNA alone in the diet. This approach provides a simpler method of delivering dsRNA compared to microinjection for studying in vivo protein function and for developing novel strategies for pest management.

Materials and Methods

Peptide Synthesis.

The branched amphiphilic peptides bis(Ac-h$_9$)-K—K$_4$—CO—NH$_2$ and bis(Ac-h$_5$)-K—K$_4$—CO—NH$_2$, were synthesized and cleaved. The cleaved peptides were washed three times with diethyl ether, dissolved in water, and lyophilized before storage at RT. The peptides were purified by reversed phase HPLC and characterized using matrix-assisted laser desorption/ionization-time of light (MALDI TOF/TOF).

BAPC's Preparation.

The peptides, bis(Ac-h$_9$)-K—K$_4$—CO—NH$_2$ and bis(Ac-h$_5$)-K—K$_4$—CO—NH$_2$, were individually dissolved in pure 2,2,2,-Triuoroethanol (TFE) and mixed together in an equimolar ratio in at 1 mM final concentration. Peptide concentrations were calculated using the molar absorptivity (ε) of phenylalanine in water at 257.5 nm (195 cm$^{-1}$ M$^{-1}$). After mixing they were allowed to stand for 10 minutes before removing the solvent under vacuum. 1 mL of water was added drop-wise into the dried peptide mixture and allowed to sit for 30 min at 25° C. to form capsules at 1 mM final concentration. Subsequently, the capsule containing solution was incubated for 1 h at 4° C. to prevent capsule fusion.

After 1 h, the peptide sample was returned to 25° C. for 30 min before drying or mixing with the dsRNA.

Preparation of dsRNA-BAPC's Nanoparticles.

To treat 10 µg *Tribolium castaneum* beetles, a solution containing 10 µg of *Tribolium* dsRNA of Armet, BiP or Vermilion was dissolved in 200 µL of water. This solution was added drop-wise to a 200 µL solution containing BAPCs at 400 µM. For the group treated with a combination of BiP-dsRNA and Armet-dsRNA, we added 5 µg of each and mixed it with 200 µL of BAPCs at 400 µM. Solutions were mixed carefully by pipette and allow to stand for 10 min before adding $CaCl_2$ at 20 mM final concentration. After 30 min incubation, the solutions were mixed with the insect diet.

To treat 5 *Acyrthosiphon pisum* pea aphids, 0.1 µg of *Acyrthosiphon pisum* BiP-dsRNA was dissolved in 10 µL of water. Subsequently, the solution was added drop-wise into a 10 µL solution containing BAPCs at 200 µM. Solutions were mixed carefully with pipette and allow to stand for 10 min before adding $CaCl_2$ at 12.5 mM final concentration. After another 10 min incubation period, sucrose (500 mM) was added. For the insects treated with lesser amounts of BiP-dsRNA, BAPC/nucleotide complexes prepared as above were diluted 10× and 100× with water prior to adding the $CaCl_2$.

Dynamic Light Scattering (DLS) and Zeta Potential (ZP).

The particle sizes and zeta-potentials for all dsRNA-BAPCs samples were determined using a Zetasizer Nano ZS (Malvern Instruments Ltd, Westborough, Mass.). Samples were analyzed in $CaCl_2$ (2 mM) and all measurements were performed in triplicates.

Atomic Force Microscopy.

The dsRNA-BAPCs complexes were deposited onto silicon substrates with native oxide. Topographical images were obtained using a ParkXE7 AFM from Park Systems (Korea) in non-contact mode, using a silicon cantilever (Park Systems, PPP-NCHR) with a nominal tip diameter of 14 nm and nominal of spring constant 42 N/m. The silicon substrates had a thin layer of native oxide (~1-2 nm) on the surface (HF/BOE etching was not performed).

Insects.

*Acyrthosiphon pisum* were maintained in cages on *Vicia faba* (broad Windsor) plants. All feeding trial bioassays were conducted at 22° C. and programmed for a cycle of 16 hr of light and 8 hr of darkness. *Tribolium castaneum* (GA-1 strain) insects were reared at 30° C. on wheat flour containing 5% brewer's yeast.

Diet Containing Ds-RNA-BAPC's Nanoparticles (*Tribolium castaneum*).

Media to feed 10 insects was prepared by mixing 70 mg Golden Buffalo Flour with 400 µL of dsRNA-BAPC's complexes. The flour and the dsRNA-BAPCs solution was mixed by inversion several times. This mixture was held under vacuum for approximately 10 h. When the mixture was complete dry, we distributed it into a 96-well plate, adding around 7 mg per well. Immediately, we placed one insect per well (in larvae and/or prepupae stage (mass around 2 mg). For the control group containing only dsRNA, we mixed 70 mg Golden Buffalo Flour with 10 µg of either Armet-, BiP- or Vermilion-dsRNAs dissolved in 400 µL of water and 160 mM $CaCl_2$. Other controls were prepared by just mixing 70 mg of flour with 400 µL of water plus and minus BAPCs (40 µM). We analyzed a total of 30-35 insects per group. Insects were kept at 30° C. for the indicated periods for the visual monitoring of phenotypes and mortality.

Diet Containing Ds-RNA-BAPC's Nanoparticles (*Acyrthosiphon pisum*).

For control samples, the aphids were placed on petri dishes containing sterilized 2% agar (supplemented with 0.1% Miracle grow fertilizer and 0.03% methyl 4-hydroxybenzoate) healthy leaf (fava beans) was inserted and feeding was carried out 48 hr. For the dsRNA feeding trial, up to five adult aphids (without over-crowding) were transferred with a fine paintbrush onto a feeding sterile plastic cup (Falcon, Primaria, N.J., USA). A layer of stretched parafilm (Fisher scientific, USA) was placed over plastic cups containing the 5 insects per cup. The artificial diet (20 µL) containing free- or BAPC-conjugated BiP-dsRNA was placed on top of parafilm stretched over the cup. A second layer of stretched parafilm was placed on top of the diet thus forming a pocket. The aphids fed on the diet by penetrating the bottom layer of parafilm. Three different concentration of dsRNA were used 0.1 µg, 0.01 µg and 0.001 µg containing 12.5 mM $CaCl_2$. Aphids were allowed to feed on the diet for 48 hr. Then the aphids were transferred to plant leaves for the control group. In each experiment, three replicates were included in the artificial diet feeding. Survival assays were conducted separately using 10×3 aphids per group in each feeding experiment. Each experimental group was monitored daily to record and remove dead adult aphids and nymphs.

RNA Extraction and cDNA Synthesis.

Adult aphids (10 insects) were homogenized with a polypropylene pestle in 1 mL of TRIZOL reagent according to the protocol supplied by the manufacturer (Invitrogen, Calif., USA) to extract the RNA. DNA contamination in the dsRNA samples was minimized by treating the RNA fraction following the protocol provided in the TURBO DNA-free kit (Ambion, Austin, Tex., USA). RNA (4 µg of DNA-free) was reverse-transcribed into complementary DNA (cDNA) using the SuperScript III First Strand Synthesis System for RT-PCR (Invitrogen, Calif., USA). A similar procedure was applied for *Tribolium* larvae (7 insects).

dsRNA Synthesis.

The nucleotide sequences of target genes from both insects (pea aphid: p-BiP: NCBI Accession No. XM_003244000.1); *Tribolium castaneum*: TcBiP: XM_015982882.1; TcArmet: XM_966545.3; TcVer: NM_001039410) were obtained from the NCBI database. Gene-specific primers including the T7 polymerase promoter sequences at the 5' end were used to synthesize dsRNA from respective insects (see Table 1) according to the AmpliScribe™ T7 Flash Transcription Kit protocol (Cat. No. ASF3507, Epicentre Biotechnologies, USA).

TABLE 1

| The primers used for dsRNA synthesis | | | | | |
|---|---|---|---|---|---|
| NCBI Accession No. | Gene name | Oligonucleotide sequences | Expected size (bp) | SEQ ID NO: | Annealing Temp. |
| *Acyrthosiphon pisum* | | | | | |
| XM_003244000.1 | p-Bip | p-dsBip-RNA-F: CCATCTTGCATGGAGACAAATC | 390 bp | 7 | 56° C. |
| | | p-dsBip-RNA-R: CCCTTATCGTTGGTGATGGTTA | | 8 | |

TABLE 1-continued

The primers used for dsRNA synthesis

| NCBI Accession No. | Gene name | Oligonucleotide sequences | Expected size (bp) | SEQ ID NO: | Annealing Temp. |
|---|---|---|---|---|---|
| XM_967161 Reference gene | L27 | p-Bip_qPCR-F: CTGAAGAAGTCCAAGAC | 150 bp | 9 | 55° C. |
| | | p-Bip_qPCR-R: GGTTATCAGAGTAGGTG | | 10 | |
| | | L27-qPCR-F: TCGTTACCCTCGGAAAGTC | 180 bp | 11 | 55° C. |
| | | L27-qPCR-R: GTTGGCATAAGGTGGTTGT | | 12 | |
| Tribolium castneum | | | | | |
| XM_015982882.1 | TcBip | TcdsBiP-RNA-F: ATCCCACGTAACACCGTAATC | 336 bp | 13 | 55° C. |
| | | TcdsBiP-RNA-R: GAACTTCTCCGCGTCTCTAATC | | 14 | |
| XM_966545.3 | TcArmet | TcdsArmet-RNA-F: CCAGTTTATCAGACGACGTGAA | 296 bp | 15 | 57° C. |
| | | TcdsArmet-RNA-R: CTTCAAATCCCTCACTTTGAGTTTC | 345 bp | 16 | 56° C. |
| NM_001039410.1 | TcVer | TcdsVer-RNA-F: ATCTACGAGCTGGACTCGAT | | 17 | |
| | | TcdsVer-RNA-R: GGTCAAAGACGGCTCTTTCT | | 18 | |

PCR products were separated on 1.4% agarose gels prepared in 40 mM Tris-acetate (pH 8.3) and 1 mM EDTA. Ethidium bromide was added to a final concentration of 0.7 µg/mL before allowing the agarose to solidify. The gels were photographed under UV light and images were captured by gel documentation (UVP-Digital Imaging System, Upland, Calif., USA).

Quantification of BiP by RT-PCR.

For days 1-8, gut tissues were collected each morning from BAPC-conjugated BiP-dsRNA treated and untreated pea aphids (20 insects/group). RNA was isolated from collected gut tissues as per the protocol described previously. RT-PCR was performed with gene specific primers for p-BiP gene. Each reaction contained 1 µL of cDNA, 1 µL of the specific primers (10 pmol/µL), and 10 µL of 2×SYBR Green Super-mix reagent (Bio-Rad) in a final volume of 20 µL. The following PCR program was used for all PCR reactions: 90° C. for 3 min, followed by 40 cycles of 95° C. for 30 s, 55° C. for 30 s, 72° C. for 30 s followed by 10 min at 72° C. at the end. Threshold Cycle (CT) values were calculated using Bio-Rad CFX Manager™ software (Bio-Rad). The Ct values were normalized with pea aphid using RpL27 primer (Forward: TCGTTACCCTCGGAAAGTC (SEQ ID NO:19); Reverse: GTTGGCATAAGGTGGTTGT (SEQ ID NO:20)) as reference gene for equal cDNA template amounts. Fold changes were calculated by comparing the normalized transcript level of free BiP-dsRNA treated samples to the BiP-dsRNA/BAPC treated group.

Statistical Analyses.

Statistics were performed using GraphPad Prism 5 software (GraphPad Software, La Jolla, Calif.). Statistical significance for DLS and ZP experiments was determined using ANOVA test followed by Bonferroni's post-test. For survival studies, the Log-rank (Mentel-Cox) test was used.

Results and Discussion

Biophysical Characterization of the BAPCs-dsRNA Particles.

Figure 19:
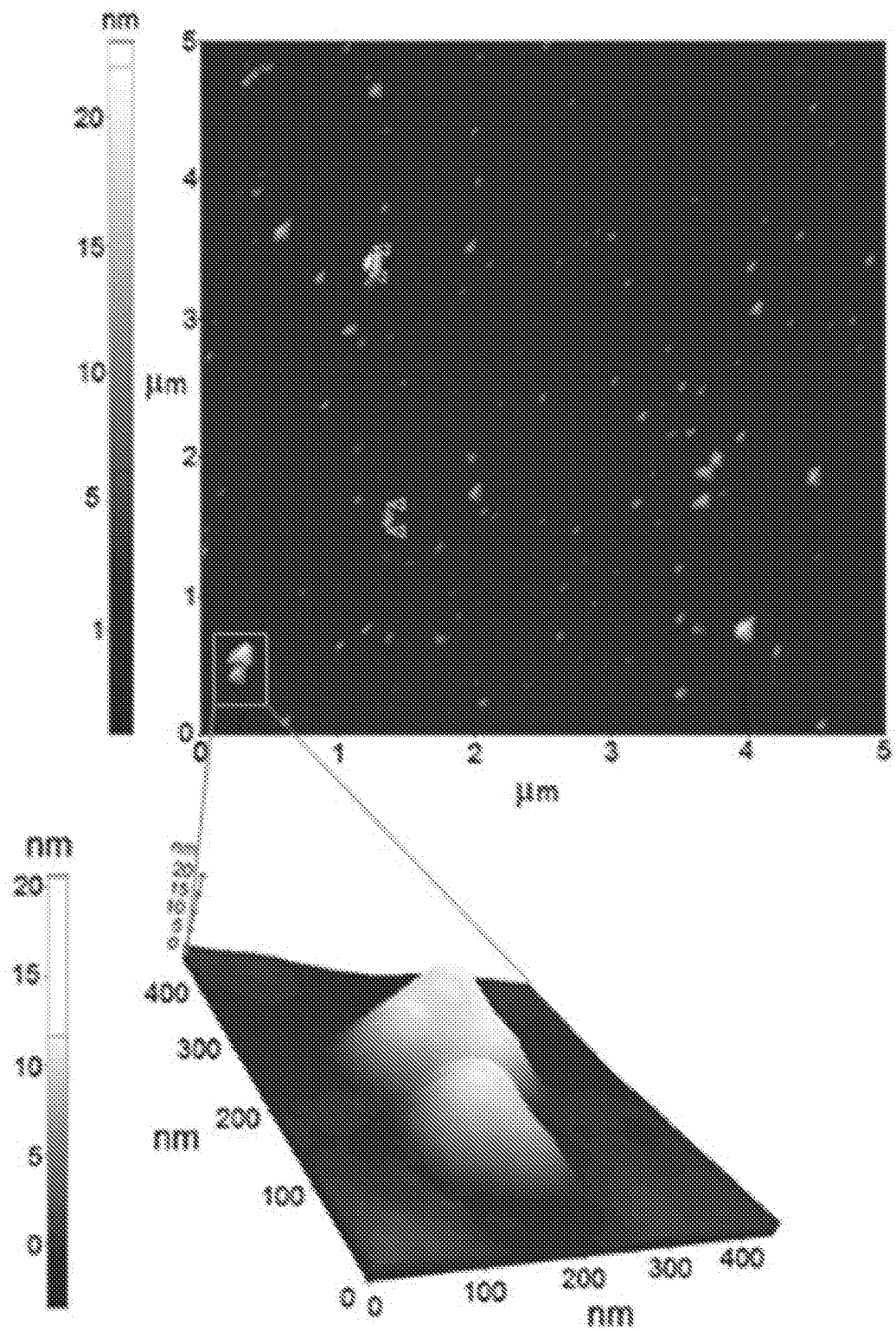
FIG. 19 shows a 5×5 µm AFM image analysis of the BACP-dsRNA nanoparticles (40 µM and 1 µg respectively), and a three-dimensional representation of the topography measured over a single BAPC-dsRNA nanoparticle.
Figure 20:
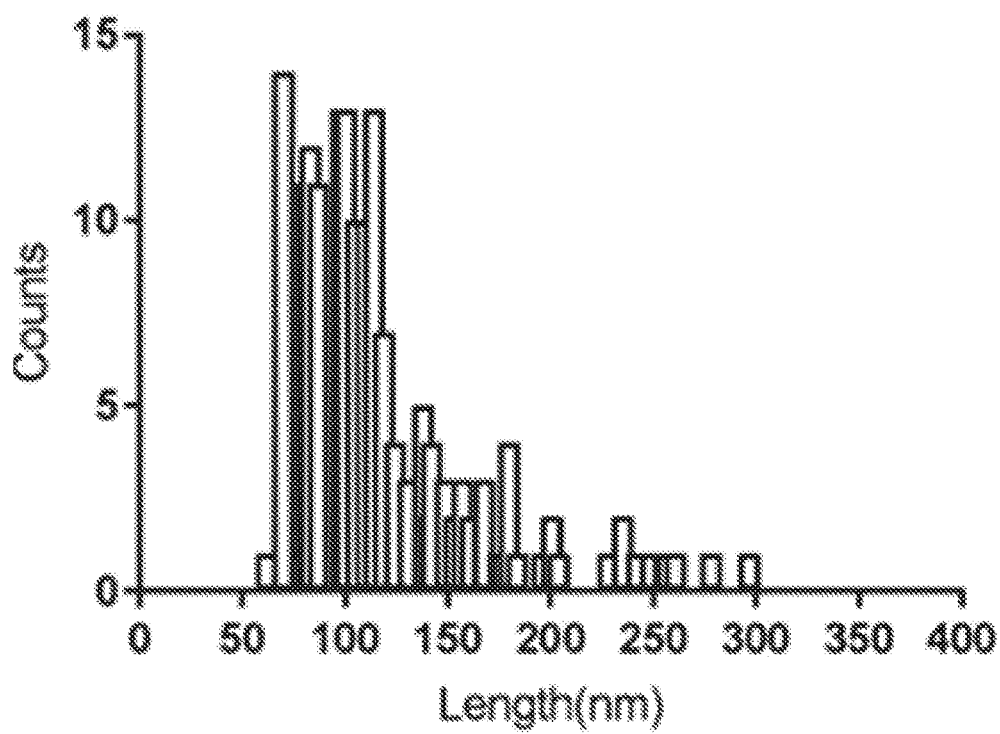
FIG. 20 is a graph showing the AFM Particle size distribution analysis.
Figure 21:
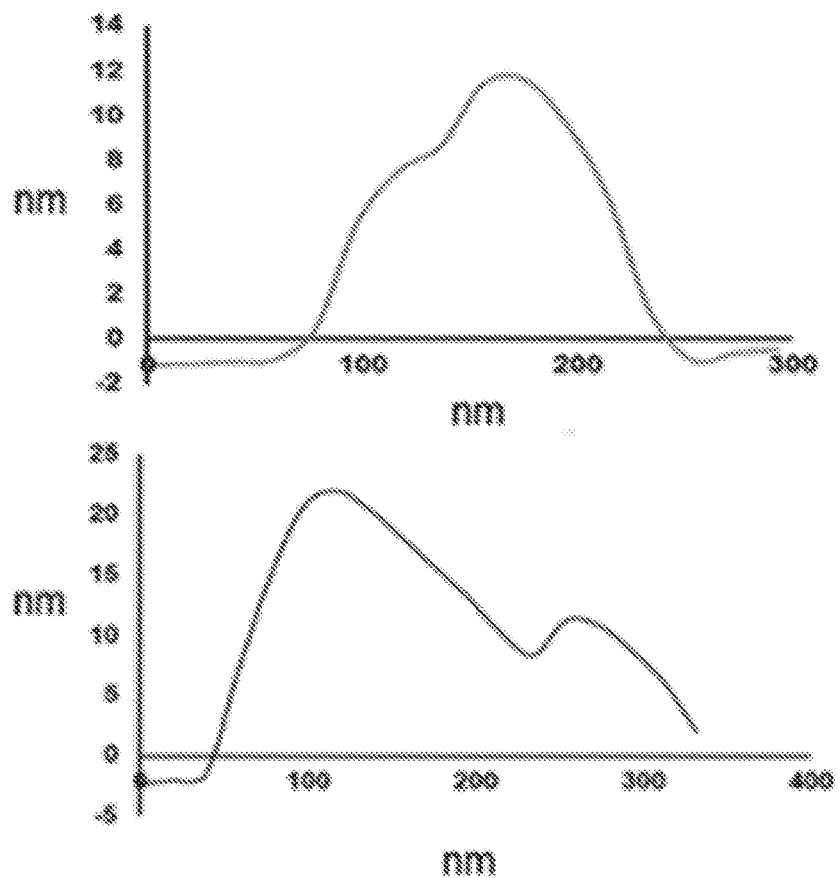
FIG. 21 is a graph of the profile analysis of two selected clusters.
Figure 22:
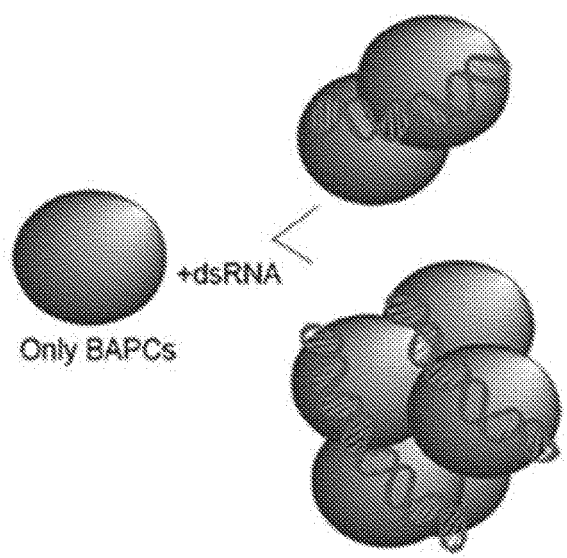
FIG. 22 is a schematic illustration of BAPCs-dsRNA interactions.

BAPCs preparation began by mixing the two peptides at equimolar concentration in 2,2,2, Trifluoroethanol (TFE). The solvent was removed under vacuum and subsequently water was added drop wise until reaching the desired concentration. The newly formed capsules were subjected to different temperature shifts to fix their size (20-30 nm). Nanocapsules prepared in this fashion are referred to as "conformationally constrained" because they have increased stability and their size is subsequently unaffected by solvents or chaotropes. We hypothesized that dsRNA interacts with the cationic surface of this "conformationally constrained" BAPCs by coating the surface, perhaps through winding, similar to the way that BAPCs interact with plasmid DNA. Atomic force microscopy (AFM) images of the BAPCs-RNAi complexes showed compact clusters ranging from 70 to 300 nm (FIG. 19), with similar morphologies that those previously reported for the pDNA-BAPCs complexes. A detailed particle size distribution (FIG. 20) shows that the majority of the particles are between 70 to 150 nm in diameter, meaning that most of the clusters involve the recruitment of two or three BAPCs. The profile analysis of two selected clusters is shown in FIG. 21. AFM analysis of only BAPCs shows single capsules with a size ranging from 25 to 50 nm. A schematic representation is illustrated in FIG. 22. To explore additional biophysical features of the BAPCs-dsRNA we performed a Dynamic Light Scattering (DLS) and Zeta Potential analyses. Different formulations were tested keeping the amount of dsRNA constant (1 µg) and varying the BAPCs concentration. Sizes ranging from 70 to 300 nm were observed by DLS, results that are in accordance with the particle sizes observed in AFM (FIG. 23A).

The complexes increased in size at high concentrations of the BAPCs suggesting that when the particles are in excess of the nucleic acids, the dsRNAs straddle multiple BAPCs thereby generating larger oligomeric states. Similar sizes were observed for the formulations containing lesser amounts of dsRNA indicating that the complexes are tightly bound as they do not readily dissociate upon dilution.

Figure 23:
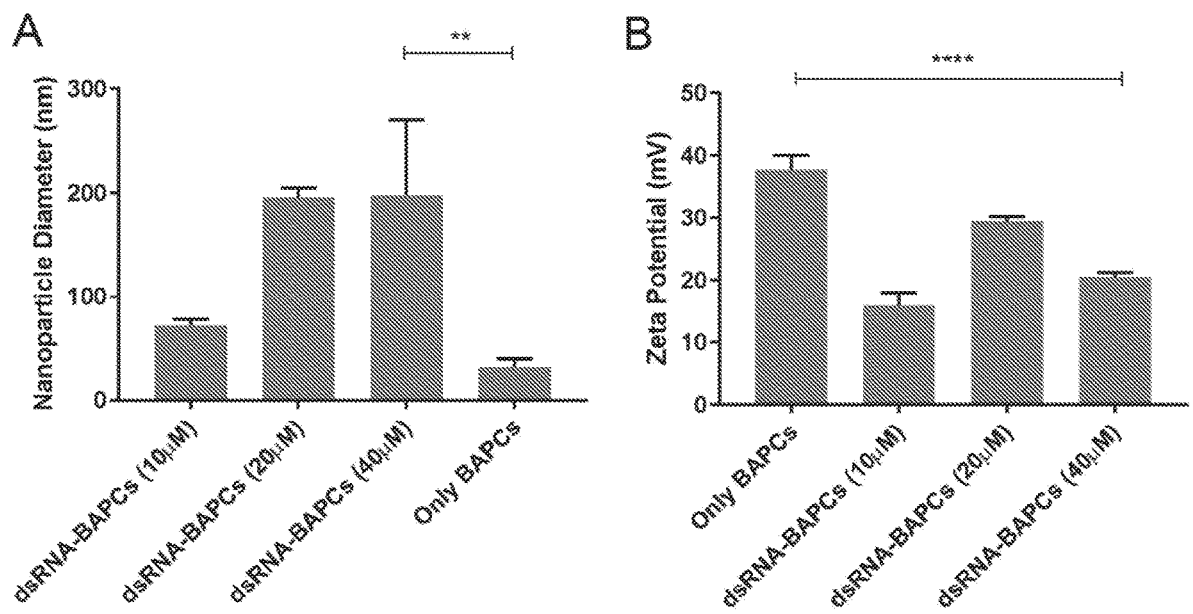
FIG. 23 contains graphs for the (A) Dynamic light scattering analysis of the nanoparticle size; and (B) zeta potential for different BAPCs-dsRNA formulations.

The zeta potentials (ZP) of the nanostructures were determined at several BAPC to dsRNA ratios (FIG. 23B). The ZP can be defined as the charge that develops at the interface between a solid surface and its liquid medium. Positive ZP's enhance the interaction with cell membranes however, values above 45 mV can be toxic. Particles with negative ZP do not interact efficiently with the negatively charge cell surface. The surface charges for the different dsRNA-BAPCs complexes ranged from, 10 to 28 mV. These results appeared to be suitable for generating strong interactions with the negatively-charged cell membrane surfaces but not so high as to trigger cell damage. We believe that even if the DNA surrounds the peptides capsules, there are a sufficient number of positives charges remaining on the capsule surface thus retaining a positive zeta potential.

BAPCs Deliver a Lethal dsRNA Added to the Artificial Liquid Diet of the Pea Aphid. *Acyrthosiphon pisum* is currently the model organism among aphids, with a sequenced genome and many Expressed Sequence Tags (ESTs), deposited at AphidBase.com. In the pea aphid, transcript knockdowns via RNAi have been reported, with most of relying on microinjection into the hemolymph. The pea aphid is commonly maintained in the laboratory on fava bean plants but it also does well on appropriate artificial liquid diets and the life span of an adult is about 20-30 days. We tested the ability of dsRNA/BAPC complexes to effectively deliver dsRNA to the pea aphid suspended in liquid diet.

Figure 24:
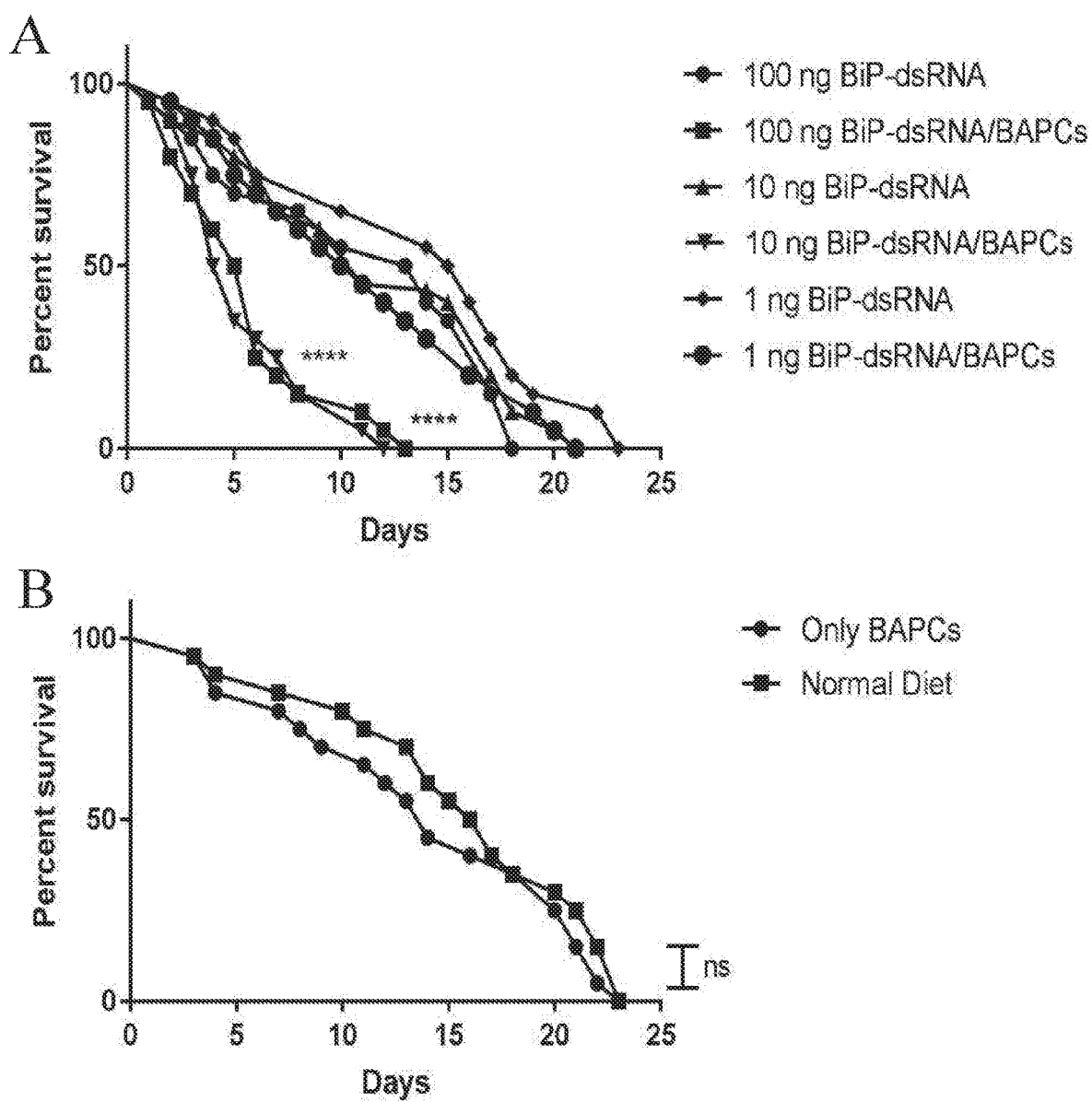
FIG. 24 contains survival curves showing (A) the effect of BAPCs complexed with varying concentrations of BiP-dsRNA in *Acyrthosiphon pisum*; (B) the comparison between an RNA-free diet without and without BAPCs.

In FIG. 24A we show survival curves for pea aphids that ingested dsRNA/BAPC complexes added to a standard artificial liquid diet (for 48 h) before being transferred to fava bean leaves. Mortality was monitored daily. Incubation of 5 insects with diets containing 10 or 100 ng of BiP-dsRNA (in the form of dsRNA/BAPCs complexes) led to the premature death of the aphids ($t_{1/2}$=4-5 days) compared to ingestion of the same amounts of free BiP-dsRNA ($t_{1/2}$=11-13 days). It should be noted that the actual amount of dsRNA/BAPC complexes ingested by an individual insect would be less than the total added to the shared diet. Feeding a diet containing just 1 ng of the dsRNA/BAPC complex had no effect. Ingestion of free dsRNA gave slightly earlier deaths, and the survival curve for insects that had ingested diet supplemented with only BAPCs was not statistically different from that for aphids that ingested normal diet with no additions (FIG. 24B). We tested four different BAPC concentrations with 100 ng dsRNA: 10, 20 40 and 100 µM (data no shown), with the 40 µM complex showing the highest inhibitory effect.

Figure 25:
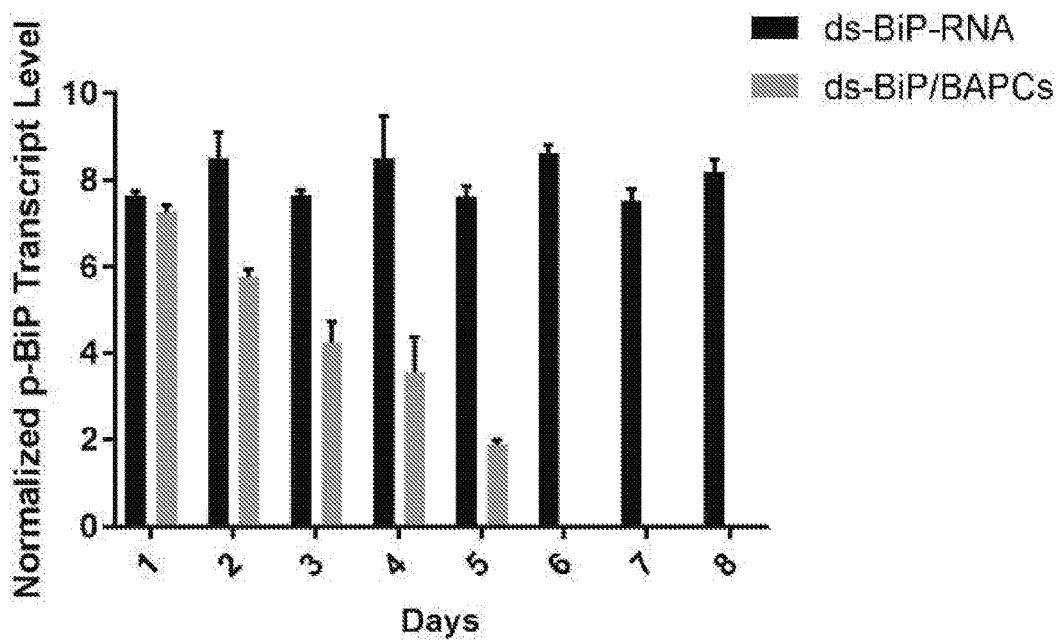
FIG. 25 shows Pea aphid (n=20 per group) transcript levels of BIP-mRNA isolated from gut of insects fed BiP-dsRNA with and without complexation with BAPCs. Time zero represents the mRNA levels of insects prior to placing them on the diet.

In insects that had ingested the dsRNA/BAPC complexes, the BiP transcript level in the aphids' guts fell dramatically (FIG. 25). The time course for the decrease in BiP transcript-level, preceded the survival curve of the aphids. The BiP transcript level did not change significantly when aphids ingested just free dsRNA added to their diet (FIG. 25). Our experiments with the pea aphid indicate that BAPCs very effectively deliver dsRNA from artificial liquid diet, markedly increasing the efficiency of RNAi-based knockdown of a transcript that encodes a vitally important protein.

Figure 26:
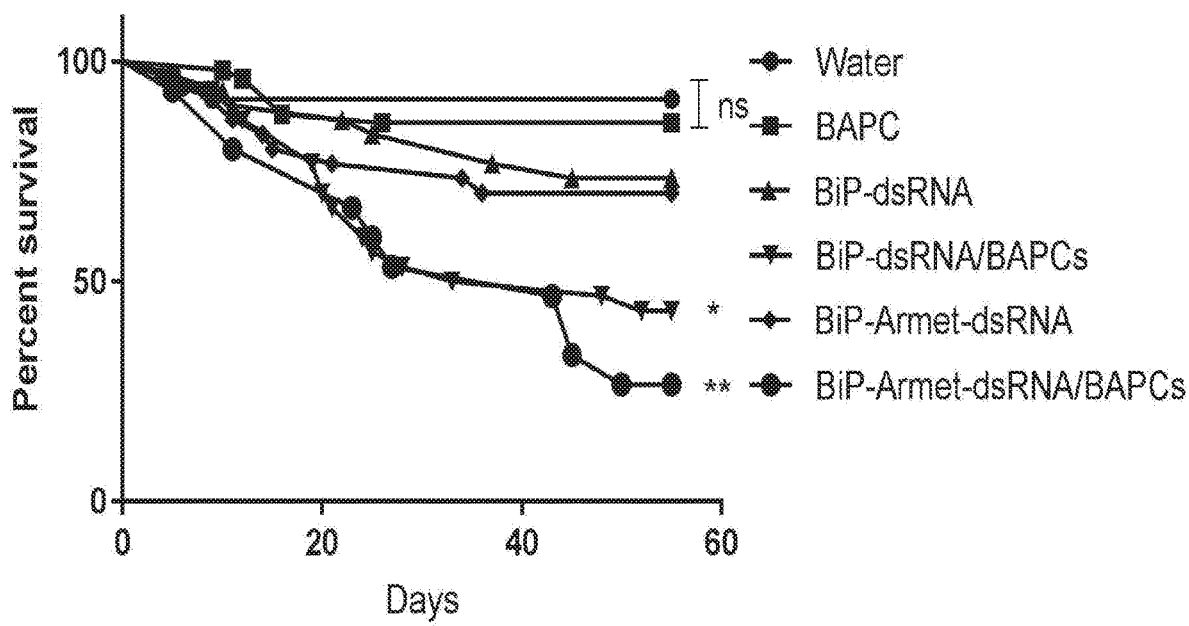
FIG. 26 shows a survival curve showing the effect of BAPCs complexed with dsArmet+BiP-dsRNA in *Tribolium castaneum*.
Figure 27:
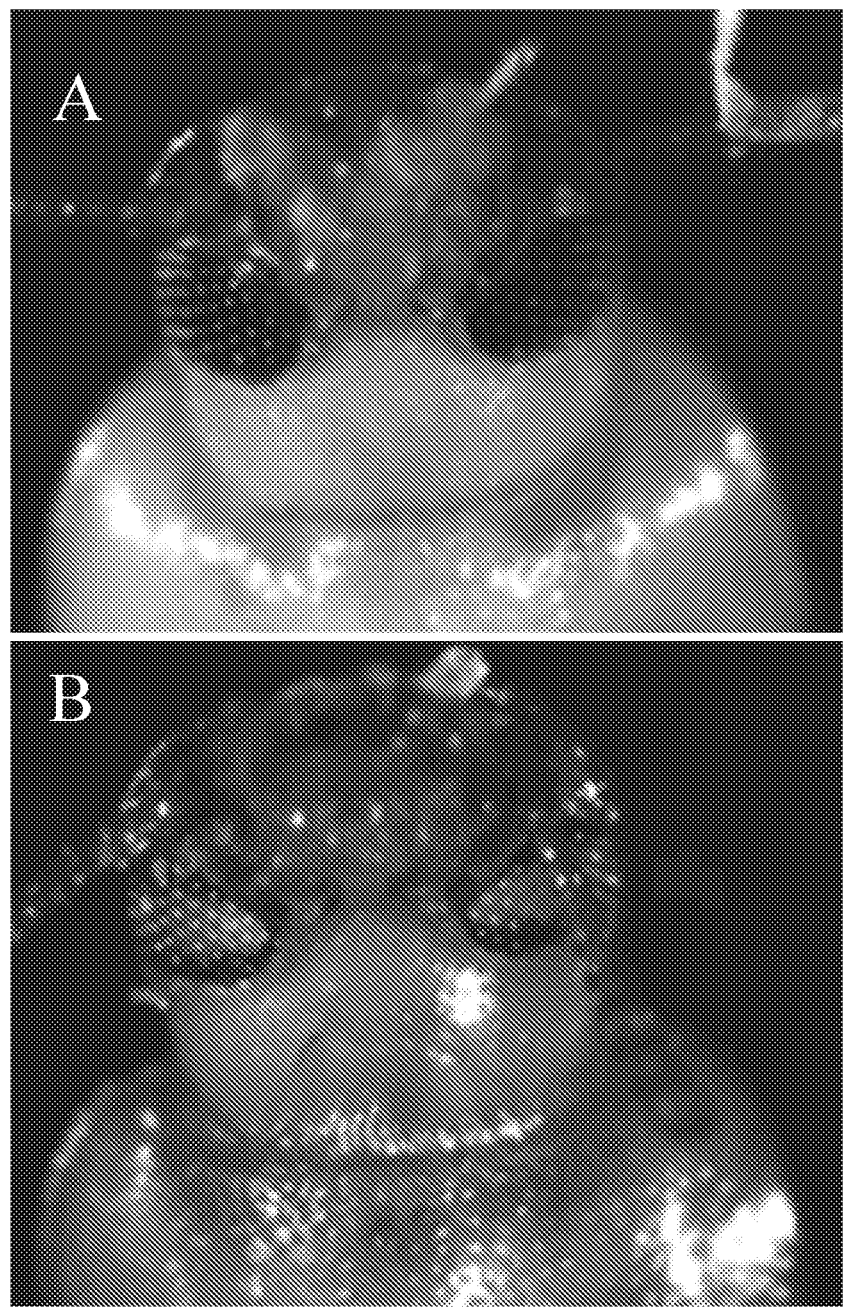
FIG. 27 contains photographs of (A) control *Tribolium* insects; and (B) *Tribolium* insects fed BAPCs-dsVermillion complexes in the flour diet of *Tribolium* larvae resulting in the absence of *Vermillion* color (in the eye) in treated insects.

BAPCs Effectively Deliver Lethal dsRNAs Added to the Solid Diet of *Tribolium castaneum*. *Tribolium castaneum* has become a prominent model organism. The insect's diet in nature is broken kernels of cereals, especially wheat. In the laboratory, *Tribolium* is typically maintained on wheat flour supplemented (at 5% w/w) with yeast extract. The standard method of delivering dsRNA to *Tribolium* is injection, often in larvae. The advantage of delivering dsRNA through diet rather than by injection is clear. FIG. 27 shows experiments with dsRNAs targeted at two components of the Unfolded Protein Response, namely BiP (GRP78) and Armet (MANF). As shown in the survival curves of FIG. 26, *Tribolium* is effectively killed by ingestion (by larvae) of a combination of BiP-dsRNA and Armet-dsRNA as dsRNA/BAPC complexes. These deaths (75% of the subjects, n=30) occurred in larvae or during eclosion (the emergence of adults from pupae). For those insects treated with dsRNAs alone their survival curves did not differ significantly from those with no additions to the diet (water alone). Larval/pupal deaths induced with the ingestion of the two dsRNA/BAPC complexes were significantly greater compared to the ingestion of either BiP-dsRNA or Armet-dsRNA complexed with BAPCs (50% and 40%, respectively—results not shown for Armet-dsRNA/BACPs). In another experiment, there were no deaths observed when these complexes were fed to adult insects, suggesting that either the targeted transcripts are not essential in adults or that the BAPC/dsRNA complexes are not readily taken-up by epithelium gut cells in adults.

*Tribolium* is well known for the systemic nature of its RNA interference. The *Vermillion* gene acts in the developing eye with its transcript encoding the protein required for the development of normal eye color. Ingestion of dsVermillion-RNA in complex with BAPCs requires movement of the complexes (or at least dsRNA released from the complexes) from the gut into the hemolymph. We found that ingestion of the complexes during late larval stages gave rise to adults with white (non-colored) eyes at a rather high frequency (about 50% with n=20), thus verifying the systemic nature of the RNAi effect created by ingestion of dsRNA/BAPC complexes. FIG. 27 shows and example of the white-eyed phenotype induced by the ingestion of dsRNA/BAPCs complexes.

Conclusions

BAPCs provide a chemically defined and controllable approach for reliably delivering double-stranded RNA to insect cells in either solid or liquid diets. The delivery is in the form of dsRNA/peptide complexes. The biophysical properties of the dsRNA/BAPC complexes are very similar to the BAPCs-DNA complexes described above. BAPCs mixed with dsRNA form compact clusters with sizes ranging predominantly from 50 to 300 nm and with zeta potentials ranging from 10 to 18 mV. AFM was also used to confirm the topologies of the BAPC-dsRNA complexes. Compact clusters were seen suggesting that the nucleic acids appeared to surround the cationic surface of the peptide capsules. These results indicate that BAPCs may dramatically stabilize dsRNA and confer protection against degradation, while enhancing their uptake by gut epithelial cells.

In this work, we generated knockdowns in proteins involved in the UPR, which is activated in response to an accumulation of misfolded proteins in the lumen of the endoplasmic reticulum (ER). Proteins involved in the UPR restore normal function of the ER. Suppressing their active in gut epithelium cells can induce apoptosis interfering with the absorption of nutrients in insects. These results observed in two different insects, from two Orders, indicate that this approach could be widely applicable in other insects. Furthermore, these complexes should allow for RNAi-based transcript knockdown experiments in insect species which are too small for injection in the laboratory (including small aphid species such as the Russian Wheat Aphid or green bug) as well as field applications including the intentional killing or lessening of life-span and fecundity of insect pests of plants, animals and humans such as the virus-transmitting mosquitos, fleas, and ticks.

Example 4

In this study, we examined the stability of dsRNA and single stranded FANA-RNAi (AUM LifeTech, Inc.) in cow's blood in the presence and absence of BAPCs. The double stranded RNA used in this experiment was 240 bps in length while the FANA-RNAi was just 21 bases. The structural difference between normal ribonucleotides and FANA nucleotides is the presence of a fluorine group on the 2-position of the ribose sugar. FANA RNA silencing technology provides for a more efficient knockdown of the target RNA, an ability to bind to the target RNA (mRNA, miRNA or lncRNA) in a highly sequence specific manner, with no toxicity, and no need for an external source (e.g. without a transfection agent, formulation, conjugate or viral vector). In addition, FANA-RNAs are more stable in blood than dsRNA. FANA-based technology design is currently being used in human clinical trials for HIV and certain cancers with positive results; however, current delivery approaches require high initial dosing amounts to achieve an effective delivered dose of the therapeutic agent.

Figures 28, 29:
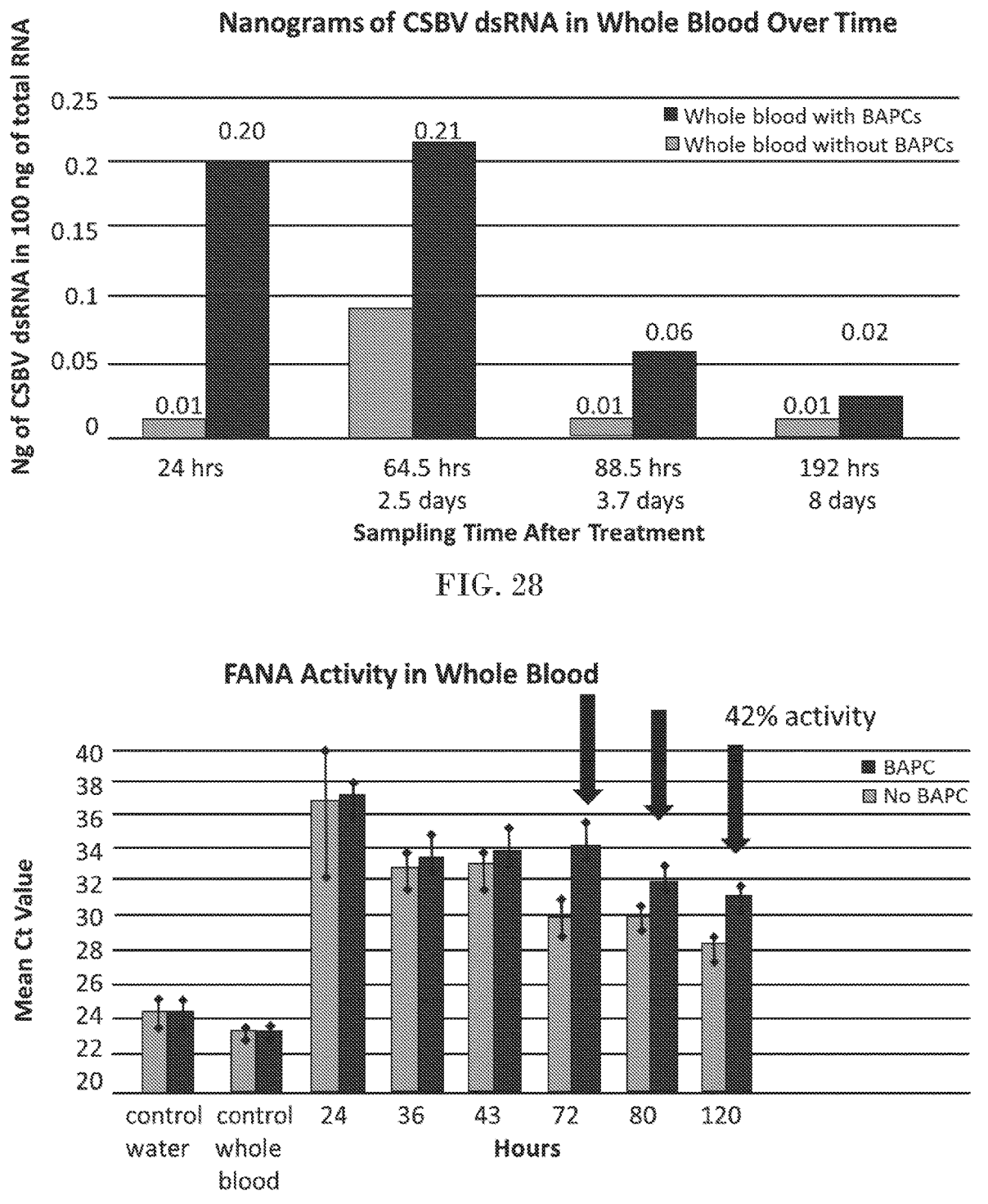

In the first experiment dsRNA was used (FIG. 28). Samples were removed at the indicated times and the added RNAs captured by a binding assay to the target mRNA attached to a solid support. It is clear that having the RNA complexed with the BAPCs retards its degradation.

In the second experiment, FANA RNAi alone, or complexed with BAPCs was

```
<213> ORGANISM: Artificial Sequence
<220> FEATURE:
<223> OTHER INFORMATION: Synthetic sequence designed from internal
      fragment of human dihydropyridine sensitive L-type calcium channel
      segment CaIVS3
<220> FEATURE:
<221> NAME/KEY: MISC_FEATURE
<222> LOCATION: (1)..(1)
<223> OTHER INFORMATION: Xaa is Phe, Tyr, Trp, or cyclohexylalanine

<400> SEQUENCE: 4

Xaa Leu Ile Val Ile
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence designed from internal
      fragment of human dihydropyridine sensitive CaIVS3 hydrophobic
      segment

<400> SEQUENCE: 5

Val Phe Phe Ile Val Ile Leu
1               5

<210> SEQ ID NO 6
<211> LENGTH: 9
<212> TYPE: PRT
<213> ORGANISM: Human papillomavirus type 16

<400> SEQUENCE: 6

Arg Ala His Tyr Asn Ile Val Thr Phe
1               5

<210> SEQ ID NO 7
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 7
ccatcttgca tggagacaaa tc                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 8
cccttatcgt tggtgatggt ta                                              22

<210> SEQ ID NO 9
<211> LENGTH: 17
<212> TYPE: DNA
<213> ORGANISM: Artificial Sequence
<220> FEATURE:
<223> OTHER INFORMATION: Synthetic forward primer

<400> SEQUENCE: 9
ctgaagaagt ccaagac                                                    17

<210> SEQ ID NO 10
```

```
<211> LENGTH: 17
<212> TYPE: DNA
<213> ORGANISM: Artificial Sequence
<220> FEATURE:
<223> OTHER INFORMATION: Synthetic reverse primer

<400> SEQUENCE: 10
ggttatcaga gtaggtg                                                     17

<210> SEQ ID NO 11
<211> LENGTH: 19
<212> TYPE: DNA
<213> ORGANISM: Artificial Sequence
<220> FEATURE:
<223> OTHER INFORMATION: Synthetic forward primer

<400> SEQUENCE: 11
tcgttaccct cggaaagtc                                                   19

<210> SEQ ID NO 12
<211> LENGTH: 19
<212> TYPE: DNA
<213> ORGANISM: Artificial Sequence
<220> FEATURE:
<223> OTHER INFORMATION: Synthetic reverse primer

<400> SEQUENCE: 12
gttggcataa ggtggttgt                                                   19

<210> SEQ ID NO 13
<211> LENGTH: 21
<212> TYPE: DNA
<213> ORGANISM: Artificial Sequence
<220> FEATURE:
<223> OTHER INFORMATION: Synthetic forward primer

<400> SEQUENCE: 13
atcccacgta acaccgtaat c                                                21

<210> SEQ ID NO 14
<211> LENGTH: 22
<212> TYPE: DNA
<213> ORGANISM: Artificial Sequence
<220> FEATURE:
<223> OTHER INFORMATION: Synthetic reverse primer

<400> SEQUENCE: 14
gaacttctcc gcgtctctaa tc                                               22

<210> SEQ ID NO 15
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 15
ccagtttatc agacgacgtg aa                                               22

<210> SEQ ID NO 16
<211> LENGTH: 25
<212> TYPE: DNA
<213> ORGANISM: Artificial Sequence
<220> FEATURE:
<223> OTHER INFORMATION: Synthetic reverse primer

<400> SEQUENCE: 16
```

```
cttcaaatcc ctcactttga gtttc                                          25

<210> SEQ ID NO 17
<211> LENGTH: 20
<212> TYPE: DNA
<213> ORGANISM: Artificial Sequence
<220> FEATURE:
<223> OTHER INFORMATION: Synthetic forward primer

<400> SEQUENCE: 17
atctacgagc tggactcgat                                                20

<210> SEQ ID NO 18
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 18
ggtcaaagac ggctctttct                                                20

<210> SEQ ID NO 19
<211> LENGTH: 19
<212> TYPE: DNA
<213> ORGANISM: Artificial Sequence
<220> FEATURE:
<223> OTHER INFORMATION: Synthetic forward primer

<400> SEQUENCE: 19
tcgttaccct cggaaagtc                                                 19

<210> SEQ ID NO 20
<211> LENGTH: 19
<212> TYPE: DNA
<213> ORGANISM: Artificial Sequence
<220> FEATURE:
<223> OTHER INFORMATION: Synthetic reverse primer

<400> SEQUENCE: 20
gttggcataa ggtggttgt                                                 19
```

The invention claimed is:

1. A nucleic acid-peptide capsule complex comprising:
a peptide capsule comprising a bilayer membrane having an exterior surface and defining a liquid-receiving interior space, wherein said membrane comprises a plurality of branched, amphipathic peptides, each of said peptides comprising a C-terminal hydrophilic segment coupled to a branch point, said branch point being coupled to two respective N-terminal hydrophobic segments; and
a nucleic acid molecule bound to and extending along said membrane exterior surface.

2. The nucleic acid-peptide capsule complex of claim 1, wherein said nucleic acid wraps around said peptide capsule.

3. The nucleic acid-peptide capsule complex of claim 1, wherein said nucleic acid is bound via electrostatic interactions with said membrane exterior surface.

4. The nucleic acid-peptide capsule complex of claim 1, wherein said nucleic acid is selected from the group consisting of plasmid DNA, mRNA, dsRNA, ssRNA, microRNA, RNAi, FANA-RNA, combinations thereof, and derivatives thereof.

5. The nucleic acid-peptide capsule complex of claim 1, wherein said nucleic acid has a total length of less than about 100,000 nucleotides.

6. The nucleic acid-peptide capsule complex of claim 1, wherein said capsule membrane is substantially free of lipids or phospholipids.

7. The nucleic acid-peptide capsule complex of claim 1, wherein said peptide capsule has a particle size of less than about 200 nm.

8. The nucleic acid-peptide capsule complex of claim 1, wherein said complex has a particle size of less than about 250 nm.

9. The nucleic acid-peptide capsule complex of claim 1, wherein said bilayer membrane is characterized by an inner leaflet presenting an interior surface facing said liquid-receiving interior space and an outer leaflet presenting said exterior surface, wherein said bilayer comprises a hydrophobic central region between said interior and exterior surfaces.

10. The nucleic acid-peptide capsule complex of claim 9, wherein said inner leaflet comprises a plurality of first amphipathic, branched peptides having a first number of amino acid residues, and said outer leaflet comprises a plurality of a second amphipathic, branched peptides having a second number of amino acid residues.

11. The nucleic acid-peptide capsule complex of claim 10, said first number of amino acid residues being different from said second number of amino acid residues.

12. The nucleic acid-peptide capsule complex of claim 10, said first number of amino acid residues being the same as said second number of amino acid residues.

13. The nucleic acid-peptide capsule complex of claim 10, said first amphipathic, branched peptides having hydrophilic segments oriented toward said liquid-receiving interior space and defining said interior surface, and said second amphipathic, branched peptide having hydrophilic segments oriented away from said nanoparticle core and defining said exterior surface, wherein each of said hydrophobic segments of said first and second peptides are oriented inward away from said interior and exterior surfaces and defining said hydrophobic central region of said bilayer member.

14. The nucleic acid-peptide capsule complex of claim 10, said hydrophobic central region comprising interlocking hydrophobic segments wherein the hydrophobic segments of said first peptide interdigitate with the hydrophobic segments of said second peptide in a parallel beta-sheet structure.

15. The nucleic acid-peptide capsule complex of claim 1, wherein said peptide hydrophilic segment consists of from about 1 to about 7 lysine residues.

16. The nucleic acid-peptide capsule complex of claim 1, wherein said peptide hydrophobic segments are selected from the group consisting of XLIVIGSII (SEQ ID NO: 3), XLIVI (SEQ ID NO: 4), and VFFIVIL (SEQ ID NO: 5), where X is F, Y, W, or cyclohexylalanine.

17. The nucleic acid-peptide capsule complex of claim 1, wherein each of said N-terminal hydrophobic segments is capped with an acetyl group, —NH$_2$, naphthalene, fluorenylmethyloxycarbonyl, and/or anthracene.

18. The nucleic acid-peptide capsule complex of claim 1, wherein said peptide branch point is a branched lysine, diaminopropionic acid, ornithine, diaminobutyric acid, or homolysine.

19. The nucleic acid-peptide capsule complex of claim 1, said peptide being selected from the group consisting of bis(h)-K—K$_n$ and the N-acetylated derivatives thereof, where h is a hydrophobic amino acid sequence selected from the group consisting of XLIVIGSII (SEQ ID NO: 3), XLIVI (SEQ ID NO: 4), and VFFIVIL (SEQ ID NO: 5), where X is F, —K— is a branched lysine residue, K is lysine, and n is from about 1 to about 7.

20. The nucleic acid-peptide capsule complex of claim 1, further comprising a solute dissolved or dispersed in said liquid-receiving interior space.

21. The nucleic acid-peptide capsule complex of claim 20, wherein said solute is selected from the group consisting of a marker dye, therapeutic active agent, small enzymes, antimicrobial agents, radionuclides, anti-cancer agents, apoptogenic agents, and combinations thereof.

22. The nucleic acid-peptide capsule complex of claim 1, further comprising a functional moiety conjugated to said complex, wherein said functional moiety is selected from the group consisting of fluorophores, dyes, targeting moieties and ligands, biotin, radioactive labels, and sequentially linked combinations thereof.

23. A composition comprising a plurality of nucleic acid-peptide capsule complexes according to claim 1 dispersed in a pharmaceutically-acceptable carrier or excipient.

24. The composition of claim 23, further comprising a plurality of said complexes aggregated together into clusters dispersed in a pharmaceutically-acceptable carrier or excipient.

25. A method of transfecting a cell, comprising incubating cells with a plurality of nucleic acid-peptide capsule complexes according to claim 1.

26. A method of delivering nucleic acid to a subject, said method comprising administering a plurality of nucleic acid-peptide capsule complexes according to claim 1 to said subject.

27. The method of claim 26, further comprising providing a plurality of said nucleic acid-peptide capsule complexes in dried form, dispersing said nucleic acid-peptide capsule complexes in an aqueous solution to prepare a vaccine, and administering said vaccine to said subject.

28. A method of preparing a nucleic acid-peptide capsule complex, said method comprising mixing a plurality of peptide capsules with nucleic acid in a solvent system under ambient conditions and for a sufficient time period for said nucleic acid to bind to said peptide capsules through electrostatic interactions to yield said nucleic acid-peptide capsule complexes, wherein said peptide capsules each comprise a bilayer membrane having an exterior surface and defining a liquid-receiving interior space, wherein said membrane comprises a plurality of branched, amphipathic peptides, each of said peptides comprising a C-terminal hydrophilic segment coupled to a branch point, said branch point being coupled to two respective N-terminal hydrophobic segments.

29. The method of claim 28, wherein said peptide capsules are mixed with an excess of said nucleic acid, wherein said complexes aggregate together into nucleic acid-peptide capsule clusters.

30. A peptide capsule complex for RNA interference of a target arthropod gene, said complex comprising:
a peptide capsule comprising a bilayer membrane having an exterior surface and defining a liquid-receiving interior space, wherein said membrane comprises a plurality of branched, amphipathic peptides, each of said peptides comprising a C-terminal hydrophilic segment coupled to a branch point, said branch point being coupled to two respective N-terminal hydrophobic segments; and
an arthropod RNA bound to and extending along said membrane exterior surface, wherein said RNA is complementary to at least a portion of mRNA of said target arthropod gene.

31. A method of inhibiting a target gene in a target arthropod using RNA interference, said method comprising orally delivering a peptide capsule complex according to claim 30 to said arthropod.

32. The method of claim 31, wherein said peptide capsule complex is dispersed in an edible arthropod attractant or feed.

33. An arthropod bait useful for oral administration of RNA for RNA interference in arthropods, said bait comprising a peptide capsule complex according to claim 30 and an edible arthropod attractant.

34. The arthropod bait of claim 33, wherein said bait is in a form selected from the group powder, liquid, gel, self-sustaining gel-matrix, tablet, granular, and combinations thereof.

* * * * *